United States Patent
Plat et al.

(10) Patent No.: US 12,257,224 B2
(45) Date of Patent: Mar. 25, 2025

(54) METHODS OF ADMINISTRATION FOR HIGHLY WATER-SOLUBLE SALTS OF A SHORT ACTING PHENYLALKYLAMINE CALCIUM CHANNEL BLOCKER

(71) Applicant: Milestone Pharmaceuticals Inc., Saint-Laurent (CA)

(72) Inventors: Francis Plat, Saint-Laurent (CA); Douglas Wight, Saint-Laurent (CA)

(73) Assignee: Milestone Pharmaceuticals Inc., Montréal (CA)

(*) Notice: Subject to any disclaimer, the term of this patent is extended or adjusted under 35 U.S.C. 154(b) by 0 days.

(21) Appl. No.: 17/865,697

(22) Filed: Jul. 15, 2022

(65) Prior Publication Data

US 2023/0065401 A1 Mar. 2, 2023

Related U.S. Application Data

(60) Provisional application No. 63/276,238, filed on Nov. 5, 2021, provisional application No. 63/222,174, filed on Jul. 15, 2021.

(51) Int. Cl.
| | |
|---|---|
| *A61K 31/277* | (2006.01) |
| *A61K 31/7048* | (2006.01) |
| *A61K 31/7076* | (2006.01) |
| *A61K 45/06* | (2006.01) |
| *A61K 47/18* | (2017.01) |
| *A61P 9/06* | (2006.01) |

(52) U.S. Cl.
CPC ........ *A61K 31/277* (2013.01); *A61K 31/7048* (2013.01); *A61K 31/7076* (2013.01); *A61K 45/06* (2013.01); *A61K 47/183* (2013.01); *A61P 9/06* (2018.01)

(58) Field of Classification Search
CPC ........ A61K 31/277; A61K 47/183; A61P 9/06
See application file for complete search history.

(56) References Cited

U.S. PATENT DOCUMENTS

| | | |
|---|---|---|
| 9,227,918 B2 | 1/2016 | Maguire et al. |
| 9,463,179 B2 | 10/2016 | Maguire et al. |
| 9,737,503 B2 | 8/2017 | Maguire et al. |
| 10,010,522 B2 | 7/2018 | Maguire et al. |
| 10,010,523 B2 | 7/2018 | Maguire et al. |
| 10,010,524 B2 | 7/2018 | Maguire et al. |
| 10,117,848 B2 | 11/2018 | Maguire |

FOREIGN PATENT DOCUMENTS

| | | |
|---|---|---|
| WO | WO-2008/156820 A1 | 12/2008 |
| WO | WO-2016/165014 A1 | 10/2016 |

OTHER PUBLICATIONS

Extended European Search Report for European Patent Application No. 22185163.7, dated Dec. 20, 2022 (10 pages).
Francis, "Node Clinical Trials of Etripamil Nasal Spray for PSVT," All About Cardiovascular System and Disorders, <https://johnsonfrancis.org/professional/node-clinical-trials-of-etripamil-nasal-spray-for-psvt/>, dated Aug. 2022, retrieved on Mar. 9, 2023 (3 pages).
Ip et al., "Abstract 11430: Etripamil Nasal Spray Reduces Heart Rate in Patients with Paroxysmal Supraventricular Tachycardia Prior to Conversion to Sinus Rhythm," Circulation. 144:A11430 (Nov. 2021) (5 pages).
Ip et al., "Abstract 9925: Patient-Reported Treatment Satisfaction in Etripamil-Mediated Conversion of Supraventricular Tachycardia to Sinus Rhythm: Results from the NODE-301 Study," Circulation. 146:A9925 (Oct. 2022) (5 pages).
Stambler et al., "Etripamil Nasal Spray for Rapid Conversion of Supraventricular Tachycardia to Sinus Rhythm," J Am Coll Cardiol. 72(5):489-497 (Jul. 2018).
Stambler et al., "Rationale for and design of a multicenter, placebo-controlled, phase 3 study to assess efficacy and safety of intranasal etripamil for the conversion of paroxysmal supraventricular tachycardia," Am Heart J. 253:20-29 (Nov. 2022).
Wight et al., "Safety, Tolerability, Pharmacokinetics, and Pharmacodynamics of Intranasal Etripamil in Healthy Japanese and Non-Japanese Adults," J Am Coll Cardiol. 79(9_Supplement A):43 (Mar. 2022).

*Primary Examiner* — Shobha Kantamneni
(74) *Attorney, Agent, or Firm* — Clark & Elbing LLP

(57) ABSTRACT

The present invention is related to methods of treating cardiac arrhythmia, angina, or a migraine in a patient in need thereof, with a therapeutically effective amount of a compound having a structure according to the formula:

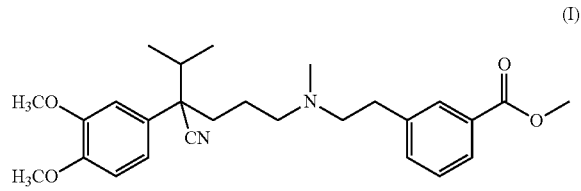

(I)

the method comprising nasally administering to the patient (i) a first dose, and (ii) a second dose of an aqueous composition comprising a pharmaceutically acceptable acetate or methanesulfonate salt of compound I, or a racemate or enantiomer thereof, wherein the acetate or methanesulfonate salt of compound I, or the racemate or enantiomer thereof, is dissolved in the aqueous composition at a concentration of 350 mg/mL±50 mg/mL, and wherein the second dose of the compound is administered between 5 minutes and 25 minutes after the first dose.

22 Claims, 17 Drawing Sheets

METHODS OF ADMINISTRATION FOR HIGHLY WATER-SOLUBLE SALTS OF A SHORT ACTING PHENYLALKYLAMINE CALCIUM CHANNEL BLOCKER

BACKGROUND OF THE INVENTION

Cardiac arrythmias and angina are problematic, and potentially life-threatening conditions. While there are currently several therapeutic modalities available to subjects who suffer from chronic cardiac arrhythmia and angina, these platforms generally suffer from several deficiencies, chief among them being invasiveness or inefficiency. Thus, there is a need for better treatments of cardiac arrhythmia and angina.

SUMMARY OF THE INVENTION

Embodiments of the invention include methods of treating cardiac arrhythmia (e.g., paroxysmal supraventricular tachycardia (PSVT) or atrial fibrillation), angina, and/or migraine.

The methods include administration of an aqueous composition formulated for nasal administration containing a pharmaceutically acceptable acetate or methanesulfonate salt of a compound of the formula (Compound I)

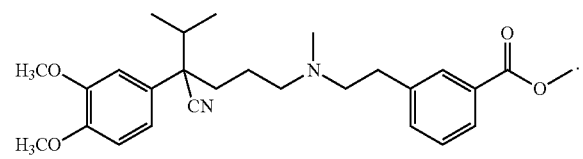

(I)

In some embodiments, the method includes a two dose administration of compound I. In view of the prolongation of the PR interval for a two dose regimen relative to a single dose regimen seen in subjects with sinus rhythm, the two dose regimen is likely to increase the percentage of subjects returning to normal heart rhythm from an incidence of cardiac arrhythmia.

One embodiment of the present invention is a method of treating a cardiac arrhythmia in a subject in need thereof with a therapeutically effective amount of compound I, the method comprising nasally administering to the subject (i) a first dose, and (ii) a second dose of an aqueous composition comprising a pharmaceutically acceptable acetate or methanesulfonate salt of compound I, or a racemate or enantiomer thereof, wherein the acetate or methanesulfonate salt of compound I, or the racemate or enantiomer thereof, is dissolved in the aqueous composition at a concentration of 350 mg/mL±50 mg/mL, and wherein the second dose of the compound is administered between 5 minutes and 25 minutes after the first dose.

One embodiment of the present invention is a method of treating angina in a subject in need thereof with a therapeutically effective amount of compound I, the method comprising nasally administering to the subject (i) a first dose, and (ii) a second dose of an aqueous composition comprising a pharmaceutically acceptable acetate or methanesulfonate salt of compound I, or a racemate or enantiomer thereof, wherein the acetate or methanesulfonate salt of compound I, or the racemate or enantiomer thereof, is dissolved in the aqueous composition at a concentration of 350 mg/mL±50 mg/mL, and wherein the second dose of the compound is administered between 5 minutes and 25 minutes after the first dose.

One embodiment of the present invention is a method of treating migraines in a subject in need thereof with a therapeutically effective amount of compound I, the method comprising nasally administering to the subject (i) a first dose, and (ii) a second dose of an aqueous composition comprising a pharmaceutically acceptable acetate or methanesulfonate salt of compound I, or a racemate or enantiomer thereof, wherein the acetate or methanesulfonate salt of compound I, or the racemate or enantiomer thereof, is dissolved in the aqueous composition at a concentration of 350 mg/mL±50 mg/mL, and wherein the second dose of the compound is administered between 5 minutes and 25 minutes after the first dose.

One embodiment of the present invention is an aqueous composition comprising a pharmaceutically acceptable acetate or methanesulfonate salt of compound I or a racemate or enantiomer thereof, for use in treating a cardiac arrhythmia in a subject in need thereof, wherein the aqueous composition is formulated for nasal administration to the subject as (i) a first dose, and (ii) a second dose, wherein the acetate or methanesulfonate salt of compound I, or the racemate or enantiomer thereof, is dissolved in the aqueous composition at a concentration of 350 mg/mL±50 mg/mL, and wherein the second dose of the compound is to be administered between 5 minutes and 25 minutes after the first dose.

One embodiment of the present invention is an aqueous composition comprising a pharmaceutically acceptable acetate or methanesulfonate salt of compound I or a racemate or enantiomer thereof, for use in treating angina in a subject in need thereof, wherein the aqueous composition is formulated for nasal administration to the subject as (i) a first dose, and (ii) a second dose, wherein the acetate or methanesulfonate salt of compound I, or the racemate or enantiomer thereof, is dissolved in the aqueous composition at a concentration of 350 mg/mL±50 mg/mL, and wherein the second dose of the compound is to be administered between 5 minutes and 25 minutes after the first dose.

One embodiment of the present invention is an aqueous composition comprising a pharmaceutically acceptable acetate or methanesulfonate salt of compound I or a racemate or enantiomer thereof, for use in treating migraines in a subject in need thereof, wherein the aqueous composition is formulated for nasal administration to the subject as (i) a first dose, and (ii) a second dose, wherein the acetate or methanesulfonate salt of compound I, or the racemate or enantiomer thereof, is dissolved in the aqueous composition at a concentration of 350 mg/mL±50 mg/mL, and wherein the second dose of the compound is to be administered between 5 minutes and 25 minutes after the first dose.

In some embodiments, the second dose of the compound is to be administered between 10 minutes and 15 minutes after the first dose. In some embodiments, the second dose is to be administered about 10 minutes after the first dose. In other embodiments, the second dose is to be administered between 30 and 60 minutes after the first dose.

In some embodiments, the aqueous composition comprises the acetate salt of compound I.

In some embodiments, the aqueous composition comprises the acetate salt of the S-enantiomer of compound I.

In some embodiments, the cardiac arrhythmia is paroxysmal supraventricular tachycardia (PSVT), atrial fibrillation, or ventricular tachycardia.

In some embodiments, the cardiac arrhythmia is PSVT.

In some embodiments, the cardiac arrhythmia is atrial fibrillation.

In some embodiments, the angina is stable angina or Prinzmetal's angina.

In some embodiments, the first and the second dose each comprises between 150 microliters and 200 microliters of the aqueous composition.

In some embodiments, the first and the second dose each comprises no more than two single pump spray dosages.

In some embodiments, each single pump spray dosage comprises 35 mg±3.5 mg of the acetate salt of the S-enantiomer of compound I.

In some embodiments, each of the first and the second dose comprises administering no more than 100 microliters of the aqueous composition to each nostril of the subject.

In some embodiments, the subject is a human.

In some embodiments, the aqueous composition comprises from 40% to 85% (w/v) water.

In some embodiments, the aqueous composition has a pH of 4.5±1.5.

In some embodiments, the aqueous composition has a pH of 4.5±0.1.

In some embodiments, the aqueous composition further comprises a chelating agent.

In some embodiments, the aqueous composition further comprises EDTA.

In some embodiments, the aqueous composition further comprises a pharmaceutically acceptable excipient.

In some embodiments, the aqueous composition is a homogeneous composition at room temperature.

One embodiment of the present invention is a method of treating atrial fibrillation in a subject in need thereof with a therapeutically effective amount of compound I, the method comprising nasally administering to the subject an aqueous composition comprising a pharmaceutically acceptable acetate or methanesulfonate salt of compound I, or a racemate or enantiomer thereof, wherein the acetate or methanesulfonate salt of compound I, or the racemate or enantiomer thereof, is dissolved in the aqueous composition at a concentration of 350 mg/mL±50 mg/mL, and wherein the second dose of the compound is to be administered between 5 minutes and 60 minutes after the first dose (e.g., between 5 and 25 minutes, 10 and 35 minutes, 25 and 45 minutes, or 45 and 60 minutes after the first dose).

In some embodiments, the treatment comprises administering an aqueous composition comprising a pharmaceutically acceptable acetate or methanesulfonate salt of compound I, or a racemate or enantiomer thereof, as an adjunctive treatment where the subject is to be treated with at least one anti-arrhythmic medication.

In some embodiments, the anti-arrhythmic medication is a beta blocker, a calcium channel blocker, a sodium channel blocker, a potassium channel blocker, digoxin, digitalis, adenosine, or an antiplatelet drug.

In some embodiments, the method or composition for use reduces the heart rate of the subject.

In one embodiment the present invention is a kit for treating a cardiac arrhythmia (e.g., PSVT or atrial fibrillation), angina, or a migraine in a subject in need thereof wherein the kit comprises a nasal delivery system comprising two doses of a therapeutically effective amount of compound I having a structure according to the formula:

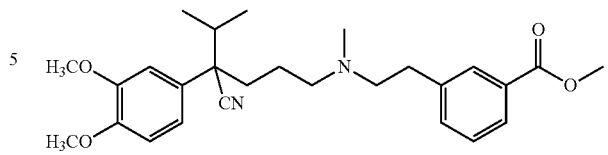

and instructions for nasally administering to the subject (i) a first dose, and, optionally, (ii) a second dose of an aqueous composition comprising a pharmaceutically acceptable acetate or methanesulfonate salt of compound I, or a racemate or enantiomer thereof, wherein the acetate or methanesulfonate salt of compound I, or the racemate or enantiomer thereof, is dissolved in the aqueous composition at a concentration of 350 mg/mL±50 mg/mL, and wherein the second dose of the compound is to be administered between 5 minutes and 60 minutes after the first dose.

Definitions

The term "tachycardia" as used herein refers to a resting heart rate that is elevated relative to a normal state.

"Cardiac arrhythmia" as used herein refers to a condition characterized by abnormal heart rhythms that are irregular, too fast, too slow, or conducted via an abnormal electrical pathway through the heart. Cardiac arrhythmias include atrial fibrillation that is characterized by irregularly irregular ventricular rhythm caused by abnormally erratic fast electrical discharge patterns that cause the atria to contract very rapidly thereby impairing efficient pumping of the blood into the ventricles. Cardiac arrhythmias also include paroxysmal supraventricular tachycardia (PSVT) that is characterized by a regular and fast heart rate originating in heart tissue above the ventricles. Cardiac arrhythmias also include ventricular tachycardia that is characterized by a rapid heartbeat that originates in the lower chambers of the heart.

The term "angina" as used herein refers to chest discomfort experienced due to ischemic heart disease. "Stable angina" is angina that is principally caused by arteriosclerosis.

The term "migraine" as used herein is a disease characterized by a recurrent headache that typically affects one side of the head and is often accompanied by nausea, vomiting, or sensitivity to light.

The term "atrial fibrillation" as used herein is a disease characterized by irregularly irregular ventricular rhythm caused by abnormally erratic fast electrical discharge patterns that cause the atria to contract very rapidly thereby impairing efficient pumping of the blood into the ventricles.

The term "excipient" is used herein to describe any ingredient other than an active compound (e.g., one having Formula I) described herein. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol. Additional excipients may include, without limitation, polysorbate, propylene glycol, hydroxypropyl β-cyclodextrin, triethylcitrate, benzalkonium chloride, and N-dodecyl-β-D-maltoside.

As used herein, a "chelating agent" is a molecule capable of forming at least two chemical bonds with a metal cation so as to form a complex.

As used herein, an "aminopolycarboxylic acid" is a molecule that includes at least one amine and at least two carboxylic acid functional groups. The carboxylic acids of an aminopolycarboxylic acid may be deprotonated and exist in anionic form as carboxylate groups. Examples of aminopolycarboxylic acids include, without limitation, iminodiacetic acid (IDA), nitrilotriacetic acid (NTA), pentetic acid (DTPA), ethylenediaminetetracetic acid (EDTA), ethylene glycol tetraacetic acid (EGTA), (1,2-bis(o-aminophenoxy)ethane-N,N,N',N'-tetraacetic acid) (BAPTA), 1,4,7,10-tetraazacyclododecane-1,4,7,10-tetraacetic acid (DOTA), and N—(N-(3-amino-3-carboxypropyl)-3-amino-3-carboxypropyl)azetidine-2-carboxylic acid (nicotianamine), among others.

As used herein, the term "nasal administration" means absorption of a compound or a pharmaceutically acceptable formulation of a compound by contacting the compound or formulation with the nasal epithelium. This can be achieved by spraying the compound or formulation into the nasal cavity. Desirably the compound is compound I.

As used herein, a "pharmaceutically acceptable salt" or "pharmaceutically acceptable acid addition salt" of a basic pharmaceutically active compound is derived from the treatment of the compound with an organic acid or an inorganic acid. Exemplary pharmaceutically acceptable acid addition salts include those derived from treatment of the compound with acetic acid or methanesulfonic acid.

A "pharmaceutically acceptable carrier" As used herein, refers to a vehicle capable of suspending or dissolving the active compound, and having the properties of being non-toxic and non-inflammatory in a patient. Moreover, a pharmaceutically acceptable carrier may include a pharmaceutically acceptable additive, such as a preservative, antioxidant, fragrance, emulsifier, dye, or excipient known or used in the field of drug formulation and that does not significantly interfere with the therapeutic effectiveness of the biological activity of the active agent, and that is non-toxic to the patient.

The term "pharmaceutically acceptable formulation" As used herein, refers to a composition including a pharmaceutically acceptable carrier and an active compound, e.g., the compound of Formula I.

As used herein, the term "therapeutically effective amount" refers to an amount of an active compound that, when administered to a patient, reduces, eliminates, or prevents one or more symptoms of a cardiac arrhythmia (such as PSVT), angina (such as stable angina), or migraine. Desirably, a therapeutically effective amount of a pharmaceutical formulation is an aqueous solution that contains a compound I at a concentration of about 350 mg/mL±50 mg/mL.

These definitions and others stated in The Merck Manual 16$^{th}$ edition 1992 (Chapter 25. pp 461-498; Chapter 25, pp 498-507; and Chapter 24, pp 413-429) and Goodman and Gilman's "The Pharmacological Basis of Therapeutics" 11$^{th}$ edition 2006 (Chapter 34, pp 899-908; Chapter 31, pp 823-824 and pp 830-832; and Chapter 32, pp 845-846) are herein incorporated by reference.

Other features and advantages of the invention will be apparent from the following Detailed Description and the Claims.

The box plot shown presents median (middle line in box), mean (diamond), first and third quartiles (ends of box), maximum and minimum values (whiskers), and outlines (circles).

HR=heart rate; SR=sinus rhythm. P=0.0371.

Figure 16:
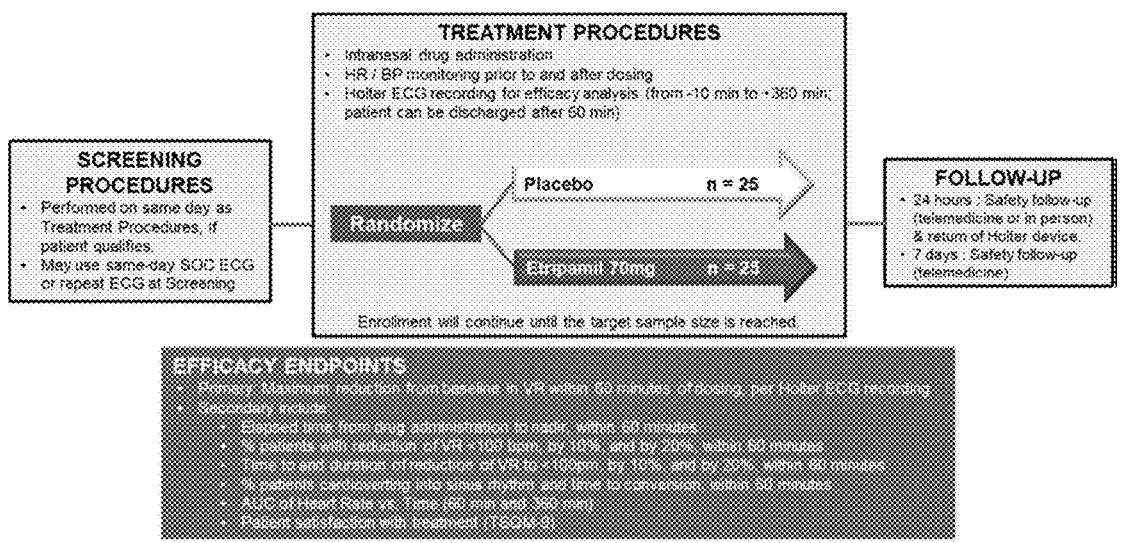

FIG. 16 is a schematic diagram showing a study design schematic for a clinical trial of treatment of atrial fibrillation (AF) with compound I.

Figure 17:
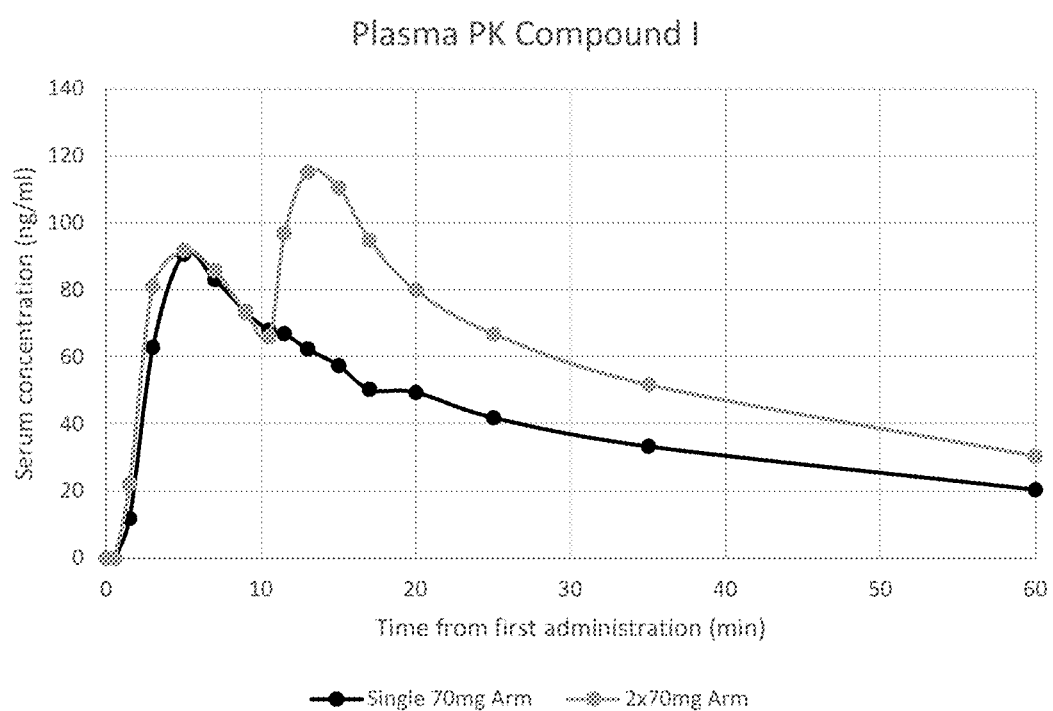

FIG. 17 is a graph showing the serum concentration of compound I (etripamil) over time from the first administration for the study arm with a single 70 mg dose administration of compound I (lower line) and the study arm with two 70 mg dose administrations of compound I (upper line), where the second 70 mg dose of compound I was administered approximately 10 minutes after the first dose.

DETAILED DESCRIPTION

The present invention is related to methods of treating a disease selected from the group consisting of cardiac arrhythmia (e.g., PSVT or atrial fibrillation), angina, and migraine, the method including administration of a second dose of a pharmaceutically acceptable salt of compound I dissolved in an aqueous composition, where the patient continues to experience disease symptoms ten minutes after the first dose.

Compound I (etripamil) of the present invention is methyl 3-(2-((4-cyano-4-(3,4-dimethoxyphenyl)-5-methylhexyl)(methyl)amino)ethyl)benzoate, shown below in Formula I.

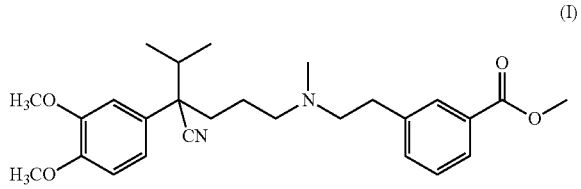 [SMILES: COC(=O)c1cccc(CCN(C)CCCC(C#N)(c2ccc(OC)c(OC)c2)C(C)C)c1]

(I)

Compound I, its formulation, manufacturing, and methods of use and treatment are described in U.S. Pat. No. 10,117,848, which is herein incorporated by reference in its entirety.

Cardiac Arrhythmia

Cardiac arrhythmia, or abnormal heart rhythm, is caused by abnormal excitation and conduction to the heart. A normal heartbeat is regulated by the sinoatrial (SA) node, a collection of cells embedded within the right atrium proximal to the superior vena cava. Under healthy physiological conditions, the SA node spontaneously initiates action potentials at regular intervals and propagates these electrochemical signals from the right atrium to the left atrium. Each coordinated pulse induces an influx of calcium ions ($Ca^{2+}$) into the cardiomyocyte fibers of the SA node through voltage-gated calcium channels, which ultimately enables the cardiac muscle tissue to contract and expel blood from the atria into the ventricles. This signal is subsequently propagated to the atrioventricular (AV) node, which propagates the action potential to the right and left ventricles. This signal triggers an influx of extracellular calcium, which in turn facilitates contraction of ventricular cardiomyocytes and the expulsion of blood from the heart and into circulation.

The precise coordination of these events is vital to maintaining a regular heartbeat, and the aberrant activity of this electrochemical conduction system gives rise to arrhythmia.

A recurrent arrhythmia with an abrupt onset and termination is designated as paroxysmal. Symptoms of paroxysmal supraventricular tachycardia (PSVT) include episodes of regular and paroxysmal palpitations with sudden onset and termination (Blomstrom-Lundqvist et al., *J. Am. Coll. Cardiol.*, 2003, 42:1493-531). The signaling mechanisms that underlie PSVT include the initiation and propagation of action potentials along accessory nodes that cause abnormal cardiomyocyte contractions that interfere with the coordinated atrial-to-ventricular blood flow. The most common form of PSVT is AV nodal reentrant tachycardia (AVNRT), a disorder characterized by the development of conducting tissue proximal to the AV node. This tissue forms a closed loop known as a reentry circuit, which enables action potentials to be propagated circularly throughout the heart rather than in a linear fashion. As a result, patients experience rapid palpitations and severely elevated heart rates. Episodes of tachycardia are often accompanied by a drop in blood pressure, which can induce dizziness or fainting. It is estimated that PSVT affects greater than 1.7 million treatable patients in the United States, and over 89,000 new cases are reported annually. Strikingly, many of these patients do not exhibit other signs of cardiovascular disease. Episodes of PSVT can be induced by various factors, including physical and psychological stress, infection, anemia, menstruation, and pregnancy (Lee, et al., *Curr. Probl. Cardiol.*, 2008, 33:467-546).

Atrial fibrillation (AF or A-fib) is an irregular and often rapid heart rhythm, or cardiac arrhythmia, that can lead to blood clots in the heart. Atrial fibrillation increases the risk of stroke, heart failure and other heart-related complications.

During atrial fibrillation, the heart's upper chambers, the atria, beat chaotically and irregularly—out of sync with the lower chambers, the ventricles, of the heart. Atrial fibrillation may cause a fast, pounding heartbeat or palpitations, shortness of breath, weakness, dizziness, chest pain, and/or exhaustion.

Atrial fibrillation may be occasional, with symptoms coming and going, usually lasting for a few minutes to hours. Symptoms may occur for as long as a week and episodes may happen repeatedly. Atrial fibrillation may also be persistent, with symptoms continuing until the patient is treated. Persistent atrial fibrillation may last for months, or even longer than a year.

Atrial fibrillation may be diagnosed through the use of electrocardiograms (ECG or EKG), blood tests, holter monitors, event recorders, echocardiograms, stress tests, and chest x-rays.

Angina

Angina, also known as angina pectoris, is a squeezing, pressure, heaviness, tightness or pain the chest, which may result from insufficient blood flow to the heart, for example. Other symptoms of angina include dizziness, fatigue, nausea, shortness of breath, and sweating. Angina may be stable or unstable. Stable angina is the most common form of angina, and may occur during exertion. Unstable angina may be a precursor to cardiac arrest. Other forms of angina include microvascular angina, Prinzmetal's angina, and variant angina.

Current Modes of Treatment

There is currently a lack of adequate treatment options for cardiac arrhythmia (e.g., PSVT or atrial fibrillation), angina, and/or migraine.

For example, while there are currently several therapeutic modalities available to PSVT patients, these platforms generally suffer from several deficiencies, chief among them being invasiveness or inefficiency. Patients can frequent the emergency room for immediate intervention during an episode, but this strategy provides only temporary relief. Such patients may continue to experience episodes of tachycardia throughout their lifetimes. Patients who suffer from chronic episodes of PSVT can have the nodal fibers that propagate anomalous action potentials ablated in order to permanently disrupt the mechanism that underlies the irregular cardiomyocyte contractions. This procedure typically requires that a catheter tube be inserted into the patient's femoral vein in order to access the heart, where a low-voltage pulse of electricity is delivered to the aberrant signaling tissue to map the reentry circuit. Aberrant nerve cells are ablated by cauterization with heat or cold. This process is highly invasive, and patients are often fearful of undergoing this form of treatment.

Alternatively, patients who suffer from chronic PSVT can take oral medication to help attenuate the severity or reduce the frequency of arrhythmia episodes. Calcium channel blockers and beta blockers represent classes of compounds that is functionally well-suited to ameliorate the symptoms of tachycardia, as these compounds are capable of reducing the influx of extracellular calcium into cardiomyocytes that ultimately leads to muscle contraction. Prevalent examples of calcium channel antagonists include verapamil and diltiazem, both of which are potent inhibitors of calcium influx and are widely used to treat PSVT. However, despite the widespread use of these therapeutics, patients who take these medications may continue to experience episodes of tachycardia.

The therapeutic product described in U.S. Pat. No. 10,117,848 may be self-administered in a single dose during an episode of PSVT in order to alleviate the symptoms during the episode. However, there is currently no commercially available therapeutic product that may be self-administered in a second dose during an episode of PSVT in order to alleviate symptoms not fully improved during a first dose of the therapeutic product.

The invention disclosed herein provides an innovative strategy for treating cardiac arrhythmias, such as PSVT, with a second dose of a therapeutic. The instant invention includes a novel method of two dose administration of a calcium channel blocker that enables the rapid delivery of the active compound into the bloodstream so as to reach maximum concentrations in plasma of PSVT patients within minutes of administration. Administration of a second dose facilitates the rapid termination of PSVT episodes not alleviated by one dose. The method of the present invention thus represents a new therapeutic paradigm for targeting faulty cardiac signaling in a precise and rapid fashion.

For another example, while there are currently several therapeutic modalities available to patients experiencing atrial fibrillation, these approaches generally suffer from several deficiencies, including time necessary to be evaluated for and prescribed an effective long-term medication, as well as treatment options for those experiencing occasional episodes of atrial fibrillation. Medications currently used to treat atrial fibrillation and related blood clots currently include beta blockers, calcium channel blockers, sodium channel blockers, potassium channel blockers, digoxin, digitalis, adenosine, antiplatelet drugs, and other anti-arrhythmic medications. What is needed for the treatment of atrial fibrillation is a composition for rapid delivery, which patients suffering from atrial fibrillation or medical personnel may easily carry in the case of atrial fibrillation onset in a patient not prescribed or not in the possession of a long-term treatment or when circumstances cause long-term treatment to fail, referred to as break-through.

The invention disclosed herein provides an innovative strategy for the treatment of patients experiencing atrial fibrillation episodes who are not yet following a consistent, long-term treatment, as well as the treatment of patients who experience occasional episodes of atrial fibrillation. In some embodiments, compound I (e.g., a formulation containing compound I) may be used as an adjunctive treatment to a typical anti-arrhythmic medication, such as a beta blocker, a calcium channel blocker, a sodium channel blocker, a potassium channel blocker, digoxin, digitalis, adenosine, or an antiplatelet drug. Beta blockers include acebutolol, metoprolol, nadolol, pindolol, betapace, propranolol. Calcium channel blockers include diltiazem and verapamil. Antiplatelet drugs include aspirin, anagrelide, dipyridamole, vorapaxar, apixaban, rivaroxaban, dalteparin, and fondaparinux.

Water Soluble Aqueous Salts

The acetate or methanesulfonate salt of Compound I is dissolved in aqueous solution and formulated for nasal administration. Nasal administration offers an advantage over oral administration in that the pharmaceutically active agent can rapidly traverse the nasal epithelium and immediately enter the bloodstream. In this way, once a therapeutically effective amount of the active compound is in the bloodstream, the compound can disrupt aberrant cardiac signaling in the anomalous cardiac fibers and provide a patient with relief from an episode of cardiac arrhythmia (e.g., PSVT or atrial fibrillation), stable angina, or migraine once it has started. After persisting in the blood for a time sufficient to restore proper cardiomyocyte activity, the compound is metabolized and deactivated in rapid fashion, so as to prevent prolonged cardiac exposure and harmful side effects.

Nasal administration requires a high concentration of an active compound due to the volumetric limit imposed by the nasal cavity. Administration of nasal sprays is typically limited to approximately 150 to 200 µL, beyond which point the liquid solution begins to enter the throat. This, in turn, imposes a limit on the quantity of a pharmaceutically active agent that can be delivered to the epithelial lining of the nasal cavity.

The inventors previously found that concentrated aqueous solutions of compound I could be made by treating the free base of this compound with acetic or methanesulfonic acid in order to produce acid addition salts. Methanesulfonic acid and acetic acid were capable of forming a salt solution with compound I with concentrations sufficient for nasal administration. For nasal administration, a desirable aqueous solution of compound I will exhibit a solubility of between approximately 150 mg/mL and 600 mg/mL, such as between approximately 300 mg/mL and 400 mg/mL or between approximately 325 mg/mL and 375 mg/mL (e.g., 150±25 mg/mL, 175±25 mg/mL, 200±25 mg/mL, 225±25 mg/mL, 250±25 mg/mL, 275±25 mg/mL, 300±25 mg/mL, 325±25 mg/mL, 350 mg/mL±100 mg/mL, 350 mg/mL±50 mg/mL 350±25 mg/mL, 350 mg/mL±10 mg/mL, 350 mg/mL±5 mg/mL, 375±25 mg/mL, 400±25 mg/mL, 425±25 mg/mL, 450±25 mg/mL, 475±25 mg/mL, 500±25 mg/mL, 525±25 mg/mL, 550±25 mg/mL, 575±25 mg/mL, or 600±25 mg/mL). Preferably, a desirable aqueous solution of compound I will exhibit a solubility between approximately 350 mg/mL±50 mg/mL. These concentrations correspond to a percentage of water of between 40% and 85% (w/v). The high solubility of the acetate and mesylate salts of compound I renders these salts uniquely suited for nasal administration, as the high concentrations of compound I attainable in these salt forms enable the delivery of a therapeutically effective amount of the compound within the volume limitation of the nasal cavity.

Figure 3:
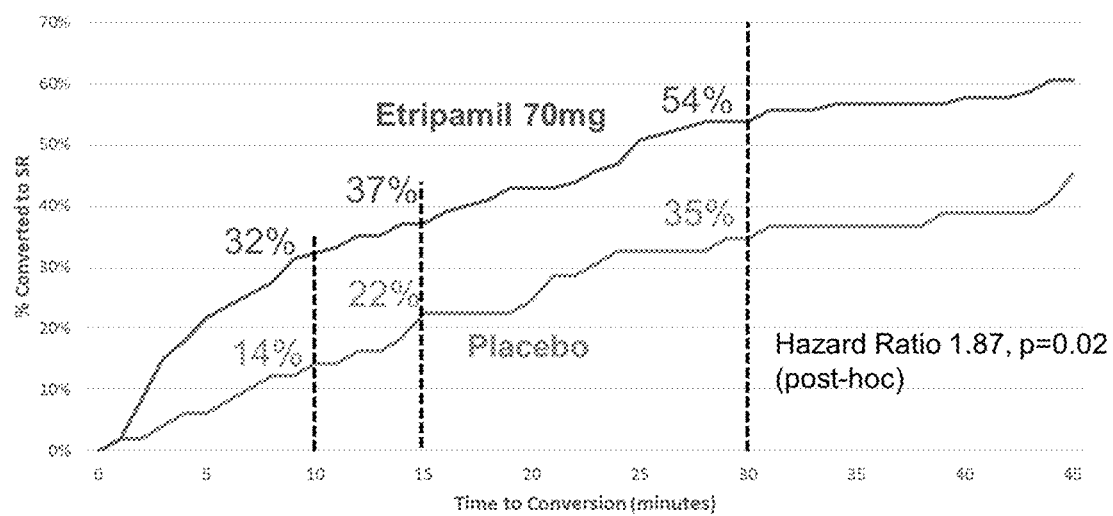
FIG. 3 is graph showing the percent conversion to sinus rhythm (SR) for compound I (etripamil) and placebo over time.

As seen in FIG. 3, as compared to the placebo, the strongest increase in patients converting to regular sinus rhythm may be seen in the first 10 minutes after administration of a first dose. Patients, e.g., ones with PSVT or a migraine, who are still experiencing symptoms, and therefore may, e.g., not have converted to normal rhythm, may take a second dose 5-25 minutes, (e.g., 6-22 minutes, 7-20 minutes, 8-16 minutes, or 10-14 minutes, such as, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 22 minutes, or 25 minutes) after the first dose. In one embodiment, the second dose is taken 10-15 minutes after the first dose. In one embodiment, the second dose is taken 10±2 minutes or 10±1 minute after the first dose. In one embodiment, the second dose is taken about 10 minutes after the first dose.

For other cardiac arrythmias, such as atrial fibrillation, it may be advantageous to administer the second dose 10, 25, 30, 40, 45, or 60 minutes after the first dose (e.g., between 5 and 25 minutes, 10 and 35 minutes, 25 and 45 minutes, or 45 and 60 minutes after the first dose.)

Preferable doses of compound I include doses that range from 15 mg to 140 mg of the active compound (e.g., 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, etc.). More preferable doses of compound I include doses that range from 60 mg to 80 mg of the active compound (e.g., 60 mg, 65 mg, 70 mg, 75 mg, or 80 mg) For example, a dose of compound I may be 70 mg±10%.

An aqueous solution containing the acetate or methanesulfonate salt of compound I exhibits a particular viscosity range. In certain embodiments, the viscosity of such a solution can range from 10 mPa*s to 70 mPa*s (e.g., 10 mPa*s, 15 mPa*s, 20 mPa*s, 25 mPa*s, 30 mPa*s, 35 mPa*s, 40 mPa*s, 45 mPa*s, 50 mPa*s, 55 mPa*s, 60 mPa*s, 65 mPa*s, or 70 mPa*s). For example, a solution containing a salt of compound I at a concentration of 315 mg/mL exhibited a viscosity of between about 16.515 mPa*s to about 37.505 mPa*s. In another example, a solution containing a salt of compound I at a concentration of 360 mg/mL exhibited a viscosity of between about 25.645 mPa*S to about 63.105 mPa*s.

Due to the formulations described herein, the patient experiences relief from an episode of PSVT very soon after administration of compound I, and because of the ideal pharmacokinetic profile of compound I, the drug does not persist in the bloodstream long enough to induce prolonged adverse side effects.

Permeation Enhancer

In order to exhibit an ideal pharmacokinetic profile, a pharmaceutically active compound or pharmaceutically acceptable salt thereof may be formulated with a material capable of enhancing the permeability of the active agent. In the formulation of the present invention, compound I will ideally enter the bloodstream rapidly (e.g., within 3 to 5 minutes of administration to a patient).

In a preferred embodiment of the present invention, the permeation enhancer of the instant formulation is a chelating agent. More preferably, the chelating agent is capable of coordinating divalent calcium ions ($Ca^{2+}$). It has been shown that the epithelial cells of mucous membranes are held in close contact by the formation of tight junctions. The paracellular transport of a pharmaceutically active compound through the epithelium requires that the compound penetrate these intercellular junctions. Transcellular transport, the alternative to paracellular transport, requires that a compound penetrate the epithelium by traversing the apical and basolateral membranes, a process for which many molecules are not well-suited due to their large molecular volumes. Chelating agents render paracellular transport possible, however, by binding and sequestering intracellular calcium (Cassidy, et al., *J. Cell Biol.*, 1967, 32:685-698). Calcium is essential to the biogenesis of tight junctions between epithelial cells, and the reduction of intracellular calcium compromises the integrity of these junctions and enables certain molecules to penetrate the intercellular volume between neighboring cells.

Exemplary chelating agents capable of coordinating calcium ions include aminopolycarboxylic acids. These include, without limitation, iminodiacetic acid (IDA), nitrilotriacetic acid (NTA), pentetic acid (DTPA), ethylenediaminetetracetic acid (EDTA), ethylene glycol tetraacetic acid (EGTA), (1,2-bis(o-aminophenoxy)ethane-N,N,N',N'-tetraacetic acid) (BAPTA), 1,4,7,10-tetraazacyclododecane-1,4,7,10-tetraacetic acid (DOTA), and N—(N-(3-amino-3-carboxypropyl)-3-amino-3-carboxypropyl)azetidine-2-carboxylic acid (nicotianamine), among others. In a preferred embodiment, the chelating agent is EDTA.

Despite the use of chelating agents such as EDTA to increase the permeation capacity of drugs through epithelial tissue, it was nonetheless surprising that the use of EDTA in the instant formulation increased the permeation of compound I through the nasal epithelium. The nasal vestibule, which accounts for approximately 3-4% of the surface area of the nasal cavity, lacks tight junctions altogether and is thus not affected by calcium chelating agents. EDTA has been shown to modulate tight junction formation, but even when junctions are compromised, the intercellular pores in the nasal epithelium are particularly small. As such, it has been postulated that the nasal epithelium is not susceptible to permeability modulation by EDTA (Aungst, et al., Pharma. Res., 1998, 5:305-308). Additionally, the ability of EDTA to increase permeation of a compound through the nasal epithelium is attenuated as the molecular weight of the compound increases (Nakanishi, et al., Chem. Pharm. Bull., 1984, 32:1628-1632).

pH Adjusting Agents

In certain embodiments of the invention, it is desirable to adjust the pH of the aqueous solution including a pharmaceutically acceptable salt of compound I. The pH of the formulation can be adjusted by treating the aqueous solution including a salt of one of these compounds with a solution including an acidic or a basic reagent. In preferred embodiments, the pH of the formulation is adjusted by titration of the aqueous solution with a solution including an acid. The pH of the formulation is desirably between 3.5 and 5.5, (e.g., 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, or 5.5), and is most desirably 4.5±0.1. The pH of the formulation can be adjusted by adding an aqueous solution containing an acid to the formulation so as to lower the pH to an ideal value. Exemplary acids that can be used to titrate an aqueous solution containing a salt of compound I include, without limitation, acetic acid, sulfuric acid, and methanesulfonic acid. In preferred embodiments, the acid used to adjust the pH of the formulation is sulfuric acid or methanesulfonic acid.

Additional Excipients

Formulations of the instant invention may include other agents capable of increasing the permeation, solubility, stability, or efficacy of compound I. Pharmaceutically acceptable excipients may include antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol. Additional excipients may include, without limitation, polysorbate, propylene glycol, hydroxypropyl β-cyclodextrin, triethylcitrate, benzalkonium chloride, and N-dodecyl-β-D-maltoside.

The formulation of the present invention may optionally include a pharmaceutically acceptable carrier. Examples of a pharmaceutically acceptable carrier include, without limitation, a preservative, antioxidant, fragrance, emulsifier, dye, or excipient known or used in the field of drug formulation and that does not significantly interfere with the therapeutic effectiveness of the biological activity of the active agent, and that is non-toxic to the patient.

Nasal Delivery System

The present invention additionally provides a nasal delivery system for the administration of aqueous solutions of salts of a compound described herein, such as compound I, to the nasal cavity of a patient suffering from cardiac arrhythmia (e.g., PSVT or atrial fibrillation), stable angina, or migraine. The nasal delivery system of the invention includes an aqueous solution of the acetate or methanesulfonate salt of compound I, in a unit dosage form. This solution may additionally contain other materials, including, without limitation, a permeation enhancer, pharmaceutically acceptable excipient, and/or a pH adjusting agent. The nasal delivery system includes the unit dosage form as a pump spray dosage. In this way, the nasal delivery system can be used to administer an aqueous solution containing the acetate or methanesulfonate salt of compound I into the nasal cavity of a patient during an episode of cardiac arrhythmia (e.g., PSVT or atrial fibrillation), stable angina, or migraine. At the onset of an episode, a patient can easily self-administer this formulation containing one of these active compounds by inserting the applicator of the nasal delivery system into the nostril and applying compressible pressure to the pump of the system. This will trigger the release of a spray including the aqueous solution of a salt of the active compound into the nasal cavity and onto the nasal epithelium.

The nasal delivery system is analogous to nasal delivery systems that are commercially available, such as those used to deliver such drugs as Imitrex® (sumatriptan), sold by GlaxoSmithKline (Brentford, UK), Zomig® (zolmitriptan), sold by Impax Pharmaceuticals (Hayward, CA, USA), and Spravato® (esketamine), sold by Janssen (Beerse, BE). These systems include a vial, a piston, a swirl chamber, and an actuator. Upon applying pressure to the actuator, the liquid is forced through the swirl chamber and released as a spray. These nasal delivery systems often include a pressure point mechanism to ensure that a reproducible pressure is applied to the system in order to achieve release of a consistent volume of spray (Rapoport, et al., *Headache*, 2006, 46:S192-S201). The nasal delivery system of the invention includes a unit dosage form that contains no more than four (e.g., one, two, three, or four single pump spray dosages. In alternative embodiments, the unit dosage form includes no more than two (e.g., one or two) single pump spray dosages. The unit dosage form can be configured for delivery of no more than 200 μL (e.g., 200 μL, 190 μL, 180 μL, 170 μL, 160 μL, 150 μL, 140 μL, 130 μL, 120 μL, 110 μL, or 100 μL) of the aqueous solution including a salt of compound I. In alternative embodiments, the unit dosage form is configured for delivery of no more than 150 μL (e.g., 150 μL, 140 μL, 130 μL, 120 μL, 110 μL, or 100 μL) of the aqueous solution including the acetate or methanesulfonate salt of compound I.

EXAMPLES

In order that this invention be more fully understood, the following examples are set forth. These examples are for the purpose of illustration only and are not to be construed as limiting the scope of the invention in any way.

Figure 4:
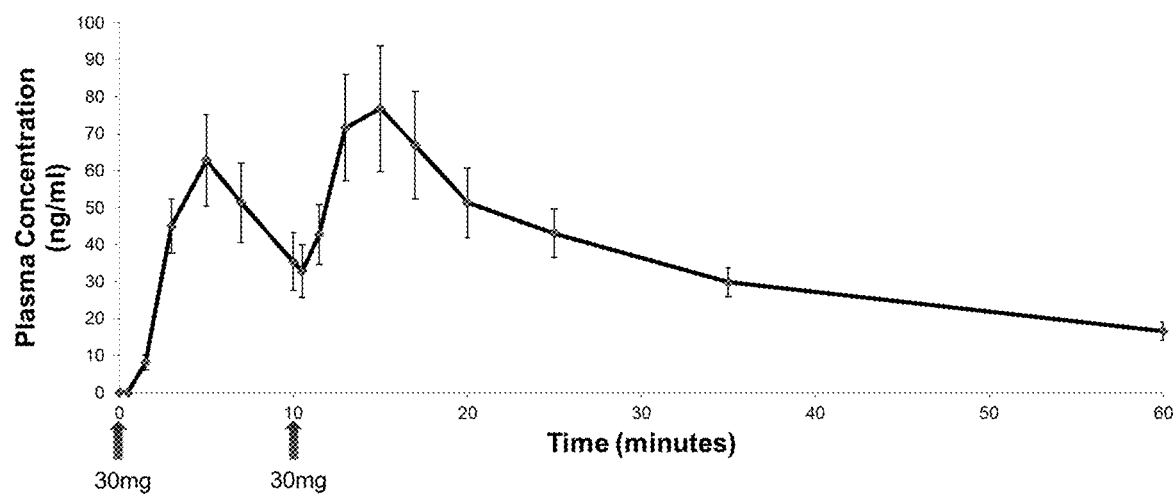
FIG. 4 is graph illustrating an increase in the plasma concentration following both a first and second dose of 30 mg of compound I.

Example 1: Two 30 mg Dose Nasal Administration of Compound I 30 mg of the acetate salt of compound I were nasally administered to healthy volunteers, and ten minutes later, a second 30 mg dose was nasally administered. The acetate salt of compound I administered in this way reaches a maximum concentration in plasma within 3 to 5 minutes after administration to the subject, as seen in FIG. 4, and minimal concentrations of the compound in plasma are observed within 50 to 60 minutes of administration. Repeat administration increases both Cmax and area under the curve (AUC).

Example 2: One 70 mg Dose Nasal Administration of Compound I for Treatment of PSVT Rationale for Dosing In a Phase 1 study, compound I 140 mg was determined to be the MFD (maximum feasible dose) with the current formulation based on the maximal concentration of compound I and the required volume of administration (up to 200 μL of the solution) in each nostril. The 4 highest doses tested in Phase 1 (30, 60, 105, and 140 mg) produced an increase in the PR interval of the ECG that was consistent with the necessary PD effect required to convert reentry tachycardia involving the AV node to SR. Previous published data indicate that a PR prolongation of approximately 8 to 10% appears to be a pharmacodynamic marker associated with the conversion of PSVT to normal sinus rhythm (Reiter, 1982; Prystowsky, 2003). One of the cohorts evaluated the effects of two 30 mg doses given 10 minutes apart and demonstrated that drug exposure and PR interval increased and remained elevated for a longer period as compared to the single 30 mg dose.

Randomized, double-blind, placebo-controlled, ethno-bridging PK/PD study, 35, 70 and 105 mg doses were evaluated. Compound I (etripamil) exposure increased in a dose proportional manner between 35 and 70 mg but not between the 70 and 105 mg doses. Inter-patient variability and a correlation with height were observed. The PR interval and HR were increased within 10 minutes and correlated to PK parameters. The pharmacodynamic effect of compound I began to decrease starting at 15 minutes and lasted for up to 30-45 minutes based on the duration of PR prolongation exceeding 10% from baseline.

In Phase 1 studies, an increase in Treatment Emergent Adverse Effects (TEAEs), mainly related to nasal irritation, was observed at doses higher than 70 mg.

In a Phase 2 study, four doses (35, 70, 105, and 140 mg) were tested. The 3 highest doses (70, 105, and 140 mg) were statistically significantly superior compared with placebo for terminating induced PSVT within 15 minutes of dosing; in addition, the time to conversion of PSVT to sinus rhythm (SR) was shorter with these doses compared with placebo. The Emax model of dose response indicates that these 3 doses are at the plateau of the dose response, whereas the 35 mg dose is in the ascending portion of the curve.

A drop in systolic blood pressure (SBP) versus baseline was observed with the 105 and 140 mg doses between 4 and 10 minutes after compound I administration, with mean reductions of 11.4% (105 mg), and 15.6% (140 mg) mmHg. Mean SBP did not drop following administration of compound I at doses of 35 and 70 mg.

Compound I 35 mg had an overall success rate of 65% at 15 minutes compared to 35% with the placebo. The treatment effect of 30% compared to the high efficacy rates of existing therapies renders the 35 mg dose inadequate as a development candidate.

Compound I NS 70 mg satisfies the need to balance benefit and risk. The required delivery dose (70 mg) is well tolerated; efficacy (measured in PSVT termination rate) is at the plateau of the dose response curve; and the AE profile is acceptable, with no post-dose reductions observed in SBP in contrast to the 2 higher doses.

For these reasons, compound I NS 70 mg was selected as the only dose for a Phase 3 study.

Study Design

A multi-center, randomized, double-blind, placebo-controlled study to evaluate the efficacy and safety of a 70 mg self-administered dose of compound I in an at-home setting was conducted. The study included 431 patients enrolled (completed a test dose), 419 patients randomized into the study, and 156 randomized patients presenting with a positively adjudicated episode of PSVT for the pivotal analysis. PSVT episodes were documented by an ambulatory Cardiac Monitoring System (CMS) placed on the chest by the patient or caregiver when symptoms began and were recorded at least 5 hours of continuous electrocardiogram (ECG).

The primary efficacy endpoint was defined as an adjudicated termination of a positively adjudicated episode of PSVT and conversion to sinus rhythm for at least 30 seconds. The primary efficacy endpoint was evaluated using the time to conversion of an episode of PSVT to sinus rhythm after study drug administration as the primary efficacy variable. The study included a screening visit, a test dose randomization visit, follow-up visits, a treatment period, and a final study visit. Before randomization, all patients received a 70 mg test dose of compound I to evaluate tolerability. The test dose administration took place at the study site under medical supervision while the patient was in sinus rhythm (SR). Patients who passed the test dose were randomized in a 2:1 ratio to 70 mg compound I or placebo. During the treatment period, all randomized patients performed a sequence of steps upon self-identifying symptoms of an episode of PSVT, including contacting a telephone coach for assistance on study procedures, applying a CMS on their chest, performing a vagal maneuver (VM), and study drug self-administration.

For administration, the patients placed the applicator of the system into their nose. The subject's held the nasal delivery system between the second and third fingers, with the thumb placed on the actuator. This process was similar to the use of commercially available nasal delivery systems such as those used to deliver such drugs as Imitrex® (sumatriptan), sold by GlaxoSmithKline (Brentford, UK), Zomig® (zolmitriptan), sold by Impax Pharmaceuticals (Hayward, CA, USA), and Spravato® (esketamine), sold by Janssen (Beerse, BE). The subjects then apply pressure to the actuator, which forces the liquid solution containing the dissolved acetate salt of compound I through the device, causing the solution to be released from the tip of the applicator as a spray. The solution was administered to the patients as two single pump spray dosages in order to deliver 70 mg of compound I to the nasal epithelium.

The spray administered as described delivered the solution containing the acetate salt of compound I to the nasal epithelium, wherein compound I penetrated the epithelium and rapidly entered the bloodstream. The acetate salt of compound I administered in this way reached a maximum concentration in plasma within 3 to 5 minutes after administration to the patient, and minimal concentrations of the compound in plasma were observed within 50 to 60 minutes of administration.

The presence of an episode of PSVT and termination were evaluated by an independent Adjudication Committee. The Adjudication Committee's evaluations were done using the complete CMS ECG recorded during the patient's PSVT episode.

Results

At the completion of the study, 419 out of 431 patients (97%) who received the test dose were randomized into the study. 198 patients self-administered the study drug for a perceived episode of PSVT of which 156 patients (79%) had positively adjudicated PSVT episodes; 107 (68.6%) patients received compound I and 49 (31.4%) patients received placebo. The study did not achieve its primary endpoint of time to conversion of PSVT to SR compared to placebo following compound I administration over the 5-hour observation period. The hazard ratio HR (95% CI) was 1.086 (0.726, 1.623); p=0.12 in favor of compound I. The median time to conversion was 25 minutes (95% CI: 16, 43) for compound I vs. 50 minutes (95% CI: 31,101) for placebo. Early drug effect was observed, including the conversion of 54% of compound I patients compared to 35% of placebo patients within 30 minutes after study drug administration (p=0.02), a time period consistent with pharmacological activity of compound I. Patients who received placebo went to the emergency department to receive rescue medication earlier and more often than those who received compound I, contributing to confound results from the latter time period of the statistical analysis of the primary endpoint at 5 hours.

Figure 2:
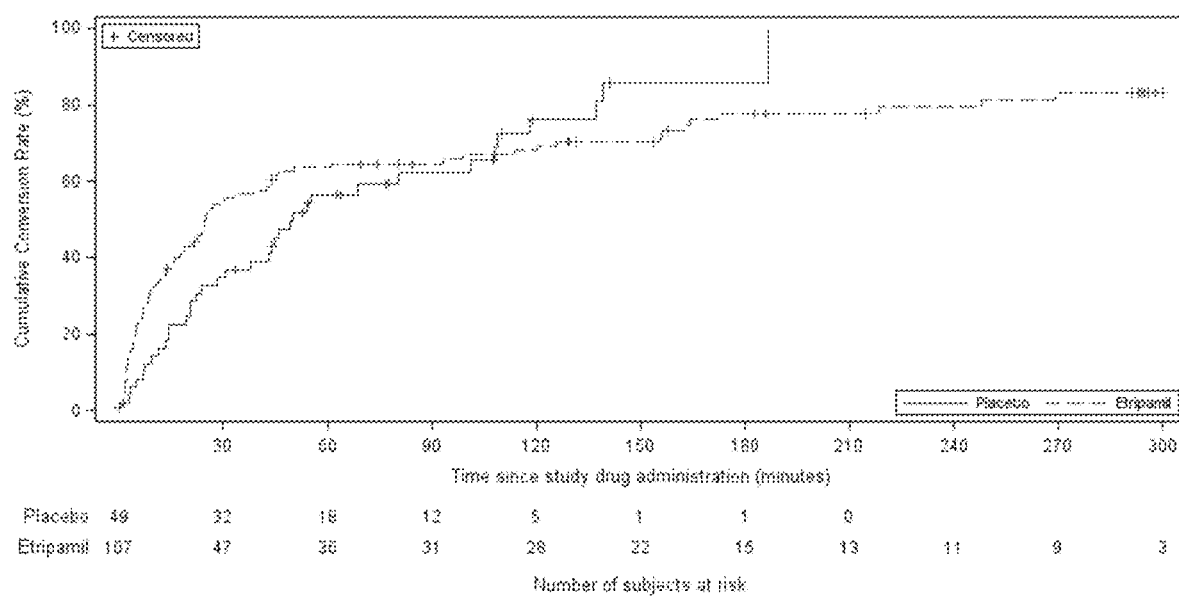
FIG. 2 shows a Kaplan-Meier plot of conversion up to 5 hours (efficacy population, primary analysis, primary endpoint). The solid line shows the data for the placebo and the dashed line shows the data for compound I (etripamil). The data for compound 1 extends to 300 minutes since study drug administration.

The study demonstrated nominal statistically significant improvements in favor of compound I over placebo in the secondary endpoint of patient reported treatment satisfaction, as measured by a treatment satisfaction questionnaire for medication (TSQM-9), including overall satisfaction and effectiveness scores, with questions addressing the relief of symptoms commonly associated with an episode of PSVT, such as rapid pulse, heart palpitations, anxiety, shortness of breath, and dizziness. FIG. 2 shows a Kaplan-Meier plot of conversion up to 5 hours (efficacy population, primary analysis, primary endpoint).

The most common adverse events observed in patients receiving compound I were local to the nose, including nasal irritation and congestion; these events were more frequent in the compound I group, typically transient in nature and most commonly characterized by the patient as mild in severity. There were no significant differences in incidences of severe adverse events or adverse events of interest, such as atrioventricular nodal blocks or blood pressure-related symptoms, across the compound I and placebo groups.

The primary objective of this study was to determine whether compound I NS is superior to placebo at rapidly terminating acute episodes of PSVT in an at-home setting. Therefore, a double-blind, placebo-controlled, parallel design study was the most appropriate to reach the objective.

Compound I addresses an unmet medical need since there are currently no short-acting products available for patient self-administered treatment of acute episodes of PSVT. The only currently available acute pharmacological therapy is IV treatment with adenosine or verapamil in a hospital environment, which is expensive and greatly inconveniences the patient. A self-administered product for acute PSVT would give patients the option to safely terminate acute episodes of PSVT without the need for a hospital visit. An episodic treatment option would also allow selected patients to discontinue chronic prophylactic therapy with Class I, II (e.g., beta-blockers), III, and/or IV (e.g., calcium channel blockers) antiarrhythmic agents, thus avoiding the side effects and quality of life implications associated with these medications. Furthermore, patients weighing the risks of bridging therapy and an invasive catheter ablation procedure to address their PSVT would have the opportunity to consider episodic management with compound I as a viable alternative treatment option.

The nonclinical safety program and clinical studies continue to demonstrate that compound I, overall, displays a favorable safety profile. No important risks for compound I have been identified during the compound I development program. The important potential risks for compound I are cardiac effects (second- or third-degree atrioventricular (AV) block, sinus pauses ≥3 sec, sinus bradycardia, and exacerbation of congestive heart failure), syncope, symptomatic hypotension and hypersensitivity reactions.

The goal of this double-blind study was to demonstrate the safety and effectiveness of compound I NS in the treatment of spontaneous episodes of PSVT when self-administered by patients in an at-home setting.

Example 3: Two 70 mg Dose Nasal Administration of Compound I in Patients for Treatment of PSVT Background Compound I, an L-type calcium channel antagonist and short-acting verapamil analog, is being developed for the treatment of paroxysmal supraventricular tachycardia (PSVT), hereinafter used in reference to both the disorder and its associated tachyarrhythmia. A relatively common disorder, PSVT is characterized by episodes of tachyarrhythmia typically with a heart rate (HR) over 100 bpm and a QRS duration of <120 msec. Compound I is directed towards the 2 most common subtypes of PSVT, atrioventricular (AV) nodal reentrant tachycardia (AVNRT) and AV reentrant tachycardia (AVRT), together accounting for approximately 90% of PSVT cases. In both conditions, a pharmaceutical agent capable of transiently prolonging AV conduction time can result in arrhythmia termination and restoration of normal sinus rhythm (SR).

Historically, intravenous (IV) verapamil has been used as an effective agent for treatment of acute episodes of PSVT. However, it has been replaced in recent years by IV adenosine, which is equally effective in terminating acute episodes of PSVT. Adenosine has the advantage of having a very short half-life, as it is rapidly metabolized during the time required to terminate an episode of PSVT. However, the short half-life of adenosine renders it ineffective when given via routes of administration other than IV. As both of these medications require the establishment of IV access, they are not appropriate for a patient self-administration paradigm in an at-home setting.

Rationale for Dosing

A post hoc efficacy analysis of the study of Example 2 demonstrated early compound I activity, with a conversion rate of 54% of compound I patients vs. 35% of placebo patients converted to SR by 30 minutes after drug administration, i.e., approximately a 19% absolute difference, consistent with a rapid onset of action, similar to what was observed in Phase 2 and consistent with the PK of the drug. The study also showed that treatment with a 70 mg dose was safe and well tolerated over 5 hours following treatment in more than 100 patients in PSVT.

These clinical data led to the adoption of a new dosing regimen for the present study in an attempt to increase the exposure and pharmacodynamic effect of compound I. This dosing regimen allows patients to receive a second dose of compound I nasal spray (NS) 70 mg 10 minutes after the first dose if the symptoms of PSVT persist, thus administering a total of 140 mg compound I NS only to patients who do not respond to compound I NS 70 mg at 10 minutes. In addition, the split-dose regimen reduces the volume of spray administered at one time in the nasal cavity, compared to what would be required to administer a higher dose of drug via a single spray. This is referred to herein as the RAPID study.

Objectives

The primary objective of this study is to determine whether a two dose administration of nasal spray (NS) comprising compound I self-administered by patients is superior to placebo at terminating episodes of PSVT in an at-home setting. The secondary objective of this study is to evaluate the safety of compound I when self-administered twice by patients without medical supervision. The exploratory objectives of the study are: to evaluate the safety, hemodynamic, and cardiac conduction effects of a test dose of compound I NS, to evaluate the safety and efficacy of compound I NS in various subgroups of interest (e.g., concomitant medications), and to evaluate the safety and efficacy of a treatment regimen of compound I NS which allows a repeat dose of compound I to terminate episodes of PSVT in an at-home setting.

Formulation

The formulation of the composition will consist of compound I, water, acetic acid, disodium ethylene-diamine-tetra-acetic acid (EDTA), and sulfuric acid. The dose of compound I to be evaluated in the RAPID study is 70 mg per nasal spray device, using the dosing regimens described previously. The same formulation will be used for the Test Dose Randomization Visit and for the Treatment Periods. The formulation of placebo will consist of water, sodium acetate, disodium EDTA, and sulfuric acid to reproduce the same pH as the compound I formulation. Each nasal spray device delivers a total of 200 µL of compound I NS 70 mg or placebo (i.e., 100 µL in each nostril via the Aptar Pharma Nasal Spray Bidose System [BDS]). The devices will be prefilled and packaged into child-resistant boxes. Instructions for its use are provided in the Manual of Operations and Procedures (MoOP) and will be provided in the study drug box.

The population for this study is patients at least 18 years of age who have electrographically documented history of PSVT with a history of sustained episodes (i.e., typically lasting approximately 20 minutes or longer).

Study Design

Figure 1:
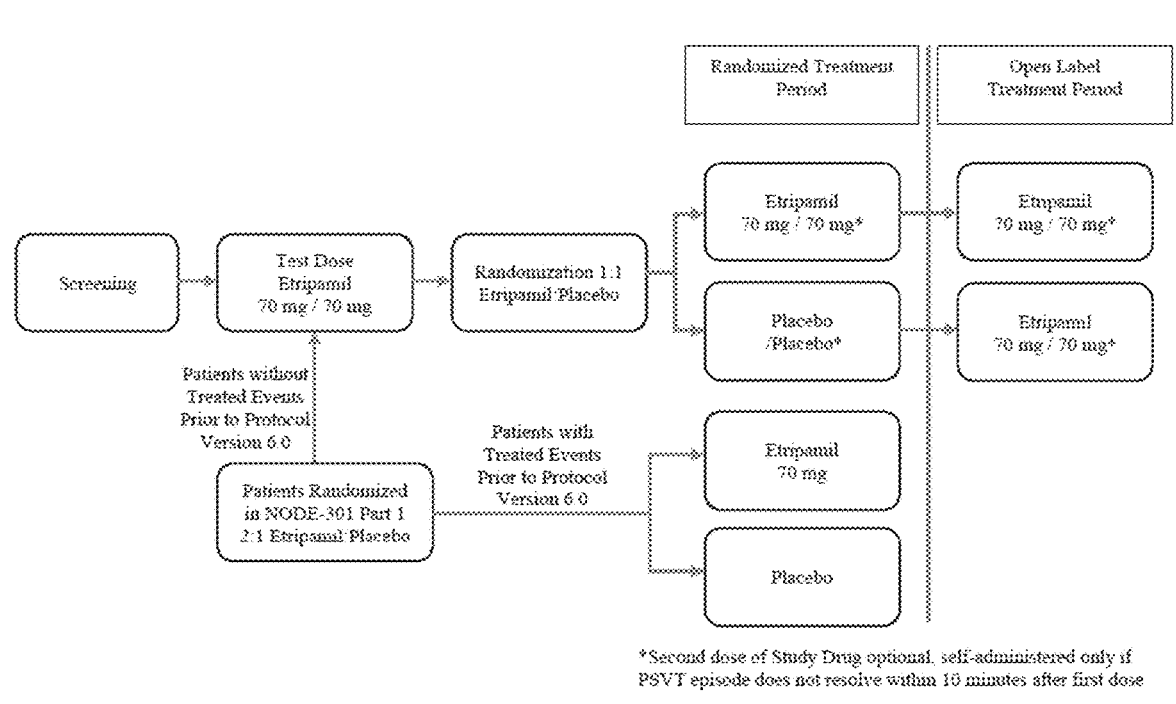
FIG. 1 shows a study design for a clinical trial of a two dose regimen of compound I.

The study design may be seen in FIG. 1. The study will consist of a screening visit, a test dose randomization visit, monthly follow-up visits, a Randomized Treatment Period, a randomized treatment period follow-up visit, an Open-label Treatment Period, and a final study visit.

Inclusion criteria included male or female patients at least 18 years of age having electrographically documented history of sustained episodes of PSVT (e.g., electrocardiogram [ECG] obtained during an episode of PSVT, Holter monitoring, loop recorder, etc.), with the episodes typically lasting approximately 20 minutes or longer. If patient had a prior ablation for PSVT, patient must have documented ECG evidence of PSVT post-ablation. Females of childbearing potential who are sexually active must agree to use an approved highly effective form of contraception from the time of signed informed consent until 30 days after the last administration of study drug. Females of childbearing potential should have a negative serum pregnancy test result at the Screening Visit and at the Final Study Visit, a negative urine pregnancy test at the Test Dose Randomization Visit and must use an approved form of contraception between the visits. Approved forms of contraception include hormonal intrauterine devices or hormonal contraceptives (oral birth control pills, patch, or other injectables) together with supplementary double-barrier methods, such as condoms or diaphragms with spermicidal gel or foam. Premenopausal women with documented hysterectomies, documented bilateral salpingectomy or tubal ligation, or documented bilateral oophorectomy are not considered to be of childbearing potential. Premenopausal females who are sexually active with a partner who is surgically sterile, i.e., vasectomy, or are defined as having amenorrhea for at least 12 months without an alternative medical cause are also considered to not be of childbearing potential. Male patients, except those who are surgically sterile, must use an approved highly effective form of contraception during the 3 days after any study drug administration. Signed written informed consent is required.

Exclusion criteria includes anyone having a history of severe symptoms of hypotension, especially syncope, during episodes of PSVT; history of allergic reaction to verapamil; history of atrial arrhythmia that does not involve the atrioventricular (AV) node as part of the tachycardia circuit (e.g., atrial fibrillation, atrial flutter, intra-atrial tachycardia); systolic blood pressure (SBP)<90 mmHg after a 5-minute rest in sitting position at the Screening Visit or before the test dose. In patients treated with a chronic prophylactic drug for PSVT (e.g., beta-blockers, verapamil, and diltiazem), the drug may be stopped for at least the equivalent of 5 half-lives and patients may be rescreened once; current therapy with digoxin or any Class I or III antiarrhythmic drug, except if these drugs are stopped at least the equivalent of 5 half-lives before the Test Dose Randomization Visit; current therapy with amiodarone, or have taken amiodarone within 30 days prior to the Test Dose Randomization Visit; evidence of ventricular pre-excitation (e.g., delta waves, short PR interval<100 msec, Wolff-Parkinson-White syndrome) on the ECG performed at the Screening Visit or before the test dose administration; evidence of a second- or third-degree AV block on the ECG performed at the Screening Visit or before the test dose administration; history or evidence of severe ventricular arrhythmia (e.g., Torsades de Pointes, ventricular fibrillation, or sustained ventricular tachycardia); current congestive heart failure defined by the New York Heart Association Class II to IV; stroke in the last 6 months; evidence of hepatic dysfunction defined as alanine aminotransferase or aspartate aminotransferase>3× the upper limit of normal (ULN) or total bilirubin>2×ULN at the Screening Visit, unless due to Gilbert syndrome; evidence of renal dysfunction as determined by an estimated glomerular filtration rate assessed at <60 mL/min/1.73 m2 for patients<60 years of age, <40 mL/min/1.73 m2 for patients≥60 and <70 years of age, or <35 mL/min/1.73 m2 for patients≥70 years of age females who are pregnant or lactating; participation in any investigational drug or device study or the use of any investigational drug or device within 30 days of the Screening Visit; Previously enrolled in a clinical trial for compound I and received study drug during a perceived episode of PSVT; evidence or history of any significant physical or psychiatric condition including drug abuse, which, in the opinion of the Investigator, could jeopardize the safety of patients or affect their participation in the study. Additionally, the Investigator has the ability to exclude a patient if for any reason the Investigator judges the patient is not a good candidate for the study or will not be able to follow study procedures.

During the Screening Visit, the Investigator will review the patient's medical history and complete assessments to confirm eligibility, including confirmation of PSVT. Investigators will be provided with a MoOP that will define acceptable source documents required to confirm the PSVT diagnosis. The Investigators will enroll patients who have a history of sustained episodes of PSVT (i.e., typically lasting approximately 20 minutes or longer). As stated above, females of childbearing potential and male patients, except those who are surgically sterile, who are sexually active must agree to use an approved highly effective form of contraception. Prospective study patients will be asked to sign the informed consent form before the commencement of any study-related assessments or procedures. Once the informed consent is signed, patients will be considered enrolled in the study. If an enrolled patient meets at least 1 of the exclusion criterion listed above, the patient will be considered a screening failure. Re-screening may be allowed after consultation between the Investigator and Medical Monitor.

Before randomization in the RAPID study, all patients will receive a test dose of a compound I NS dosing regimen (an initial dose of compound I NS 70 mg followed by a second dose of compound I NS 70 mg not earlier than 10 minutes and not later than 15 minutes after the first dose) under medical supervision to evaluate tolerability and to train patients on the study procedures. Both doses of the compound I dosing regimen must be administered for the test dose to be considered evaluable. A failure of the test dose is considered if patients meet any of the criteria occurring after administration of the compound I NS 70 mg test dose including: any symptoms consistent with clinically severe hypotension such as pre-syncope, medically significant lightheadedness, syncope, nausea, or vomiting; for patients with a pre-test dose SBP above 100 mmHg, decrease in SBP≥40 mmHg after test dose, or post-test dose SBP<80 mmHg; for patients with a pre-test dose SBP between 90 mmHg and 100 mmHg (inclusive) a post-test dose SBP<75 mmHg; third-degree AV block, Mobitz II second-degree AV block, or Wenckebach with bradycardia≤40 bpm; new, significant sinus bradycardia heart rate (HR)≤40 bpm or sinus pauses (≥3 seconds), if considered by the Investigator to put the patient's safety at risk if either were to occur while not under medical supervision; any new ventricular arrhythmia considered significant by the Investigator; atrial fibrillation, atrial flutter or atrial tachycardia (event lasting longer than 30 seconds); or refusal of second dose of compound I test dose regimen.

Patients who pass the test dose of the compound I NS dosing regimen, as described above, will be randomized to in a 1:1 ratio to compound I or placebo using an Interactive Response Technology (IRT) system. If the CMS ECG test dose report is delayed for any unforeseen reason, patients will be allowed to leave and return to the site another day for randomization.

Patients who fail the test dose will proceed in the study as follows. If the Investigator identifies a possible reversible cause of the initial test dose failure (e.g., concomitant medication such as beta-blocker), a re-challenge with a new test dose of compound I dosing regimen within a 14-day window from the initial test dose will be possible after elimination of the reversible cause (e.g., withdrawal of concomitant therapy with the appropriate washout period). Patients may be randomized if they pass the second test dose, and the cause of the test dose failure is eliminated for the duration of the study. If the Investigator cannot identify a reversible cause of the initial test dose failure, or if the potential cause cannot be modified (e.g., necessary antihypertensive drug to control blood pressure), patients will not be randomized and will complete a Final Study Visit. Patients who fail the test dose will be part of the Test Dose Only Population, including all patients who received at least 1 test dose of compound I NS 70 mg.

The interpretation of the CMS ECG will be provided by the cardiac monitoring core laboratory to the site in a report based on the mobile system's proprietary arrhythmia detection algorithms and automatic ECG collection. During each patient's Test Dose Randomization Visit, the cardiac monitoring core laboratory will generate a summary test dose report within approximately 1 to 2 hours of the receipt of the ECG data. This report will be used by the site to determine if the patient passes or fails the test dose and if the eligibility criteria to be randomized in the study have been met. The operational aspects of the use of the CMS during the test dose are described in the MoOP.

Randomized patients will be trained on how to report AEs to the sites during the study for evaluation and on specific procedures to be followed when they experience an episode of PSVT, including how to identify and report PSVT symptoms, contact the Telephone Coach (if possible), set up and use the CMS, perform a vagal maneuver (VM), and self-administer study drug. A caregiver may help the patient with these procedures, and this should be annotated in the electronic case report form (eCRF). Each randomized patient will receive a study kit, which includes the blinded study drug (2 devices pre-filled with placebo or compound I NS 70 mg), a CMS, a study identification card, patient's study instructions, and other study-related material. Randomized patients will also be provided with patient questionnaires to be completed after experiencing a PSVT episode. The patient questionnaires collect information about the timing and symptoms of the patient's PSVT episode and includes a Treatment Satisfaction Questionnaire for Medication (TSQM-9). Standardized training will be described in the MoOP.

The study will consist of patients who were not dosed with the double-blind study drug or have not discontinued the study before the adjudication of the 150th positively adjudicated PSVT episode, and patients enrolled into the study following the completion of the study of Example 2.

Enrollment into the study will continue until the adjudication of the 180th positively adjudicated PSVT episode of patients treated with double-blind study drug during the Randomized Treatment period required for the study's pivotal analysis. The study will continue for approximately 6 months after the date of the adjudication of the 180th positively adjudicated PSVT episode. All patients not unblinded as part of the pivotal analysis will be unblinded at the end of the study.

Prospective study patients will be asked to sign the informed consent form before the commencement of any study-related assessments or procedures. Once the informed consent is signed, patients will be considered enrolled in the study. For newly enrolled patients the initial Test Dose Randomization Visit for newly enrolled patients must occur within 28 days after the Screening Visit. For patients previously enrolled in the study of Example 2, a Test Dose Randomization visit to assess the safety of a second dose of compound I NS 70 mg is required. Before randomization, all patients will receive a test dose of compound I NS 70 mg to evaluate tolerability and to train patients on the study procedures. All patients who pass the test dose of the compound I NS dosing new regimen will be given a study kit, including double-blind study medication to treat a PSVT episode in an at-home setting. Monthly follow-up visits will be conducted. These visits can be conducted by patients returning to the investigative site or by the site personnel contacting patients by telephone.

When randomized patients identify symptoms of an episode of PSVT, they will perform a sequence of steps, including placement of CMS device on his/her chest and study drug self-administration. A caregiver may help the patient with these procedures, and this should be annotated in the electronic case report form. Self-administration of the study drug regimen during a PSVT episode is as follows: an initial dose of compound I NS 70 mg (or placebo) followed by a second dose 10 minutes later if the patient continues to experience PSVT symptoms.

The steps of the procedures are the following. 1) Contact the Telephone Coach (if possible) who will guide the patient through the study procedures. If the patient is unable to reach the Telephone Coach, he/she may proceed with the procedures using the printed and electronic guides provided. 2) Apply the CMS to record cardiac activity. 3) Perform a VM. If the VM is successful in relieving symptoms, the patient will not self-administer study drug but will keep the CMS device on for 5 hours. The episode of PSVT and the results of the VM will be adjudicated, and the patient will remain in the study for a subsequent episode of PSVT. 4) Administer study drug if the symptoms do not resolve after completion of the VM. The patient will push the CMS event marker button to record the time of dosing immediately prior to self-administering each dose of study drug, as applicable. The CMS should not be removed, and the recording should continue for at least 5 hours after study drug administration; The patient should be seated prior to self-administering the first dose of study drug, (each dose consists of 2 sprays of study drug from a single device, one spray in each nostril). If symptoms of PSVT do not resolve within 10 minutes after the first dose of study drug, the patient should administer a second dose of study drug by using the additionally-provided nasal spray device. The second dose of study drug should be taken not earlier than 10, and not later than 15 minutes after the first dose. The patient may gently blow their nose to remove any excess fluid build-up immediately prior to self-administration of the second dose. The patient will push the CMS event marker button immediately prior to self-administering the second dose. In the event that a full dose (i.e., 2 sprays, one in each nostril) of study drug is not administered during the first dose (e.g., due to misuse of device or device malfunction), the patient should wait at least 10 minutes before self-administering a second dose, if needed. Patients should not self-administer a second dose of study drug if they are experiencing tolerability issues believed related to the first dose (e.g., symptoms of lightheadedness/dizziness). 5) Complete the provided patient questionnaires. Questionnaires regarding details of the PSVT episode being treated should be completed as soon as possible after dosing of study drug regimen is completed. Completion of TSQM-9 should be completed as soon as possible after termination of the treated PSVT episode. 6) If the symptoms of PSVT have not resolved within 30 minutes after the start of study drug administration, patients may seek appropriate medical care. When the patient reaches a medical care facility to seek treatment for the episode of PSVT, the patient must give the study identification card included in the study kit to the on-site medical personnel. The study identification card contains a brief description of the study, the Investigator and Medical Monitor contact information, and a short questionnaire to be filled out by the on-site physician to document the diagnosis of the episode, the treatment administered, and the outcome. The CMS should not be removed, and recording should continue for at least 5 hours after study drug administration. If unblinding is judged necessary by the on-site treating physician, a 24/7 assistance telephone number will be provided on the study identification card so that the situation can be discussed with the Medical Monitor. It is recommended to contact the study Medical Monitor before any unblinding occurs. 7) Schedule a Randomized Treatment Period Follow-Up Study Visit within 7 days of study drug administration.

A Randomized Treatment Period Follow-Up Visit will occur at the study site within 7 days after a patient self-administers study drug during the Randomized Treatment Period. Patients without tolerability issues will be entered into the Open-Label Treatment Period.

The interpretation of the CMS ECG will be provided by the cardiac monitoring core laboratory to the site in a report based on the mobile system's proprietary arrhythmia detection algorithms and automatic ECG collection. The cardiac monitoring core laboratory will generate a summary report within 48 hours of the receipt of ECG data. The operational aspects are described in the MoOP. These reports will be sent to the site and the Medical Monitor. In all double-blind cases, the presence of an episode of PSVT and termination will be evaluated by an independent Adjudication Committee. The Adjudication Committee's evaluations will be done using the complete CMS ECG recorded during the patient's PSVT episode.

For the Open-Label Treatment Period all patients will perform a sequence of steps, including compound I NS self-administration when patients identify symptoms of an episode of PSVT. A caregiver may help the patient with these procedures, and this should be annotated in the electronic case report form. 1) Contact the Telephone Coach (if possible) who will guide the patient through the study procedures. If the patient is unable to reach the Telephone Coach, he/she may proceed with the procedures using the printed and electronic guides provided. 2) Apply the CMS to record cardiac activity. 3) Perform a VM. If the VM is successful in relieving symptoms, the patient will not self-administer study drug but will keep the CMS device on for 5 hours. The episode of PSVT and the results of the VM will be adjudicated, and the patient will remain in the study for a subsequent episode of PSVT. 4) Administer study drug if the symptoms do not resolve after completion of the VM. The patient will push the CMS event marker button to record the time of dosing immediately prior to self-administering each dose of study drug, as applicable. The CMS should not be removed, and the recording should continue for at least 5 hours after study drug administration; The patient should be seated prior to self-administering the first dose of study drug, (each dose consists of 2 sprays of study drug from a single device, one spray in each nostril). If symptoms of PSVT do not resolve within 10 minutes after the first dose of study drug, the patient should administer a second dose of study drug by using the additionally-provided nasal spray device. The second dose of study drug should be taken not earlier than 10, and not later than 15 minutes after the first dose. The patient may gently blow their nose to remove any excess fluid build-up immediately prior to self-administration of the second dose. The patient will push the CMS event marker button immediately prior to self-administering the second dose. In the event that a full dose (i.e., 2 sprays, one in each nostril) of study drug is not administered during the first dose (e.g., due to misuse of device or device malfunction), the patient should wait at least 10 minutes before self-administering a second dose, if needed. Patients should not self-administer a second dose of study drug if they are experiencing tolerability issues believed related to the first dose (e.g., symptoms of lightheadedness/dizziness). 5) Complete the provided patient questionnaires. Questionnaires regarding details of the PSVT episode being treated should be completed as soon as possible after dosing of study drug regimen is completed. Completion of TSQM-9 should be completed as soon as possible after termination of the treated PSVT episode. 6) If the symptoms of PSVT have not resolved within 30 minutes after the start of study drug administration, patients may seek appropriate medical care. When the patient reaches a medical care facility to seek treatment for the PSVT episode, the patient must give the study identification card included in the study kit to the on-site medical personnel. The study identification card contains a brief description of the study, the Investigator and Medical Monitor contact information, and a short questionnaire to be filled out by the on-site physician to document the diagnosis of the episode, the treatment administered, and the outcome. The CMS should not be removed, and recording should continue for at least 5 hours after study drug administration. 7) Schedule a Final Study Visit within 7 days of compound I NS administration.

Follow-up Visits will occur approximately monthly from the time of randomization until the patient has completed the study (i.e., throughout the randomized and open-label treatment periods). These visits can be conducted by patients returning to the investigative site or by the site personnel contacting patients by telephone. During this visit, sites will review patient concomitant medications and health status to ensure patients are eligible to continue in the study, and patients will be re-trained on the procedures they will need to follow when they experience the symptoms of an episode of PSVT. Routine monthly Follow-up Visits are highly recommended but are not mandatory. A missing Follow-up Visit will not be considered a deviation of the protocol, and patients will not be excluded from the study for missing their monthly Follow-up Visits. A Follow-up Visit will also occur if patients experience an episode of PSVT for which they apply the CMS, and the episode is subsequently terminated by a VM. In this case, it is preferred that patients to be on-site for the Follow-up Visit so that site personnel can ensure that all data has been downloaded from the CMS device. Patients will retain their CMS and remain in the study for subsequent episodes of PSVT.

A Final Study Visit will occur at the study site within 7 days after a patient self-administers study drug during the Open-Label Treatment Period, or if for any other reason the patient has completed participation in the study. This visit will occur under the following circumstances: The patient fails the test dose; the patient self-administers study drug (or with the help of a caregiver) for a perceived episode of PSVT during the Randomized Treatment Period, and is determined to have not tolerated the double-blind study drug; the patient self-administers open-label study drug (or with the help of a caregiver) for a perceived episode of PSVT during the Open-Label Treatment Period; the patient has started treatment with a prohibited medication before experiencing an episode of PSVT; the patient withdraws consent from the study for any reason; the Sponsor decides to terminate the study for any reason; or patient is deemed to have completed participation in the study for any other reason.

An End of Study Telephone Follow-Up visit will be completed approximately 30 days after the Final Study Visit to assess AEs. This visit is not required for patients who did not use study drug within 14 days prior to their Final Study Visit.

The study will continue for approximately 6 months after the 180th positively adjudicated PSVT episode of patients treated with double-blind study drug has been adjudicated (unless the study is terminated for other reasons). As this is an event-driven study, the CSED will depend on the rate of accrual of these positively adjudicated PSVT episodes. When the Sponsor announces the formal CSED, sites will be notified and instructed to schedule all active patients to return to the site as soon as possible for a Final Study Visit. The CSED announcement will contain additional information on study closeout timelines.

Patient participation in this clinical study may be discontinued for any of the following reasons: the patient withdraws consent or requests discontinuation from the study for any reason; am occurrence of any medical condition or circumstance that exposes the patient to substantial risk and/or does not allow the patient to adhere to the requirements of the protocol; any medical condition which indicates to the Investigator that continued participation is not in the best interest of the patient; requirement of prohibited concomitant medication; patient failure to comply with protocol requirements or study-related procedures; or termination of the study. If a patient withdraws consent after the test dose and before an episode of PSVT, he/she will be required to undergo the Final Study Visit procedures and will still be considered evaluable in the Test Dose Only Population and Overall Safety Population Randomization and Blinding At the Screening Visit, a unique patient identification number will be established for each patient at the investigational site. This patient identification number will be used for patient identification throughout the study and in all study-related documentation. This will be a 6-digit hyphenated number of the following format: XXX-YYY, where XXX is the unique site identification number and YYY is a sequential unique number assigned to the patient at that site. Each patient number will be assigned only once and will not be reassigned to another patient if a patient fails during the Screening Visit. The IRT will not allow repeat of numbers. This unique identifier is used in all study documentation for that patient from first to last contact.

Patients previously enrolled in the study of Example 2 who subsequently pass a test dose of the compound I dosing regimen will be re-randomized in RAPID (1:1 compound I to placebo).

The Investigator or designee must electronically contact the IRT to acquire a treatment assignment for each patient. This study will be conducted in a double-blind manner and all Sponsor, investigative site, Adjudication Committee, and Clinical Research Organization personnel involved in the study will be blinded to the treatment assignment with the following exceptions: Sponsor Clinical Study Supplies Coordinator and personnel directly involved in manufacturing/packaging of the study drug; the Data and Safety Monitoring Committee (DSMC) (if unblinded safety data is requested); and IRT services personnel.

Unblinding

In the event of an emergency, it will be possible to determine to which treatment the patient has been allocated by calling a 24/7 assistance telephone number provided on the patient's study identification card. The Medical Monitor should be consulted prior to unblinding whenever possible. Any unblinding performed by the Investigator or medical personnel must be recorded in the source documents.

Formulation and Packaging

The formulation of compound I is for intranasal (IN) administration and will consist of compound I, water, acetic acid, disodium ethylene-diamine-tetra-acetic acid (EDTA), and sulfuric acid. The dose of compound I to be evaluated in the present study is 70 mg per nasal spray device, using the dosing regimens described previously. The same formulation will be used for the Test Dose Randomization Visit and for the Randomized and Open-Label Treatment Periods The formulation of placebo will consist of water, sodium acetate, disodium EDTA, and sulfuric acid to reproduce the same pH as the compound I formulation.

Study drug will be labeled according to the requirements of local law and legislation, as well as current Good Manufacturing Practice (GMP) and International Council for Harmonization (ICH) Good Clinical Practice (GCP) guidelines. In compliance with these regulations and guidelines, the label may include information such as the study protocol number, administration sequence, lot number, storage conditions, expiry date, Sponsor identification, or appropriate cautionary language for investigative material. Proof labels, detailing actual label text, will be available in the study files.

Study drug will be packaged according to current GMP and ICH GCP guidelines. The study drug distributor will package the study drug. Double-blind study drug will be uniquely identified with a randomly generated kit identifier. All open-label study drug (i.e., study drug used for Test Dose and for Open-Label Treatment Periods) will be uniquely identified with individual kit identifiers. The kit identifier for each patient will be recorded in the electronic data capture (EDC) system for the study.

The study drug distributor will facilitate the delivery and resupply of study drug to the investigational site. The Investigator or designee must contact the IRT when any unscheduled replacements of study drug are required.

Study Drug Administration

Each nasal spray device delivers a total of 200 µL of compound I NS 70 mg or placebo (i.e., 100 µL in each nostril via the Aptar Pharma Nasal Spray Bidose System [BDS]). The devices will be prefilled and packaged into child-resistant boxes. Instructions for its use are included in each study drug kit and are provided in the MoOP.

Prior to administration, patients should be seated with their head in an upright position. Patients will be instructed to hold their breath and avoid inhaling during study drug administration (a caregiver may help the patient with this procedure). For 10 minutes after each drug administration, patients are to remain in a seated position with their head upright, breathe normally, and refrain from blowing their nose. Patients may gently blow their nose to remove any excess fluid build-up prior to administration of a second dose. A second dose of study drug should be taken not earlier than 10, and not later than 15 minutes after the first dose. This applies to test dose procedures, as well as during randomized and open-label treatment periods to treat perceived PSVT episodes (if symptoms of PSVT persist 10 minutes after the first dose of study drug).

In the event that a full dose of compound I NS 70 mg is not administered during the initial dose (e.g., due to misuse of device or device malfunction), the patient should wait at least 10 minutes before self-administering a second dose, if needed.

Patients should not take a second dose of study drug if they are experiencing tolerability issues believed related to the first dose (e.g., symptoms of lightheadedness/dizziness). If patients report feeling lightheaded/presyncope, they should be instructed to lie down and put their feet up until the symptoms resolve.

Patients will receive study drug as determined by their treatment group assignment. If the BDS does not deploy, it will be considered a missed or partial dose, as applicable.

Treatment Compliance

The patient will self-administer the test dose of study drug at the clinical site with the guidance of study personnel. The date, dosing initiation time, and dose completion time will be recorded. For the double-blind and open-label treatment periods of the study, study drug will be self-administered, or administered with the help of a caregiver and this should be annotated in the electronic case report form (eCRF). Patients will be required to return the used BDS devices, the CMS, and the study identification card to the site at their Final Study Visit. The patient will be questioned about the drug administration, including any issues related to the use of the devices such as failure in deployment of the BDS device, to confirm drug compliance and accountability.

Storage and Accountability

Study drug will be stored at the clinical site at ambient room temperature (15° C. to 30° C. [59° F. to 86° F.]) and will be protected from light in a secure area with access limited to authorized personnel.

During the study, the patient will be instructed to keep and return used BDS devices to the site for final drug accountability. Patients will be instructed to maintain the study drug in an ambient temperature environment at all times. At the conclusion of the study, patients will return unused study drug to the site for final drug accountability during their Final Study Visit.

Records will be maintained at each clinical site indicating the receipt and dispensation of all study drug supplies. The responsible pharmacist or designee at the investigational site must keep an accurate inventory of study drug shipments received and the amount of study drug used or not used by each patient. A full reconciliation of drug inventory will be performed at the end of the study, and the results of the inventory will be recorded in the drug accountability log.

Study Drug Handling and Disposal

The final accountability of study drug will be performed by the Clinical Research Associate (CRA) at the sites. Sites will not be allowed to destroy study drug. All study drug kits will be returned after CRA accountability is completed. If no study drug remains, this will be indicated in the drug accountability log.

Prior and Concomitant Medications and/or Devices

Current participation in any investigational drug or device study or the use of any investigational drug or device within 30 days of the Screening Visit is prohibited.

The use of digoxin or any Class I or III antiarrhythmic drug within less than the equivalent of 5 half-lives of this drug prior to the Test Dose Randomization Visit is prohibited. The use of amiodarone within 30 days prior to the Test Dose Randomization Visit is prohibited.

Drugs for chronic prophylactic treatment of episodes of PSVT (e.g., beta-blockers, verapamil, and diltiazem) cannot be started after randomization. Concomitant "pill-in-pocket" use of these drugs to treat PSVT episodes that do not resolve after treatment with study drug should not be used for at least 30 minutes after the start of study drug administration.

If the treatment with antihypertensive drugs (monotherapy or combinations) is modified after the randomization, a new test dose may be conducted, after consultation with the Medical Monitor.

The use of any drugs of abuse which, in the opinion of the Investigator, would impact the validity of the study results is prohibited.

The use of any concomitant medications or devices will be recorded in the eCRF by the Investigator and documented in the final CSR.

Site Study Procedures

For the Screening Visit, the following procedures will be performed: Obtain informed consent. The patient is considered enrolled in the study when informed consent is obtained; record demographics and medical/surgical history; evaluate and record concomitant medications; perform physical examination (including height and weight); obtain and record vital signs (blood pressure and HR); collect urine sample for central laboratory urinalysis; collect blood sample for safety laboratory testing (hematology, chemistry, and serum pregnancy test for females of childbearing potential) by the central laboratory; perform 12-lead ECG; and confirm eligibility based on inclusion/exclusion criteria (including confirmation of PSVT diagnosis per the MoOP).

For the Test Dose Randomization Visit, the following procedures will occur: Confirm eligibility (additional eligibility criteria apply to pass the test dose at the Test Dose Randomization Visit only): record the CMS identifier number in the EDC system for the test dose; train the patient on symptom identification, assessment, and reporting; train the patient on contacting the Telephone Coach (if possible) who will guide the patient through the study procedures; train the patient on set up and use of the CMS; performance of VMs; train the patient on recording of time(s) of administration of study drug; train the patient administration of compound I NS (as described in the MoOP); train the patient on completion of post-treatment patient questionnaires; train the patient on reporting of adverse events to the sites during the study for evaluation; record concomitant medications; record any post-dose adverse events; and collect urine sample for pregnancy test for females of childbearing potential.

For monthly follow-up visits, the following procedures will occur: ensure the patient continues to be eligible for the study; re-train the patient on (re-training procedures are described in the MoOP); re-train the patient on symptom identification, assessment, and reporting; re-train the patient on contacting the Telephone Coach; re-train the patient on set up and use of the CMS; re-train the patient on Performance of VMs; re-train the patient on Recording of time of administration of study drug; re-train the patient on Completion of patient questionnaires; re-train the patient on Reporting of AEs to the sites during the study for evaluation; and re-train the patient on Administration of study drug (compound I or placebo) with BDS (as described in the MoOP); record any concomitant medications; and record any adverse events. An on-site Follow-up Visit may occur if patients experience an episode of PSVT for which they apply the CMS, and the episode is subsequently terminated by a VM. In this case, it may be necessary for patients to be on-site for the Follow-up Visit so that site personnel can ensure that all data has been downloaded from the CMS device if this cannot be confidently performed remotely. Patients will retain their CMS and remain in the study for subsequent episodes of PSVT.

For the Randomized Treatment Period, the follow procedures occur: collect/review the completed patient questionnaires; record any post-dose AEs; collect and evaluate the used study drug device; evaluate any medical intervention during the Treatment Period; obtain and record vital signs (blood pressure and HR); record concomitant medications; evaluate patient's CMS report if available; collect urine sample for pregnancy test for females of childbearing potential; and assess eligibility for the Open-Label Treatment Period, and if eligible, dispense open-label compound I and provide patient with CMS device (ensure device has been reset), and a new patient questionnaires.

For the Final Study Visit, for patients who failed the test dose the following procedures occur: identify the reason for failure (predefined list is provided in the MoOP); review the cardiac core laboratory CMS test dose report; and close the case with IRT. For all other patients: identify reason for study completion; collect and review the completed patient questionnaires; record any post-dose adverse events; collect and return the study kit, including used or unused study drug, study identification card and used or unused CMS; evaluate any medical intervention during the Treatment Periods; Perform physical examination; obtain and record vital signs (blood pressure and HR); record concomitant medications; evaluate patient's CMS report if available; perform a 12-lead ECG; collect urine sample for central laboratory urinalysis; collect blood sample for safety laboratory testing (hematology, chemistry, and serum pregnancy test for females of childbearing potential) by the central laboratory; and close the case with IRT.

Efficacy

Efficacy assessments will be based on the data derived from CMS recordings. The Adjudication Committee will evaluate the complete ECG data recorded from patients to determine if a true PSVT episode occurred. If the event is related to a confirmed episode of PSVT, the primary endpoint conversion to SR after study drug administration will be adjudicated and the primary variable, the time to conversion, will be adjudicated for the primary efficacy analysis.

The patient will report and rate symptoms of the episode of PSVT and its evolution as well as overall treatment satisfaction in the patient diary and TSQM.

The primary efficacy endpoint is defined as time to an adjudicated termination of a positively adjudicated episode of PSVT and conversion to SR for at least 30 seconds within 30 minutes of start of study drug dosing.

Additional efficacy endpoints include time to conversion at time points prior to, and later than, 30 minutes; time to conversion in patients with the option of repeat administration; the percentage of patients requiring additional medical intervention in emergency department to terminate an episode of PSVT; Relief of specific symptoms (i.e., heart palpitations, rapid pulse feeling, chest pain, anxiety, shortness of breath, dizziness, and fainting) potentially associated with an episode of PSVT; rating of TSQM; and the repeat of key efficacy endpoints in various subgroups of interest (e.g., concomitant medications).

Each event from each patient who assesses symptoms as being caused by PSVT will be documented with an ambulatory CMS recording.

The cardiac monitoring core laboratory will provide the entire 5-hour ECG captured by the CMS to the Adjudication Committee.

The Adjudication Committee will comprise at least 5 members, all cardiac electrophysiologists (EPs), who are independent from the Sponsor and from Sponsor-related operational activities and the DSMC. The Adjudication Committee will review all data, i.e., the entire 5-hour CMS recording, sent to them by the core laboratory for each study episode.

The EPs will adjudicate the following. 1) The presence of PSVT (AVNRT or AVRT determination if possible). Sinus tachycardia, atrial tachycardia, atrial fibrillation, and atrial flutter will not be included in the Efficacy Population. 2) Termination of PSVT due to VM if PSVT was present. 3) Termination of PSVT to SR for at least 30 seconds after study drug administration if PSVT was present. Any bias will be limited by the adjudicators being fully blinded to the patient identifiers and study treatment.

The Adjudication Committee will also adjudicate the time between start of study drug administration and PSVT termination, time to loss of recording signal (if applicable), time of a successful medical intervention (e.g., use of IV adenosine in a medical care facility), or if termination is not observed within 5 hours. The Adjudication Committee will review the full disclosure of the 5-hour CMS recording and will report arrhythmias and conduction disturbances in the eCRF.

Safety and Adverse Events

Safety variables will include clinical adverse events (AEs), vital signs (blood pressure and HR), laboratory testing (hematology, chemistry, and urinalysis), arrhythmias, and conduction disorders detected on surface ECG or CMS recordings. During the compound I test dose period, vital signs, SBP, DBP, HR measurements, arrhythmia, conduction disorders on the ECGs, and clinical AEs will be recorded. These data will be reported in the Overall Safety Population. These variables will be reported in the pre-identified relevant subgroups of patients (e.g., those receiving concomitant beta-blockers, calcium channel blockers, or other drugs known to reduce blood pressure or alter AV conduction) for pre-defined subgroup analyses.

An AE is defined as any untoward medical occurrence associated with the use of a drug in humans, whether or not considered drug-related. An AE can therefore be any unfavorable and/or unintended sign (including an abnormal laboratory finding), symptom, or disease temporally associated with the use of study drug, whether or not related to the study drug. All AEs, including observed or volunteered problems, complaints, or symptoms, are to be recorded on the appropriate eCRF.

Adverse events, which include clinical laboratory test variables, will be monitored from the time of test dose administration (i.e., Test Dose Randomization Visit) until study participation is complete (i.e., after the Final Study Visit). Patients will be instructed to report any AE they experience to the Investigator. Investigators will assess for AEs at each visit and record event(s) on the appropriate AE eCRF.

Wherever possible, a specific disease or syndrome rather than individual associated signs and symptoms will be identified by the Investigator and recorded on the eCRF. However, if an observed or reported sign or symptom is not considered a component of a specific disease or syndrome by the Investigator, it will be recorded as a separate AE on the eCRF. In cases requiring medical or surgical procedures, the underlying condition, rather than the procedure itself, will be recorded as an AE(s).

Any medical condition that is present when a patient is screened or present at baseline that does not deteriorate will not be reported as an AE. However, medical conditions or signs or symptoms present at baseline that change in severity or seriousness at any time during the study will be reported as an AE(s).

Clinically significant abnormal assessments that are detected during the study or are present at baseline and significantly worsen will be reported as AEs or SAEs. The Investigator will exercise his or her medical and scientific judgment in deciding whether an abnormal assessment is clinically significant. Any abnormal assessments considered clinically significant by the Investigator must be recorded on the AE page of the eCRF. Clinically significant abnormal assessments occurring during the study will be followed until repeat tests return to normal, stabilize, or are no longer clinically significant.

The Investigator will rate the severity (intensity) of each AE as mild, moderate, or severe, and will also categorize each AE as to its potential relationship to study drug using the categories of not related, unlikely related, possibly related, probably related, or definitely related.

All noxious and unintended responses to a medicinal product related to any dose should be considered an adverse drug reaction. "Responses" to a medicinal product means that a causal relationship between a medicinal product and an AE is at least a reasonable possibility (i.e., the relationship cannot be ruled out).

An Unexpected Adverse Drug Reaction is defined as an adverse reaction, the nature or severity of which is not consistent with the applicable product information. For compound I (etripamil), the reference safety information is included in the Investigator's Brochure currently in force. The reference safety information will be reviewed yearly and the periodicity of the review will be harmonized with the reporting period of the Development Safety Update Report.

A mild event is an event that is usually transient in nature and generally does not interfere with normal activities. A moderate event is an event that is sufficiently discomforting to interfere with normal daily activities. A severe event is an event that is incapacitating, causing an inability to work or perform normal activities.

The assessment of the relationship of an AE to study drug administration is a clinical decision based on all available information at the time the event is reported.

The relationship of an AE to study drug administration is to be assessed according to the following definitions:
Not related—An event that is definitely not associated with study drug administration and is judged clearly due to causes other than study drug.
Unlikely related—An event that follows a temporal sequence from study drug administration, such that a relationship is not likely and could be reasonably explained by the patient's clinical state or other modes of therapy administered to the patient.
Possibly related—An event that follows a reasonable temporal sequence from study drug administration, but may be due to another cause and could also be reasonably explained by the patient's clinical state or other modes of therapy administered to the patient.
Probably related—An event that follows a reasonable temporal sequence from study drug administration that is not easily explained by another cause (e.g., known characteristics of the patient's clinical state or other treatment), and is confirmed by improvement on stopping or slowing study drug administration.
Definitely related—An event that is clearly associated with study drug administration.

An SAE that has been assessed as "possibly related" "probably related" or "definitely related" will be classified as "related" for regulatory reporting purposes. An SAE that has been assessed as "not related" or "unlikely related" will be classified as "unrelated" for regulatory reporting purposes.

The temporal sequence from study drug administration should be considered. The event should occur after study drug administration. The length of time from study drug exposure to event will be evaluated in the clinical context of the event.

Underlying, concomitant, and/or intercurrent diseases should be considered. Each report will be evaluated in the context of the natural history and course of the disease being treated and any other disease the patient may have.

Concomitant medication should be considered. The other medications the patient is taking or the treatment the patient receives will be examined to determine whether any might be recognized to cause the event in question.

Known response pattern for this class of study drug should be considered. Clinical and/or preclinical data may indicate whether a particular response is likely to be a class effect.

Exposure to physical and/or mental stresses should be considered. The exposure to stress might induce adverse changes in the recipient and provide a logical and better explanation for the event.

The pharmacology and PK of the study drug should be considered. The known pharmacological properties (e.g., absorption, distribution, metabolism, and excretion) of the study drug will be considered.

In the event of death, a single cause of death will be recorded as an AE. Death is an outcome and is not considered an AE. An exception is sudden death, when the cause is unknown.

Any AE will be followed (up to a maximum of 30 days after the patient's last dose of study drug in the study) to a satisfactory resolution, until it becomes stable, or until it can be explained by another known cause(s) (i.e., concurrent condition or medication) and clinical judgment indicates that further evaluation is not warranted. All findings relevant to the final outcome of an AE will be included in the EDC.

Patients who have not taken any study drug within 14 days prior to their Final Study Visit do not need AEs followed after their Final Study Visit. AEs ongoing at the time of database lock should have all available information entered into the database and be followed as described in this section in case the AE eventually meets an SAE criterion.

All SAEs should be followed until satisfactory resolution, even after database lock.

An AE or suspected adverse reaction is considered serious if, in the view of either the Investigator or the Sponsor, it results in any of the following outcomes: death, a life-threatening AE, an event that requires hospitalization or prolongation of existing hospitalization, a persistent or significant incapacity or substantial disruption of the ability to conduct normal life functions, a congenital anomaly/birth defect, or an important medical event. Important medical events that may not result in death, a life-threatening situation, or hospitalization may be considered an SAE when, based upon appropriate medical judgment, they may jeopardize the patient and may require medical or surgical intervention to prevent any of the outcomes listed above. Examples of such medical events include allergic bronchospasm requiring intensive treatment in an emergency room or at home, blood dyscrasias or convulsions that do not result in inpatient hospitalizations, or the development of drug dependency.

Any SAE occurring from the time of study drug administration at the Test Dose Randomization Visit through the Final Study Visit must be reported to Medpace Clinical Safety within 24 hours of awareness of the event. Any SAE occurring within a 30-day follow-up period after taking the study drug that the Investigator considers related to study drug administration must be reported in the same manner.

Patients are requested to report to the Investigator any pregnancies of themselves or their partner(s) (informed consent is required for partner[s] prior to collecting any information) that occur within 30 days of study drug administration. The Investigator should report the pregnancy to Medpace Clinical Safety within 24 hours of notification. If a patient becomes pregnant during the study, the patient should be withdrawn from the study and Final Study Visit procedures should be performed.

After the pregnancy is reported, Medpace Clinical Safety personnel will forward the exposure in utero form to the Investigator for completion. The Investigator should monitor the patient/partner until completion of the pregnancy. If the pregnancy ends for any reason before the anticipated date, the Investigator should notify Medpace Clinical Safety. At the completion of the pregnancy, the Investigator will document the outcome of the pregnancy. If the outcome of the pregnancy meets the criteria for immediate classification as an SAE (i.e., postpartum complication, spontaneous abortion, stillbirth, neonatal death, or congenital anomaly), the Investigator should follow reporting procedures for an SAE.

The Sponsor will report all relevant information about suspected unexpected serious adverse reactions that are fatal or life-threatening as soon as possible to the United States Food and Drug Administration (FDA), Health Canada, and applicable competent authorities in all the Member States concerned, and in any case no later than 7 days after knowledge by the Sponsor of such a case, and that relevant follow-up information will subsequently be communicated within an additional 8 days.

All other suspected unexpected serious adverse reactions will be reported to the FDA, Health Canada, and applicable competent authorities concerned as soon as possible but within a maximum of 15 days of first knowledge by the Sponsor. The Sponsor will also inform all Investigators as required.

All medical device adverse events are to be recorded on the appropriate eCRF. In the United States, medical device complaints or product problems with the spray device may be voluntarily reported by the Investigator to the FDA through MedWatch, the FDA Safety Information and Adverse Event Reporting Program.

Standard clinical laboratory profiles for hematology, serum chemistry, and urinalysis will be evaluated at the Screening Visit and at the Final Study Visit. Serum pregnancy tests will be performed on female patients of childbearing potential at the Screening Visit and at the Final Study Visit, and a urine pregnancy test will be performed at the Test Dose Randomization Visit and at the Randomized Treatment Visit Follow-Up Visit.

Vital signs (i.e., SBP, DBP, and HR) will be obtained at the Screening Visit, at the Test Dose Randomization Visit, at the Randomized Treatment Follow-Up Visit, and at the Final Study Visit. At the Test Dose Randomization Visit, vital signs will be obtained after at least a 5-minute rest in a seated position within 10 minutes before test dose administration. Following start of compound I administration, vital signs will be obtained every 5 minutes (±1 minute) for 45 minutes. Vital signs will be obtained if the patient reports any symptom potentially related to drop in blood pressure.

A 12-lead ECG will be performed at the Screening Visit, at the Test Dose Randomization Visit, and at the Final Study Visit. During the Test Dose Randomization Visit, patients should be sitting comfortably for a minimum of 5 minutes before starting the procedure. The test dose procedure must not be carried out in the standing or fully supine position. The MoOP will provide the details for interpreting ECGs and on-screen continuous monitoring.

A physical examination will be performed at the Screening Visit and at the Final Study Visit. Body height and weight will be measured at the Screening Visit.

Statistical Analysis

The Efficacy Population includes all randomized patients who use the study drug to treat a positively adjudicated episode of PSVT. This population does not include patients who take the study drug for a negatively adjudicated episode of PSVT (i.e., symptoms not associated with an episode of PSVT). The subjects will be included in the treatment arm (placebo or double-blind study drug) in which they were randomized.

The modified Intent to Treat (mITT) Population includes all randomized patients who take the randomized study drug for a perceived episode of PSVT. The subjects will be included in the treatment arm (placebo or double-blind study drug) in which they were randomized.

The Test Dose Only Population includes all patients who receive the test dose of compound I NS 70 mg, but do not receive randomized drug (Overall Safety Population, minus the Safety Population). The Test Dose Only Population will also include pre-identified relevant subgroups of patients (e.g., those receiving concomitant beta-blockers, calcium channel blockers, or other drugs known to reduce blood pressure or alter AV conduction) for pre-defined subgroup analyses.

The Safety Population includes all randomized patients who take the randomized study drug for a perceived episode of PSVT. The subjects will be included in the treatment arm (placebo or double-blind study drug) according to actual received treatment.

The Overall Safety Population includes the Safety Population and the Test Dose Only Population.

The numbers and percentages of patients will be provided for patient disposition and for each study population. For randomized patients who discontinue from the study, the primary reason for discontinuation will be listed and summarized by treatment group. Summary statistics will be provided by treatment group for demographic characteristics (e.g., age, gender, race, and ethnicity) and for baseline disease variables.

Log entries detailing the administration of the test dose and the administration of the study drug (compound I or placebo) to randomized patients will be listed. Verbatim terms for concomitant medications will be coded using the latest version of the World Health Organization Drug Dictionary (WHODD). The numbers and percentages of patients in each treatment group taking concomitant medications will be summarized by anatomical therapeutic chemical classification and preferred term.

The efficacy analyses will be performed on the Efficacy Population. Additional sensitivity efficacy analyses and exploratory efficacy analyses will be performed on the other populations. The safety analyses will be performed on the Safety Population for double-blind randomized treatment, and for the Overall Safety population for open label data. Sensitivity analyses on other populations and subgroups may be performed as specified in the SAP, safety analysis of one dose versus two dose, and safety analyses for the open-label treatment period.

The main estimator (primary efficacy endpoint) for the study will be time to adjudicated termination of a positively adjudicated episode of PSVT and conversion to sinus rhythm (SR) for at least 30 seconds within 30 minutes of study drug dosing.

Data from the single dose arm will be pooled with data from the optional second dose arm for both compound I and placebo groups for the primary analysis. Medical intervention is a key intercurrent event in the trial. For the primary analysis, a hypothetical strategy will be utilized; patients who receive medical intervention will be considered as treatment failures, and censored at the end of the observation period. Sensitivity analyses including a composite strategy (analyzed via Wei Lin Weiss method) and treatment policy (with patients censored at time of conversion due to medical intervention) may also be conducted.

The main estimate (primary analysis of the primary endpoint) will be derived by Kaplan Meier estimates of time to conversion at 30 minutes using the Wilcoxon test. Patients who received medical interventions for treatment of PSVT will be censored at Minute 31. Patients who have not achieved conversion by Minute 30 will be censored by Minute 31. The hazard ratio (active/control) and the two-sided 95% confidence interval (CI) will be calculated using Cox regression model with treatment effect.

The primary comparison will be the difference between pooled compound I (etripamil) arm (pooled data from the single dose arm and the optional second dose arm) and pooled placebo ((pooled data from the single dose arm and the optional second dose arm). The secondary interest of comparison will be the difference of between compound I optional second dose arm and single compound I arm. It should be noted that the objective of this comparison is not to achieve significant p-value due to the sample sizes. Rather, the objective is to assess the trend of the optional second dosing effect.

A type I error control strategy using a hierarchical gate-keeping approach among sensitivity estimators (secondary endpoints) will be defined in the statistical analysis plan. Sensitivity estimators will include the following: tests of the duration of treatment effect, via Kaplan Meier estimates of time to conversion at 5, 10, 15, 45, 60, 90, 120, 180, 240, and 300 minutes; tests of the impact of a treatment regimen which includes an optional second dose, via comparisons of efficacy in the single dose regimen arms versus optional second dose arms, and comparisons of the proportion of patients who take a second dose within the optional second dose compound I and placebo arms; tests of the 'at-home setting' component of the estimand, via comparison of the proportion of patients who seek additional medical intervention, rescue medication, or emergency medical care; tests of clinical benefits, via comparison of patient reported treatment effectiveness and overall satisfaction, as measured by the TSQM-9 and other patient reported symptoms; tests of the robustness of analysis method, via landmark analyses of conversion rates at 3, 5, 10, 15, 20, 30, 45, 60, and 90 minutes after drug administration; tests of the robustness of analysis method, via use of alternative censoring methods for patients who receive additional medical intervention, including a composite strategy (analyzed via Wei Lin Weiss method) and treatment policy (with patients censored at time of conversion due to medical intervention); tests of the robustness of statistical method, via use of Log-rank method for the main estimator, and sensitivity estimators using Kaplan Meier analyses; tests of the safety of compound I (etripamil) via clinical adverse events (AEs), vital signs (blood pressure and HR), laboratory testing (hematology, chemistry, and urinalysis), arrhythmias, and conduction disorders detected on ECG or CMS recordings; and tests of the selected patient population, via efficacy and safety analyses on subgroups of interest and on the mITT which includes patients with negatively adjudicated PSVT.

Safety data will be summarized with descriptive statistics. Continuous safety data will be presented with n, minimum, maximum, median, mean, and standard deviation, whereas discrete safety data will be summarized with frequency counts and percentages.

The study of Example 2 was completed with 431 patients enrolled (completed a test dose), 419 patients randomized and 156 presenting with a positively adjudicated episode of PSVT. It is assumed that 35% of the episodes of PSVT will be converted to SR in the placebo group and 54% in the compound I group by 30 minutes. These assumptions are based on results obtained in Example 2. A total sample size of 180 patients with a positively adjudicated PSVT episode, randomized at a range of 1:1 to 2:1 ratio (active:control) provides at least 80% power to detect a significant treatment difference for the primary endpoint at a two-sided significance level of 0.05. It is anticipated that as many as 500 additional patients may need to be randomized to accrue a sufficient number of patients in the Efficacy Population within 18 months.

Example 4: Two 70 mg Dose Nasal Administration of Compound I in Subjects in Sinus Rhythm A population of 46 subjects in sinus rhythm received one 70 mg dose of compound I according to the protocol of Example 2, and after several months the dose regimen of 70 mg followed by a repeat same dose of 70 mg 10 minutes later as in the protocol of Example 3.

Two dose administration followed the same protocol as single dose administration for the initial dose, however 10 minutes after the first 70 mg dose of compound I, a second 70 mg dose of compound I was administered. For the second dose, the patients were allowed to blow their nose to remove any excess fluid build-up immediately prior to self-administration of the second 70 mg dose.

Figure 5:
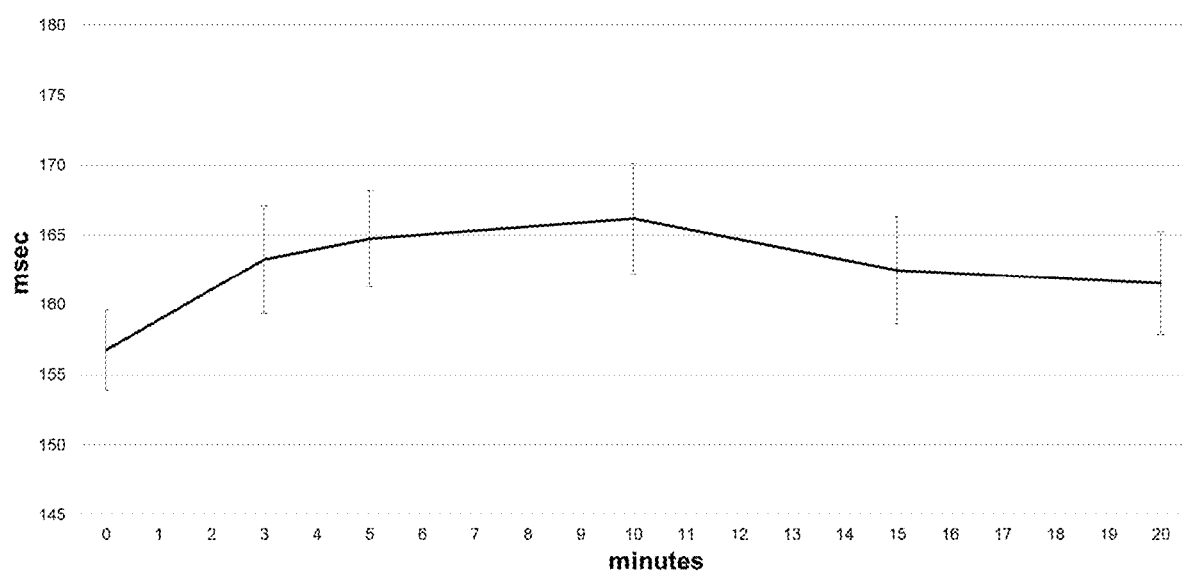
FIG. 5 is graph illustrating PR interval following a single 70 mg intranasal dose of compound I.
Figure 6:
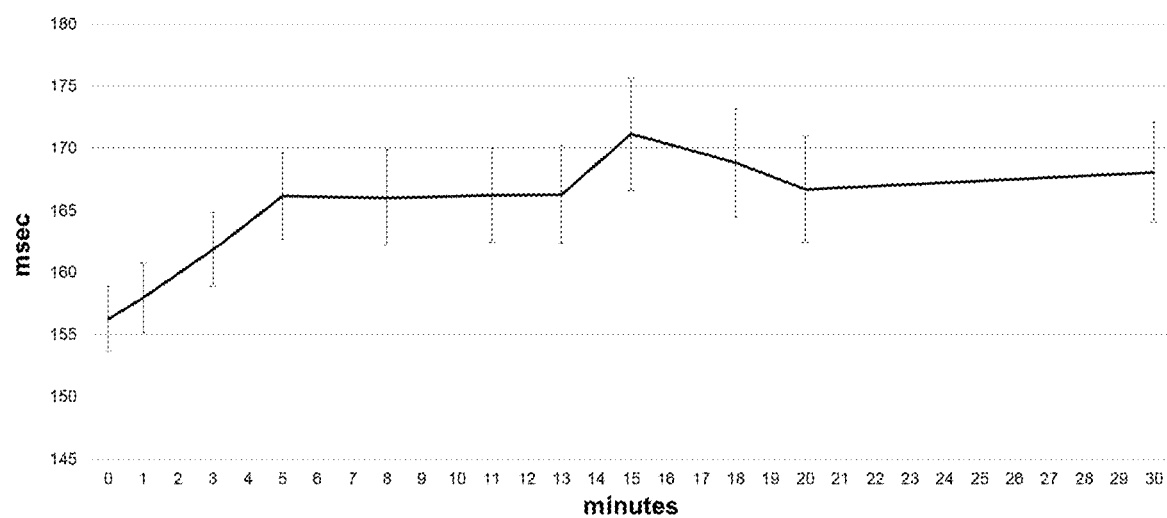
FIG. 6 is graph illustrating PR interval following a first 70 mg intranasal dose of compound I with a second 70 mg intranasal dose of compound I at 10 minutes.

The subjects PR interval was measured on ECG at several timepoints during both administration of a single 70 mg dose of compound I, as well as during a two 70 mg dose of compound I. As illustrated in FIG. 5, an increase in PR interval was observed after a single 70 mg administration of compound I (15 msec, Standard Error [SE] 2) and, as shown in FIG. 6, increased after a repeat administration of 70 mg of compound I (21 msec, SE 3), the second 70 mg dose being 10 minutes after the initial 70 mg dose. The maximum percentage increase was 9% SE 1.14 with a single administration and 14% SE 1.54 with a repeat dose of 70 mg. The PR increase was more prolonged with the repeat dose of 70 mg than with the single dose of 70 mg.

Figure 7:
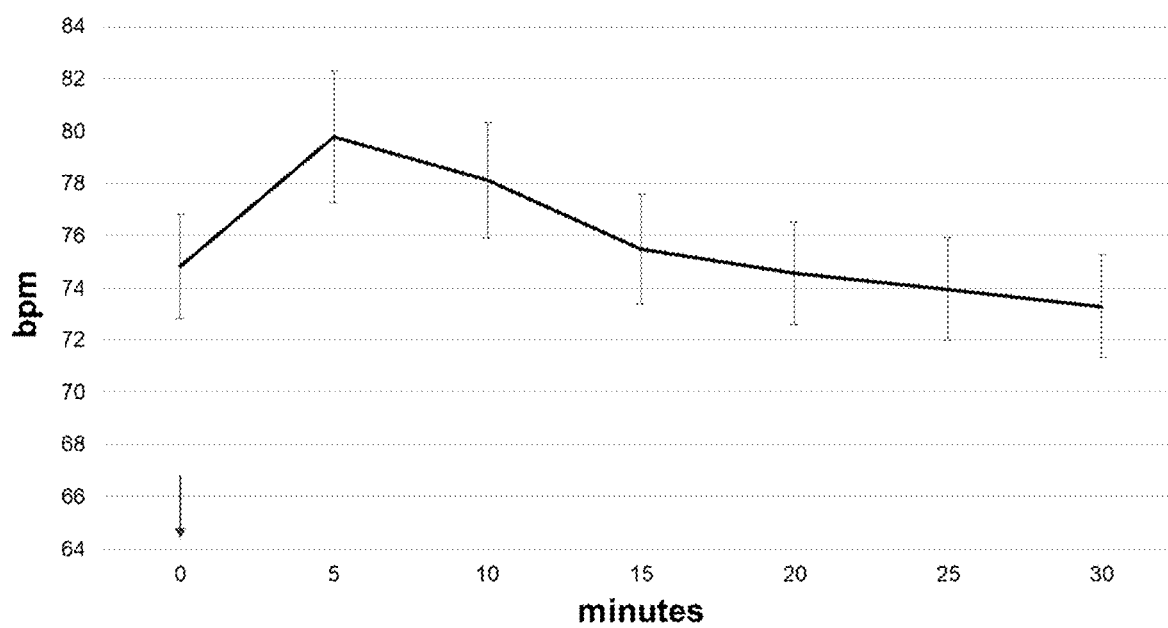
FIG. 7 is graph illustrating mean heart rate following a single 70 mg intranasal dose of compound I.
Figure 8:
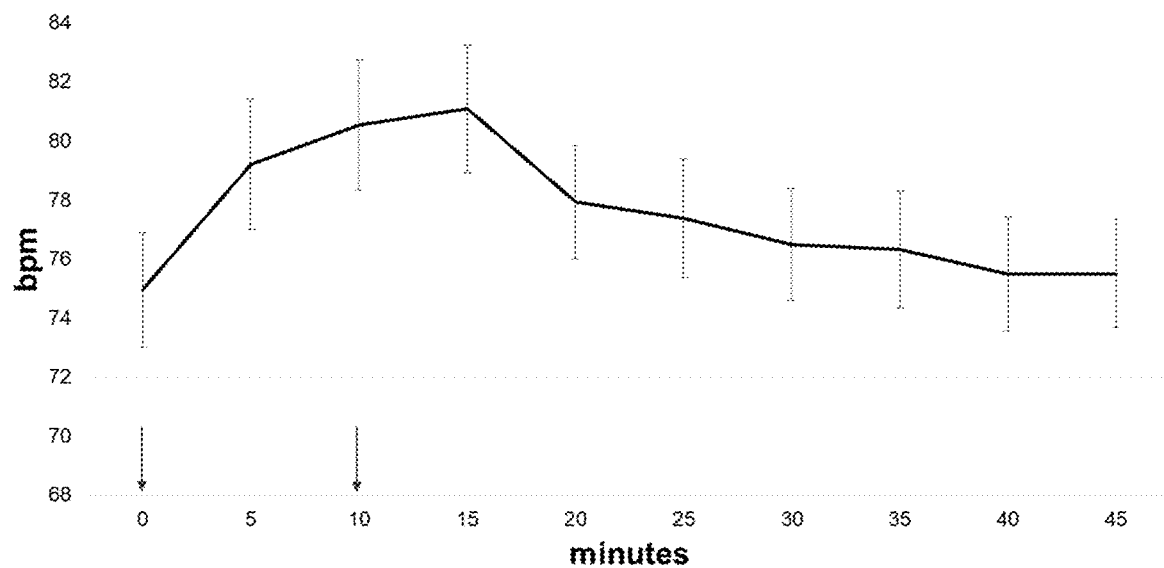
FIG. 8 is a graph illustrating mean heart rate following a first 70 mg intranasal dose of compound I with a second 70 mg intranasal dose of compound I at 10 minutes.
Figure 9:
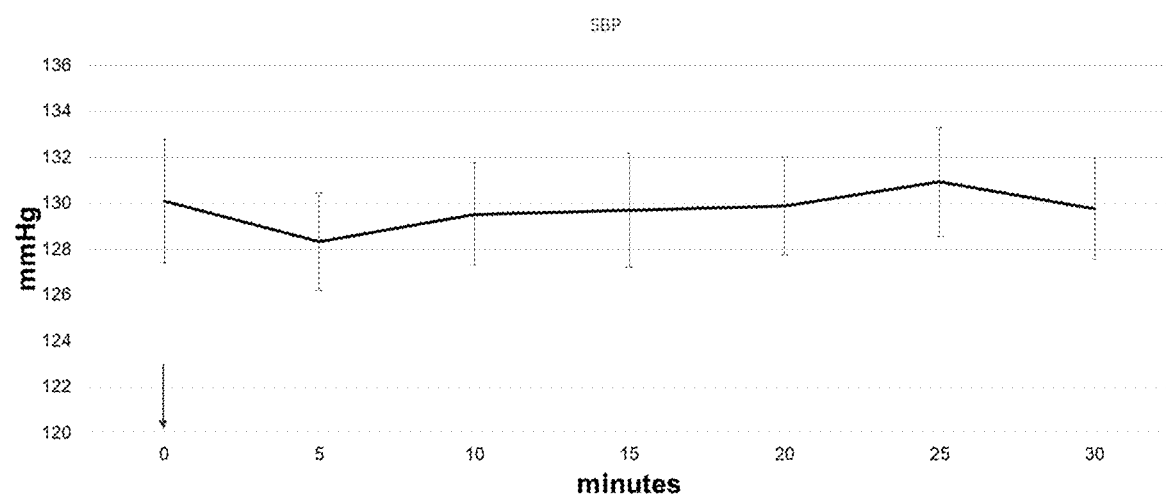
FIG. 9 is a graph illustrating mean systolic blood pressure following a single 70 mg intranasal dose of compound I.
Figure 10:
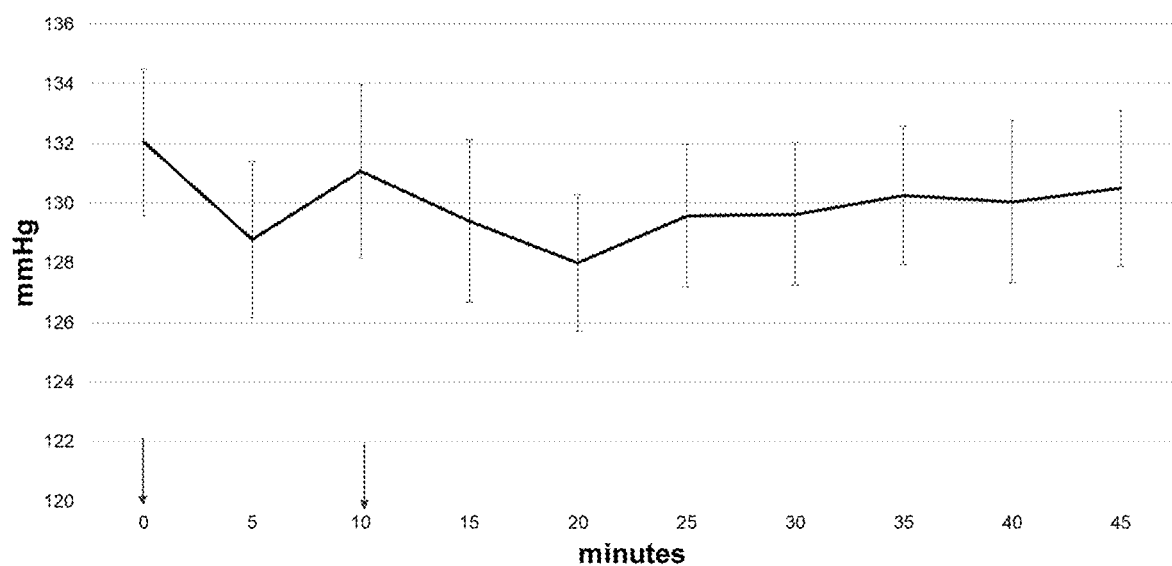
FIG. 10 is a graph illustrating mean systolic blood pressure following a first 70 mg intranasal dose of compound I with a second 70 mg intranasal dose of compound I at 10 minutes.

A two dose regimen of 70 mg of compound I was seen to be safe and was well tolerated as compared to a single dose regimen of 70 mg of compound I. No severe adverse reactions were seen. No new AV block was observed. Vital signs were within normal values and remained stable. FIG. 7 illustrates mean heart rate following a single 70 mg dose of compound I. FIG. 8 illustrates mean heart rate following a first 70 mg dose of compound I with a second 70 mg dose of compound I at 10 minutes. No systolic blood pressure under 99 mmHg was seen. FIG. 9 illustrates mean systolic blood pressure following a single 70 mg dose of compound I. FIG. 10 illustrates mean systolic blood pressure following a first 70 mg dose of compound I with a second 70 mg dose of compound I at 10 minutes. Both heart rate and systolic blood pressure remain in normal ranges following both a single 70 mg dose of compound I, and two doses of 70 mg of compound I separated by 10 minutes.

These results are indicative that a two-dose treatment regimen is likely to be effective in alleviating PSVT symptoms in a patient who still experiences PSVT symptoms 10 minutes after the first dose.

Example 5: A Reduction in Heart Rate in Patients with PSVT Prior to Conversion to Sinus Rhythm Compound I is a rapidly and short acting, nasally administered calcium channel blocker being developed to terminate AV nodal-dependent PSVT. This analysis addresses the effect of compound I on heart rate (HR) during PSVT prior to conversion to sinus rhythm (SR).

Objectives of this analysis are to evaluate the effect of compound I on heart rate during PSVT prior to conversion to sinus rhythm and to evaluate the correlation of heart rate with patient-reported outcomes.

For this analysis, 156 subjects experienced a vagal-maneuver refractory, symptomatic episode of confirmed PSVT, 107 subjects self-administered compound I and 49 placebo (2:1 randomization) during PSVT. Each PSVT was documented by an ambulatory cardiac monitoring system that was placed on the chest after symptoms began. Baseline (average of four values before drug administration), and every minute of heart rate data were captured from baseline until one minute before the PSVT was converted to sinus rhythm. Adequate heart rate data were available for 150 subjects, 102 on compound I and 48 on placebo. Six subjects were not included in this analysis, 4 converted before one minute (3 compound 1 and 1 placebo) and 2 compound I subjects experienced an early defect of recording.

Demographics and baseline characteristics were generally well-balanced between treatment groups, as shown in Table 1. Among patients treated with compound I, mean (SD) age was 57.2 years, most patients were female (67.6%) and majority were white (87.3%).

TABLE 1

|  | Etripamil (N = 102) | Placebo (N = 48) |
| --- | --- | --- |
| Age (years) | | |
| Mean (SD) | 57.2 (12.56) | 54.7 (15.01) |
| Median Q1, Q3 | 60.5 (52.0, 65.0) | 57.0 (46.5, 65.5) |
| Gender, n (%) | | |
| Female | 69 (67.6%) | 32 (66.7%) |
| Male | 33 (32.4%) | 16 (33.3%) |
| Race, n (%) | | |
| White | 89 (87.3%) | 41 (85.4%) |
| Black or African American | 5 (4.9%) | 3 (6.3%) |
| Asian | 4 (3.9%) | 2 (4.2%) |
| Other | 4 (3.9%) | 2 (4.2%) |
| Ethnicity, n (%) | | |
| Hispanic or Latino | 2 (2.0%) | 0 (0.0%) |
| Non-Hispanic or Latino | 97 (95.1%) | 45 (93.8%) |
| Not Reported | 3 (2.9%) | 3 (6.3%) |
| Number of ER Visits for PSVT Events | | |
| Mean (SD) | 2.6 (3.44) | 3.5 (4.12) |
| Median (Q1, Q3) | 2.0 (1.0, 3.0) | 2.0 (1.0, 4.0) |
| Number of PSVT Events in the Past Year | | |
| Mean (SD) | 7.3 (7.10) | 10.4 (13.23) |
| Median (Q1, Q3) | 4.0 (2.0, 10.0) | 6.0 (3.0, 10.0) |
| Age at PSVT confirmation | | |
| Mean (SD) | 56.2 (12.64) | 53.9 (15.16) |
| Median (Q1, Q3) | 58.9 (49.9, 65.0) | 56.7 (43.8, 65.6) |
| Body Mass Index | | |
| Mean (SD) | 28.3 (7.63) | 28.5 (6.30) |
| Median (Q1, Q3) | 27.2 (23.2, 31.8) | 26.8 (23.7, 32.2) |
| Current use of CCB, n (%) | 28 (27.5%) | 13 (27.1%) |
| Current use of BB, n (%) | 37 (36.3%) | 21 (43.8%) |

BB = beta blocker,
CCB = calcium channel blocker,
ER = emergency room,
SD = standard deviation Baseline mean (±SE) heart rate were 179 (±2.8) and 174 (±4.0) bpm for compound I and P respectively. Mean change in heart rate from baseline was greater in the compound I group than placebo group (p<0.0001). This decrease appeared within the first minute (−5 bpm±0.9), 3 min (−10 bpm±1.2), 10 min (−16 bpm±2.1), 30 min (−14 bpm±3.4) and 40 min (−13 bpm±2.9) after compound I administration. The notable decrease in the compound I group was sustained through the 60-minute observation period. A statistically significant difference in HR was reached between compound I and placebo notably at 3 (p<0.03), 10 (p<0.0001), 30 (p<0.0002), and 40 min (p<0.004), but not at 60 minutes, possibly attributed to lower patient numbers.

Figure 11:
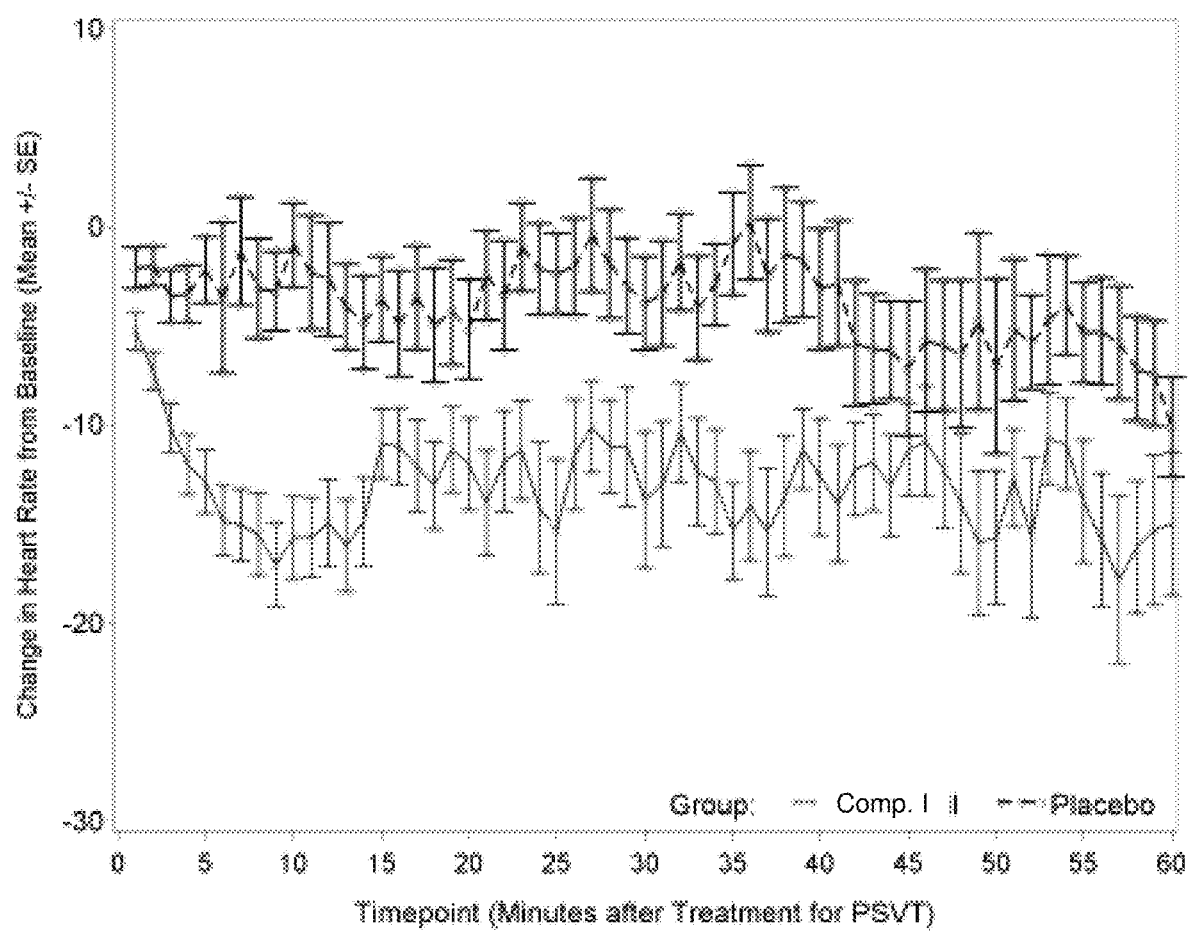
FIG. 11 is a graph showing mean change in heart rate from baseline in subjects administered compound I (solid line on bottom) and placebo (dashed line on top). HR=heart rate, PSVT=paroxysmal supraventricular tachycardia, SE=standard error.

FIG. 11 shows the change in heart rate from baseline over time following administration of compound I or placebo. Of note, patients drop out from the data when no longer experiencing PSVT.

Patient-related outcomes include patient-reported satisfaction with treatment effectiveness, assessed by calculating the TSQM-9 score for the effectiveness domain using the first 3 TSQM-9 questions:
1. How satisfied or dissatisfied are you with the ability of the medication to treat your condition?
2. How satisfied or dissatisfied are you with the way the medication relieves your symptoms?
3. How satisfied or dissatisfied are you with the amount of time it take the medication to start working?

The calculation was as follows: ([(Question 1+Question 2+Question 3)−3] divided by 18)×100.

Patient-reported relief of symptoms, assessed by taking the score on TSQM question 2 "How Satisfied are you with the way the medication relieves your symptoms?", and comparing the average score between treatment groups The Effectiveness domain score, and TSQM question 2 for patients with specific symptoms were analyzed using an ANOVA model.

Figure 12:
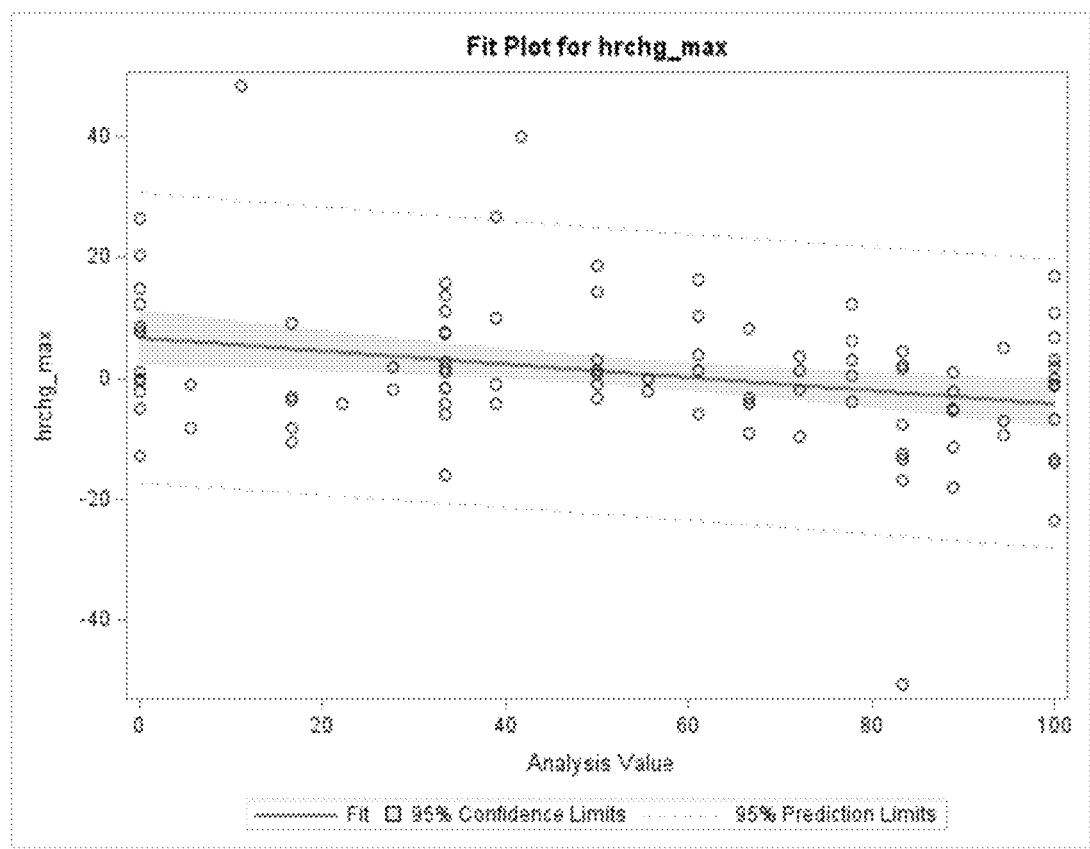
FIG. 12 is a graph showing maximal change in heart rate from baseline vs. patient reported treatment effectiveness following administration of compound I. The x-axis values are ratings to the composite of effectiveness questions (0=most dissatisfied for effectiveness, 100=most satisfied for effectiveness. HR=heart rate. $R^2$=0.086, P=0.0034.
Figure 13:
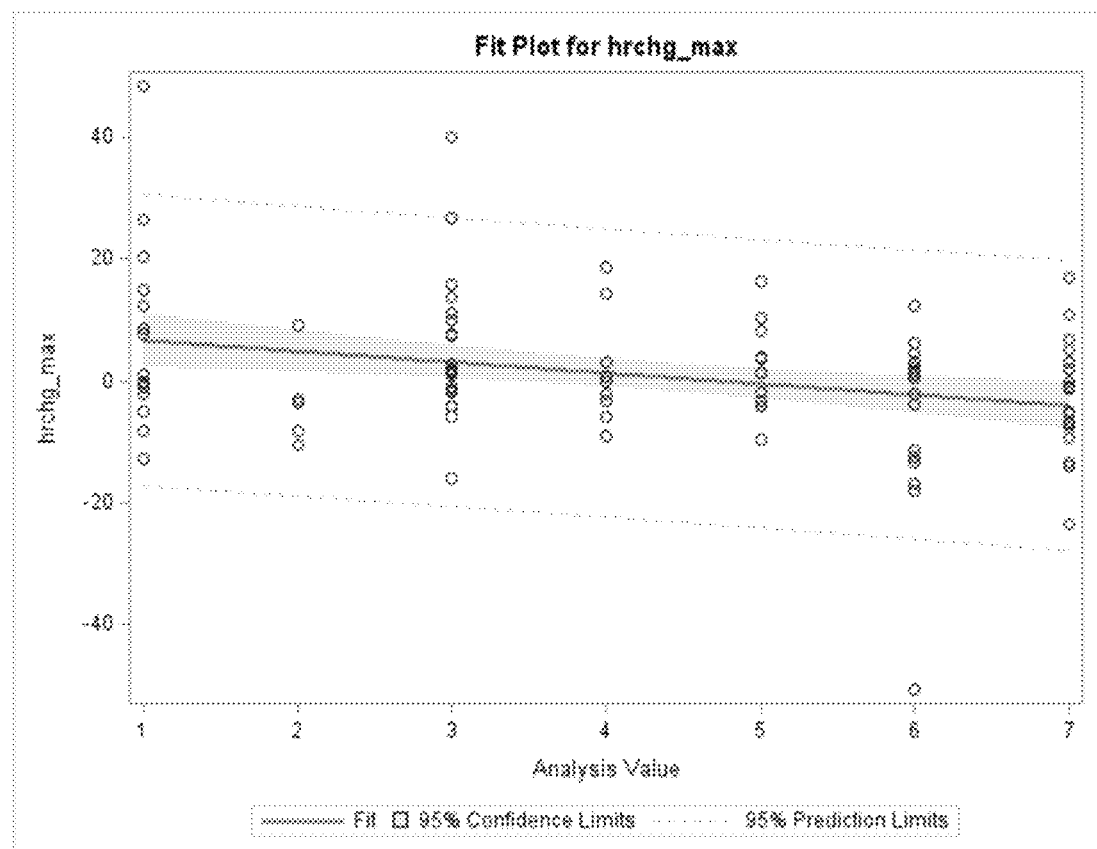
FIG. 13 is a graph showing maximal change in heart rate from baseline vs. answer to a question regarding relief of symptoms. The x-axis values are ratings to the TSQM-9 question 2 (1=most dissatisfied, 7=most satisfied). $R^2$=0.090, P=0.0027.

Among patients treated with compound I, maximal change in heart rate from baseline was positively correlated with patient-reported outcomes of satisfaction of treatment effectiveness ($R2=0.086$; $P=0.0034$; FIG. 12) and satisfaction with relief of symptoms ($R2=0.090$; $P=0.0027$; FIG. 13).

Figure 14:
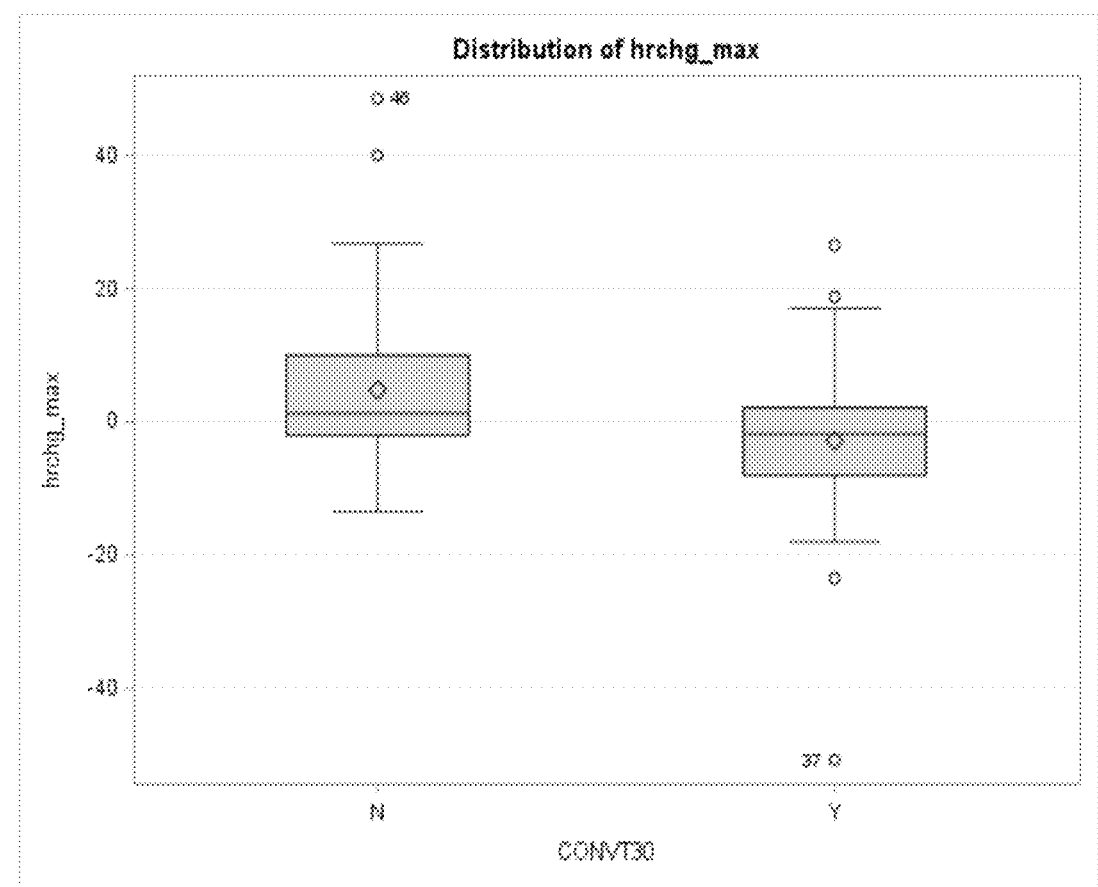
FIG. 14 is a graph showing maximal change from baseline in heart rate among compound I treated patients converting to sinus rhythm at less than 30 and greater than 30 minutes. The box plot shown presents median (middle line in box), mean (diamond), first and third quartiles (ends of box), maximum and minimum values (whiskers), and outlines (circles). HR=heart rate; SR=sinus rhythm. P=0.0014.
Figure 15:
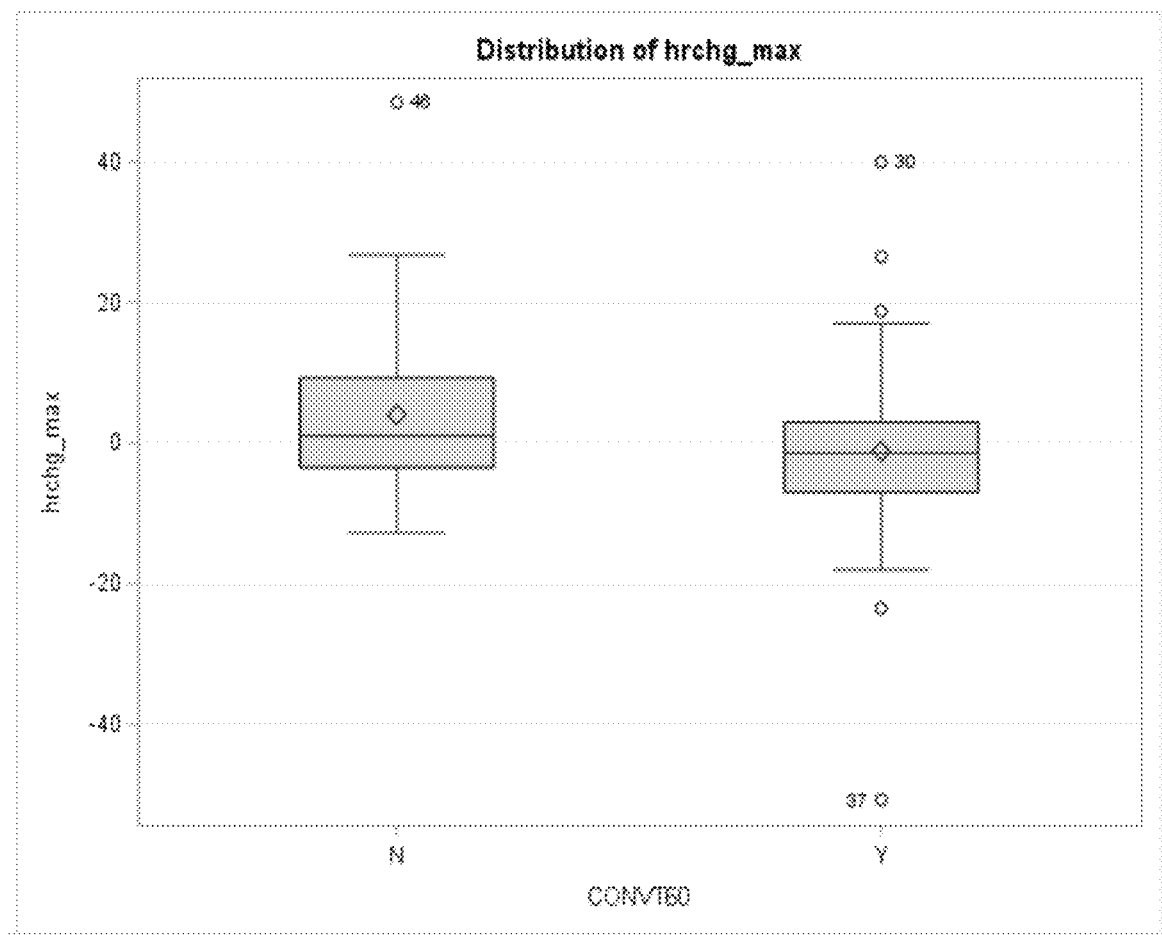
FIG. 15 is a graph showing maximal change from baseline in heart rate among compound I treated patients converting to sinus rhythm at less than 60 and greater than 60 minutes.

Among patients treated with compound I who converted to sinus rhythm, a significant difference was observed in maximal change from baseline in heart rate for patients who converted to sinus rhythm in <30 minutes versus>30 minutes (FIG. 14) and among patients who converted to sinus rhythm in <60 minutes versus>60 minutes (FIG. 15).

Compound I was shown to significantly decrease the heart rate in PSVT prior to conversion to sinus rhythm up to 40 minutes after treatment and was sustained over the 60-minute observation period. The impact on heart rate was an unexpected result given the pharmacokinetic profile of compound I. Maximal change in heart rate from baseline was positively correlated with patient reported relief of symptoms and treatment effectiveness.

Example 6: Nasal Administration of Compound I for Treatment of Atrial Fibrillation Background Atrial fibrillation (AF) is the most common sustained arrhythmia in humans, with an irregular and often rapid heart rate that increases the risk of stroke and heart failure.

Prevalence estimates range from four to six million patients suffering from atrial fibrillation in the United States. Approximately 25% of these have Paroxysmal Atrial Fibrillation (PAF), another 25% have persistent atrial fibrillation, and 50% have permanent atrial fibrillation.

For most patients, current treatment for AF consists of anti-coagulant therapy, either warfarin or novel oral anti-coagulants (e.g., Pradaxa®, Xarelto®, Eliquis®) to reduce the risk of blood clot embolization and stroke; those who cannot take these stronger blood thinners may be prescribed aspirin at 325 mg a day, but aspirin has only been shown to be somewhat efficacious in a very small and specific population. With regard to the abnormal heart rate that occurs during AF, there are two strategies. One strategy focuses on controlling the heart rate during AF to reduce or eliminate symptoms, while the other takes aim at terminating AF and maintaining sinus rhythm. Multiple clinical studies have demonstrated that there is no difference in outcome whether a rate or rhythm control strategy is pursued (e.g., AF-CHF AFFIRM). The major unmet needs are for more efficacious and safer rhythm-control drugs as well as rate-control drugs with a faster onset of action to bring down the heart rate.

Rhythm control drugs such as amiodarone, dronedarone, flecainide, ibutilide are modestly effective in converting atrial fibrillation into normal sinus rhythm but are often associated with toxicity and can cause life-threatening pro-arrhythmic effects. Rate-control drugs include calcium channel blockers (diltiazem and verapamil) and beta blockers (e.g., metoprolol, atenolol), and their goal is to minimize symptoms associated with an increased ventricular rate, improve cardiac output, and prevent tachycardia-associated cardiomyopathy.

Patients who present to the emergency room in AF with a rapid heart rate are almost universally treated with an intravenous calcium channel blocker or beta blocker to provide a rapid reduction in ventricular rate to control symptoms and improve cardiac output. IV rate-control drugs for immediate rate-control, however, are limited to use in the acute setting and therefore cannot be self-administered by patients in the outpatient setting when symptoms begin. Oral rate-control drugs can be taken at home, but do not provide immediate ventricular rate-control due to the delayed 30 to 90-minute onset of action by the oral route.

Compound I addresses an unmet medical need because there are currently no short-acting products available for patient self-administered treatment of episodes of atrial fibrillation.

The rapid onset of action and duration of effect afforded by compound I nasal spray should provide patients with immediate symptom relief while waiting for AF to spontaneously resolve or waiting for adjunctive oral medications to take effect.

Study Design

This is a multi-center, randomized, double-blind, placebo-controlled study to evaluate the effects of compound I in patients with AF. This study includes screening procedures, treatment procedures, and a follow-up period. Patients will be randomized in a double-blind fashion to yield at least 50 evaluable patients in 2 groups of at least 25 patients each (Efficacy Population). Each patient will receive a single dose of Placebo or 70 mg of compound I intranasally.

Screening and treatment procedures should be performed at the same visit. Informed consent must be obtained prior to any study-specific procedures being completed. Patients will be contacted by phone (or other available telemedicine application) for follow-up the next day and 7 days after dosing (on-site follow-up visits may be performed as necessary) Total duration of participation is 1 week.

Compound I has been shown in the above Examples to decrease heart rate and convert patients with PSVT to sinus rhythm.

This study is designed as a two-arm, double-blind, randomized, placebo-controlled, proof of concept study to evaluate if compound I decreases ventricular rate in an AF population. The study design is depicted in FIG. 16.

Dosing 70 mg of compound I has been selected as the initial dose in patients with Atrial Fibrillation.

Study Population

Enrollment will continue until enough patients are randomized to provide at least 50 evaluable patients in the Efficacy Population. Patients must be diagnosed with Atrial Fibrillation by a medical professional and show evidence of current AF with ventricular rate≥110 bpm at screening and prior to study drug administration. A patient will be eligible for study participation if they meet all of the following criteria: 1) aged 18 and over; 2) has provided written informed consent; 3) patients with episodes of paroxysmal, persistent or permanent AF, presenting with AF and a ventricular rate≥110 bpm, measured over 1 minute on an ECG; 4) patients should receive appropriate antithrombotic therapy as per Canadian Cardiovascular Society (CCS) guidelines: a. compound I (a calcium channel blocker) is intended for acute rate control only. If rhythm control is desired (outside of the present protocol), anticoagulation as per CCS guidelines may start after the administration of study drug.

A patient will be excluded from the study if they meet any of the following criteria: 1) has evidence of atrial flutter (ECG) at presentation; 2) has a history of stroke, TIA, or peripheral embolism within the last 3 months; 3) has received by IV route any of the following within one hour before study drug; administration: flecainide, procainamide, digoxin, beta-blocker, or calcium channel blocker; 4) has signs and symptoms of severe congestive heart failure at presentation (e.g. tachypnea, oxygen desaturation<90% unless due to known pulmonary disease, pulmonary rales, sign of peripheral hypoperfusion); 5) hemodynamic instability, with systolic blood pressure<90 mmHg or diastolic blood pressure<60 mmHg; 6) known uncorrected severe aortic or mitral stenosis; 7) hypertrophic cardiomyopathy with outflow tract obstruction; 8) has a history of second- or third-degree atrioventricular block; 9) regular rhythm suggesting a complete AV block; 10) has a history or evidence of Torsades de Pointes, sick sinus syndrome, or Brugada syndrome; 11) evidence of Acute Coronary Syndrome within the last 12 months except if patient was successfully revascularized; 12) positive pregnancy test result at screening, and females of childbearing potential who do not agree to use adequate method of contraception for the duration of the study; 13) has evidence of any clinically significant acute or chronic condition of the nasal cavity (e.g., rhinitis or deviated septum) which could interfere with administration of the study drug in either or both nasal cavities; 14) has a history of sensitivity to verapamil; 15) has previously participated in a clinical study for compound I; 16) has a history of sensitivity to any components of the investigational product; 17) signs of alcohol or drugs intoxication at the time of presentation which, in the opinion of the Investigator, would impact the validity of study results; 18) is currently participating in another drug or device study, or has received an investigational drug or device within 30 days of Screening; and 19) has evidence of clinically significant cardiovascular, endocrine, gastrointestinal, hematologic, hepatic, immunologic, neurologic, oncologic, pulmonary, psychiatric, or renal disease or any other condition which, in the opinion of the Investigator, would jeopardize the safety of the patient or impact the validity of study results.

The end of study is defined as the date of the last visit of the last study participant. Last study visit of the last study participant is the date of their last follow-up contact.

Treatments

The formulation of compound I is for intranasal administration and will consist of compound I, water, acetic acid, disodium ethylene-diamine-tetra-acetic acid (EDTA), and sulfuric acid. The dose of compound I to be evaluated in this study is 70 mg.

The formulation of placebo will consist of water, sodium acetate, disodium, EDTA, and sulfuric acid to reproduce the same pH as the compound I formulation.

The study drug is packaged a prefilled device, the Aptar Pharma Nasal Spray Bidose System (BDS).

Clinical labeling, packaging, and distribution of the study drug will be performed by PCI Pharma Services.

Labeling

Study drug will be labeled according to the requirements of local law and legislation, as well as current Good Manufacturing Practice (GMP) and International Council for Harmonization (ICH) Good Clinical Practice (GCP) guidelines. In compliance with these regulations and guidelines, the label may include information such as the study protocol number, administration sequence, lot number, storage conditions, expiry date, Sponsor identification, or appropriate cautionary language for investigative material. Proof labels, detailing actual label text, will be available in the study files.

Packaging

The study drug distributor will package the study drug in kits, according to current GMP and ICH GCP guidelines. Drug kits will be packaged in accordance to the randomization list provided by an unblinded biostatistician, and identified by a unique kit ID number that will maintain treatment blinding, while allowing unblinded personnel to identify the treatment it contains, if necessary.

Treatments Administered

Study drug will be administered at the clinical site by the Investigator or qualified designee. Each patient will receive a total of 200 μL of placebo or 70 mg of compound I (i.e., 100 μL in each nostril via the Aptar Pharma Nasal Spray Bidose System [BDS]). The devices will be prefilled and packaged. Instructions for use of the nasal spray are provided in the Appendix B. Date and time of dosing will be recorded in the eCRF.

If only one spray of the BDS is administered for any reason, it will be considered a partial dose. Missed and partial doses will be recorded in the eCRF.

Randomization and Unblinding Procedure

Each randomized patient will be assigned to receive either placebo or 70 mg of compound I; treatment will be randomized in a 1:1 ratio to yield at least 50 evaluable patients with AF in 2 groups of at least 25 each (placebo vs. compound I). To ensure an adequate sample size, enrollment in the study will continue until each treatment group reaches the minimum of 25 evaluable patients. Throughout the study, the Milestone Medical Monitor (or designated medical reviewer) will log into the Interactive Web Randomization System (IWRS) to indicate whether or not each randomized patient meets the criteria for inclusion in the Efficacy Population.

Upon confirmation of eligibility, site personnel will log in to the IWRS to obtain a blinded treatment assignment for the patient: the IWRS will specify which drug kit is assigned to which patient, without revealing the treatment group (compound I or placebo). The kit ID administered to each patient will also be recorded in the EDC system and in drug accountability documentation.

The randomization list will be generated by an IWRS vendor, and will only be accessible to limited unblinded personnel, e.g. drug packaging vendor, IWRS vendor. Blinding is critical for the integrity of the study. However, in the event of a medical emergency where revealing the study medication is critical to the care of the patient, the investigator may need to break the code. Before breaking the blind, the investigator should have determined that the information is necessary and must have contacted the MHICC. The unblinding will be done through the IWRS system. If the IWRS is not accessible, the investigator will contact the Milestone Medical Monitor. This unblinding and the reason will be clearly document by the principal investigator in the study source documents.

Prior and Concomitant Therapies

All concomitant medications and treatments used (including over-the-counter medications and herbal supplements) will be recorded in the source document and on the appropriate eCRF.

Patients who, prior to enrollment, have received any of the following drugs by IV route may be eligible to participate at least 1 hour after these drugs were administered: flecainide, procainamide, digoxin, beta-blocker, or calcium channel blocker. Time of administration of such prior treatments must be documented in the eCRF.

After study drug administration, in case of clinical symptoms representing a safety risk for the patient, it is the investigator's prerogative to use any additional treatment in accordance with the standard of care.

The use of any drugs of abuse (such as marijuana or prescription opioids) which, in the opinion of the Investigator, would impact the validity of the study results is prohibited.

Treatment Procedures

The Treatment Procedures will occur after Screening is completed and the patient's eligibility has been verified. The following procedures will be performed during the Treatment Period:

Pre-Dose (at least 10 minutes prior to dosing)
1. Confirm patient remains eligible for the study.
2. By logging in to IWRS, randomize the patient and obtain study drug kit assignment. Document the kit number in the patient's eCRF.
3. Fit the patient with a Holter monitor, and continuously record ECG from at least 10 minutes pre-dose to 6 hours after study drug administration.
4. Record blood pressure after the patient has been in a seated position for at least 5 minutes:
   1) 10 minutes prior to dosing,
   2) immediately prior to drug administration, to ensure patient eligibility prior to dosing with Systolic BP>90 mmHg
5. Perform two ECGs over 10 minutes (from the Holter monitor)
   1) at 10 minutes prior to dosing to confirm the patient is in AF,
   2) immediately prior to drug administration, to confirm that Baseline HR meets ≥110 bpm threshold
   Patients must exhibit a rapid ventricular rate (≥110 bpm measured during 1 minute) prior to drug administration in order to receive the study drug.
6. Administer Study Drug, and record time of drug administration.
   Study drug must be administered by qualified clinical site staff.
   Prior to administration, patients should be seated with their head in an upright position. Patients will be instructed to hold their breath and avoid inhaling during study drug administration.
   For 10 minutes after drug administration, patients are to remain in a seated position with their head upright, breathe normally, and refrain from blowing their nose.
   Patient should not perform any strenuous physical activity for 1-hour post-dose. Post-Dose (up to 1 hour after dosing)
7. Record blood pressure at 5, 10, 15, 30, and 60 minutes post-dose.
8. Complete the TSMQ-9 questionnaire at the end of the Treatment Period.
9. Record any adverse events.
10. In case of systolic blood pressure≤90 mmHg or clinical symptoms representing a safety risk for the patient, it is the investigator's prerogative to use any additional treatment within 60 minutes of study drug administration.
11. Beyond 60 minutes after study drug administration:
    Appropriate medical care should be offered, in accordance with the standard of care.
    The patient may be discharged from the clinic, while still wearing the Holter device as per the site staff's instructions.

Follow-Up Period

Following drug administration and post-dose activities, follow-up procedures will be performed. If the patient cannot be reached after 3 attempts, they will be considered lost to follow-up.
1. 24 hours post-dose (+/−6 hours): Safety follow-up will be performed, either via telemedicine or as an in-person visit if deemed necessary by the investigator.
   Record any Adverse Events.
   Record any concomitant medication taken since study drug administration
   Return of the Holter device will be arranged (e.g., by courier)
2. 1 week post-dose: Patients will be contacted by phone 7 days (+/−1 day) post-dosing for safety follow-up.
   Record any Adverse Events.
   Record any concomitant medication taken since study drug administration Assessments A 12-lead ECG will be performed at Screening to assess eligibility (an ECG performed per standard-of-care on the same day but prior to ICF signature will be accepted for screening purposes). Data from the ECG will be reviewed by qualified site personnel for potential concomitant disorders which would exclude the patient from the trial.

Continuous ECG recordings will be obtained during the Treatment period, from at least 10 minutes pre-dose to 6 hours post-dose via portable monitoring devices (Holter), and will provide the data for primary and secondary efficacy analyses. The files will be uploaded and stored centrally in the study database at the end of the study.

In addition, the Holter device and the associated software will be used by qualified site personnel for pre-dose Baseline HR measurements (10 minutes and immediately prior to drug administration). Following completion of patient participation, the ECGs recordings will also be reviewed by the Medical Monitor (or designee) to determine whether patients met the criteria for inclusion in the Efficacy Population.

After study drug administration, patients will be asked to complete the TSQM-9 (Appendix C).

The TSQM-9 is a 9 question, validated, indication agnostic patient reported outcome. It includes 3 items measuring treatment effectiveness, 3 items measuring treatment convenience, and 3 items measuring global satisfaction with treatment. The domain scores range from 0 to 100 with higher scores representing higher satisfaction with the treatment.

Safety assessments will include the evaluation of AEs, vital sign measurements, and ECG recordings.

Samples for the following laboratory tests will be collected at the time points specified in the schedule of assessments (Appendix A). Samples will be analyzed by the site's local laboratory. Pregnancy Test: For women of childbearing potential only, a urine or serum test will be performed at Screening and as required to confirm any suspected pregnancy Vital signs will include blood pressure, heart rate, height and weight. Blood pressure and heart rate will be measured after the patient has been in a sitting position for 5 minutes.

A complete physical examination (excluding breast, genitourinary and rectal examination) will be performed at Screening. Systems examined should include General Appearance, Eyes, ENT/Mouth, Respiratory, Cardiovascular, Gastrointestinal, Muscular, Skin, Neurological, Endocrine (including thyroid), Lymph Nodes, Allergy/Immunological, and Psychiatric.

A symptom-directed physical examination will be performed after drug administration.

Adverse Events

An AE is defined as any untoward medical occurrence in a patient or clinical investigation patient administered a pharmaceutical product that does not necessarily have a causal relationship with the product. An AE can therefore be any unfavorable and unintended sign (including a new, clinically significant abnormal laboratory finding), symptom, or disease, temporally associated with the product, whether or not related to the product.

During Screening the Investigator or designee will assess all findings from physical exams, vital signs, laboratory assessments, and diagnostic ECGs. Clinically significant findings will be recorded as medical history. Pre-existing diseases or conditions will not be considered AEs unless there is an increase in the frequency or severity, or a change in the quality, of the disease or condition. (Worsening of a pre-existing condition is considered an AE.)

Wherever possible, a specific disease or syndrome rather than individual associated signs and symptoms will be identified by the Investigator and recorded on the eCRF. However, if an observed or reported sign or symptom is not considered a component of a specific disease or syndrome by the Investigator, it will be recorded as a separate AE on the eCRF. In cases requiring medical or surgical procedures, the underlying condition, rather than the procedure itself, will be recorded as an AE(s).

Clinically significant abnormal assessments that are detected during the study or are present at screening and significantly worsen will be reported as AEs or SAEs. The Investigator will exercise his or her medical and scientific judgment in deciding whether an abnormal assessment is clinically significant. Any abnormal assessments considered clinically significant by the Investigator must be recorded on the AE page of the eCRF.

Events that occur in patients during the Treatment Period while drug is not administered are also considered AEs.

All noxious and unintended responses to a study drug related to any dose should be considered adverse drug reactions (ADRs).

The phrase "responses to a study drug" means that a causal relationship between a study drug and an AE is at least a reasonable possibility, i.e., the relationship cannot be ruled out. All AEs judged by either the reporting investigator or the sponsor as having a reasonable causal relationship to a study drug qualify as ADRs.

All AEs for which the judgment of relationship to the study drug is "possible" or higher will be considered ADRs. If a relationship to the study drug is not given, then the AE must be treated as if the relationship to the study drug were "possible."

An Unexpected Adverse Drug Reaction is defined as an adverse reaction, the nature or severity of which is not consistent with the applicable product information. For compound I, the reference safety information is included in the Investigator's Brochure currently in force. The reference safety information will be reviewed yearly, and the periodicity of the review will be harmonized with the reporting period of the Development Safety Update Report.

A serious adverse event (SAE) is any untoward medical occurrence that at any dose:

Results in death.

Is life-threatening.

The term "life-threatening" in the definition of "serious" refers to an event in which the patient was at risk of death at the time of the event; it does not refer to an event which hypothetically might have caused death if it were more severe.

Requires inpatient hospitalization or prolongation of existing hospitalization.

Inpatient hospitalization is defined as 24 hours in a hospital or an overnight stay. An elective hospital admission to treat a condition present before exposure to the study drug, or a hospital admission for a diagnostic evaluation of an AE, does not qualify the condition or event as an SAE. Further, an overnight stay in the hospital that is only due to transportation, organization, or accommodation problems and without medical background does not need to be considered a SAE.

An ablation or cardioversion for treatment of atrial fibrillation will not be considered as a SAE.

Results in persistent or significant disability/incapacity.

Is a congenital anomaly.

A congenital anomaly in an infant born to a mother who was exposed to the study drug during pregnancy is an SAE. However, a newly diagnosed pregnancy in a patient who has received a study drug is not considered an SAE unless it is suspected that the study drug(s) interacted with a contraceptive method and led to the pregnancy.

Is an important medical event.

Medical and scientific judgment should be exercised in deciding whether it is appropriate to consider other situations serious, such as important medical events that may not be immediately life-threatening or result in death or hospitalization but may jeopardize the patient or may require intervention to prevent 1 of the other outcomes listed in the definition above. Examples of such events are intensive treatment in an emergency room or at home for allergic bronchospasm, blood dyscrasias or convulsions that do not result in hospitalization, or development of drug dependency or drug abuse. The occurrence of malignant tumors is also to be considered serious An adverse reaction that is considered to be both serious and unexpected and of a suspected causality. Causality is defined as "reasonable suspected causal relationship to the medicinal product.

An AE is defined as treatment emergent if the first onset or worsening is within 24 hours after the administration of the study drug.

Due to the mechanism of action of compound I, patients could be at a higher risk of certain adverse events of special interest. Investigators should be on the alert for these events, or for symptoms which indicate an event may be present. Investigators should follow the standard protocol process for AE and SAE reporting for these AESI.

Below is a list of AEs which are of particular interest if they occur within 24 hours of compound I administration.

a) Tachyarrhythmias i) Supraventricular: occurrence of Atrial Tachycardia or Atrial Flutter lasting longer than 30 seconds ii) Ventricular:

Non-sustained ventricular tachycardia defined as equal or greater than 3 consecutives wide beats originating in the ventricles at a rate>100 bpm and terminating spontaneously Sustained ventricular tachycardia defined as wide consecutive beats originating in the ventricles at a rate>100 bpm during >30 sec or requiring termination due to hemodynamic compromise in <30 sec b) Bradyarrythmia
　i) Any sinus rate equal or less than 40 bpm lasting longer than 30 seconds
　ii) Any pause equal or greater than 3 seconds
c) Atrio-Ventricular Block
　i) New onset (not present in the ECG performed at the screening visit) of 1st° AV Block
　ii) Any occurrence of 2nd or 3rd degree AV Block (including AV dissociation or the presence of more than 2 consecutives non-conducted P waves)
d) Syncope and related events
　i) Syncope defined as a transient, self-limited loss of consciousness with an inability to maintain postural tone that is followed by spontaneous recovery.
　ii) Pre-syncope defined as a state consisting of light-headedness, muscular weakness, blurred vision, and feeling faint
　iii) Loss of consciousness defined as a partial or complete loss of consciousness with interruption of awareness of oneself and one's surroundings. When the loss of consciousness is temporary and there is spontaneous recovery it is referred to as syncope.
　iv) Dizziness defined as a false sense of motion or spinning, light-headedness or feeling faint, unsteadiness or a loss of balance, a feeling of floating, wooziness or heavy headedness. The episode may last seconds or days and may recur.
　v) Drop attack defined as a sudden fall without loss of consciousness
　vi) Hypotension is defined as a systolic blood pressure (SBP)<90 mmHg after a 5-minute rest in sitting position; when clinically severe hypotension patients experience light-headedness, nausea or vomiting.
　vii) Orthostatic hypotension defined as a physical finding defined as a systolic blood pressure decrease of at least 20 mmHg or a diastolic blood pressure decrease of at least 10 mmHg within three minutes of standing Adverse events will be collected from the time of signing the ICF until 7 days post-dose, or until the patient withdraws or discontinues from the study.

The investigator is responsible for the detection and documentation of events meeting the criteria and definition of an AE or SAE described previously. The patient will be allowed time to spontaneously report any issues since the last visit or evaluation. The investigator will then monitor and/or ask about or evaluate AEs using nonleading questions, such as:

"How are you feeling?"
"Have you experienced any issues since your last visit?"
"Have you taken any new medications since your last visit?"

Any clinically relevant observations made during the visit will also be considered AEs.

The clinical severity of an AE will be classified as:
　Mild: Usually transient and may require only minimal treatment or therapeutic intervention. The event does not generally interfere with usual activities of daily living.
　Moderate: Usually alleviated with additional specific therapeutic intervention. The event interferes with usual activities of daily living, causing discomfort but poses no significant or permanent risk of harm to the patient.
　Severe: Interrupts usual activities of daily living, or significantly affects clinical status, or may require intensive therapeutic intervention.

It is important to distinguish between severe AEs and SAEs. Severity is a classification of intensity whereas an SAE is an AE that meets serious criteria.

The outcome, including Fatal, at the time of last observation will be classified per eCRF completion instructions. Only select fatal as an outcome when the AE results in death. If more than 1 AE is possibly related to the patient's death, the outcome of death should be indicated for each such AE. Although "fatal" is usually an event outcome, events such as sudden death or unexplained death should be reported as SAEs.

The assessment of the relationship of an AE to study drug administration is a clinical decision based on all available information at the time the event is reported.

The relationship of an AE to study drug administration is to be assessed according to the following definitions:

Not related—An event that is definitely not associated with study drug administration and is judged clearly due to causes other than study drug.
　Unlikely related—An event that follows a temporal sequence from study drug administration, such that a relationship is not likely and could be reasonably explained by the patient's clinical state or other modes of therapy administered to the patient.
　Possibly related—An event that follows a reasonable temporal sequence from study drug administration, but may be due to another cause and could also be reasonably explained by the patient's clinical state or other modes of therapy administered to the patient.
　Probably related—An event that follows a reasonable temporal sequence from study drug administration that is not easily explained by another cause (e.g., known characteristics of the patient's clinical state or other treatment), and is confirmed by improvement on stopping or slowing study drug administration.
　Definitely related—An event that is clearly associated with study drug administration.

An AE/SAE that has been assessed as "possibly related" "probably related" or "definitely related" will be classified as "related" for regulatory reporting purposes. An AE/SAE that has been assessed as "not related" or "unlikely related" will be classified as "unrelated" for regulatory reporting purposes.

The following factors will also be considered:
　The temporal sequence from study drug administration;
　　The event should occur after study drug administration. The length of time from study drug exposure to event will be evaluated in the clinical context of the event.
　Underlying, concomitant, and/or intercurrent diseases;
　　Each report will be evaluated in the context of the natural history and course of the disease being treated and any other disease the patient may have.
　Concomitant medication;
　　The other medications the patient is taking or the treatment the patient receives will be examined to determine whether any might be recognized to cause the event in question.
　Known response pattern for this class of study drug;
　　Clinical and/or preclinical data may indicate whether a particular response is likely to be a class effect.

Exposure to physical and/or mental stresses; and
The exposure to stress might induce adverse changes in the recipient and provide a logical and better explanation for the event.
The pharmacology and PK of the study drug.
The known pharmacological properties (e.g., absorption, distribution, metabolism, and excretion) of the study drug will be considered.
All AEs occurring within the period of observation for the study must be documented in the eCRF with the following information, where appropriate.
AE name or term.
When the AE first occurred (start date and time).
When the AE stopped (stop date and time or an indication of "ongoing").
Severity of the AE.
Seriousness (e.g., hospitalization or death).
Outcome.
Investigator opinion regarding the AE relationship to the study drug(s).
Any AE/SAE (occurring up to a maximum of 7 days after single dose administration in the study) will be followed to a satisfactory resolution, until it becomes stable, or until it can be explained by another known cause(s) (i.e., concurrent condition or medication) and clinical judgment indicates that further evaluation is not warranted. All findings relevant to the final outcome of an AE must be included in the EDC. Patients who do not receive study drug during the study do not need AEs followed.
All women of childbearing potential who participate in the study should be counseled on the need to practice at least 1 form of adequate birth control and on the importance of avoiding pregnancy during study participation. Women should be instructed to contact the investigator or study staff immediately if pregnancy occurs or is suspected within 30 days of study drug administration.
Pregnancy testing will be conducted at the Screening Visit on every woman of childbearing potential. A woman who is found to be pregnant at the Screening Visit will be excluded from the study and considered to be a screening failure.
MHICC will be requesting follow up query with the Investigator in a "Pregnancy query form" for the status of the pregnancy (at least once in each trimester) until the outcome of the pregnancy, even if the patient has completed the study or study is closed. Also, the baby should be followed until one month post-delivery.
The maximal dose of compound I should not be exceeded during the study, as study drug is dispensed for single use only.
Overdose that occurs during the study will be treated and documented as an AE/UAE/SAE if it fulfills the criteria. If the overdose does not result in an AE, it should be reported in written form to the designated individual(s) who receive SAE notification.

Statistics

This section describes the statistical methods to be used to analyze efficacy and safety endpoints. These methods may be revised and updated due to reasons such as regulatory requirements or need for further clarifications.
The final analysis plan will be documented in a formal statistical analysis plan (SAP) that must be finalized before database lock. The SAP will include details on how variables will be derived, how missing and censoring data will be handled, and how data will be presented as well as the details on statistical methods to be used for safety and efficacy analyses.
The SAP will take precedence over the protocol for any description of statistical analyses. The final clinical study report will discuss deviations from the SAP, if any.

Study Endpoints

Efficacy variables will be obtained from the Holter recordings measured by a central core laboratory. In case of conversion to sinus rhythm, only heart rate measurements prior to sinus conversion will be used to derive efficacy variables.
The primary efficacy variable will be:
The maximum reduction in ventricular rate, measured on Holter monitoring, within 60 minutes from drug administration.
Baseline ventricular rate is defined as the average heart rate over five minutes immediately prior to drug administration.
Nadir is defined as the lowest moving average heart rate over five minutes recorded in the primary evaluation period, i.e., 60 minutes post drug administration. The moving averages are 5 minutes' averages of different subsets of the full data set and are calculated by using the "shifting forward" method; that is, excluding the first number of the series and including the next value in the subset.
Maximum reduction will be calculated as the change between baseline value and nadir.
The secondary efficacy variables will include:
Elapsed time from drug administration to nadir
Percentage of patients achieving ventricular rate of <100 bpm in the 60 minutes post drug administration.
Elapsed time from drug administration to ventricular rate<100 bpm
Duration of ventricular rate<100 bpm in the 60 minutes post drug administration. Duration will be set to zero in patients who will not achieve ventricular rate<100 bpm and will be calculated as the sum of the time periods during which the patient has a heart rate below the target ventricular rate.
Percentage of patients with 10% reduction from baseline ventricular rate in the 60 minutes post drug administration.
Elapsed time from drug administration to 10% reduction from baseline ventricular rate
Duration of 10% reduction from baseline ventricular rate in the 60 minutes post drug administration. Duration will be set to zero in patients who will not achieve 10% reduction and will be calculated as the sum of the time periods during which the patient has a heart rate below the target ventricular rate.
Percentage of patients with 20% reduction from baseline ventricular rate in the 60 minutes post drug administration.
Elapsed time from drug administration to 20% reduction in ventricular rate
Duration of 20% reduction from baseline ventricular rate in the 60 minutes post drug administration. Duration will be set to zero in patients who will not achieve 20% reduction and will be calculated as the sum of the time periods during which the patient has a heart rate below the target ventricular rate.
Percentage of patients cardioverting into sinus rhythm (for at least 30 seconds) in the 60 minutes post drug administration
Elapsed time from drug administration to cardioversion into sinus rhythm
Area under the curve (AUC) of heart rate over the 60 minutes and the 360 minutes post drug administration.

Patient satisfaction with treatment, as measured by the Treatment Satisfaction Questionnaire for Medication.

Safety variables will include clinical adverse events (AEs), vital signs, and findings from electrocardiographic analysis (ventricular arrhythmia (PVCs, NSVT), any AV block).

The primary efficacy variable for this study is the maximal reduction of ventricular rate after study drug administration. Accounting for a two-sided test with a type I error rate of $\alpha=0.05$, 25 patients per group will provide 93% power to detect a 20 bpm absolute difference in ventricular rate from baseline between active drug and placebo, assuming a standard deviation of 20 bpm.

The following 3 analysis populations are planned for this study:

Safety Population: All randomized patients who receive the study drug. Patients will be analyzed as per actual treatment received in the Safety population.

Modified Intent to Treat (mITT) Population: All randomized patients who receive the study drug and who have a Holter recording post study drug administration. Patients will be analyzed as per treatment assigned by randomization in the mITT population.

Efficacy Population: All patients included in the mITT population, excluding patients who convert to sinus rhythm or with a lost ECG signal within 60 minutes post study drug administration. Patients will be analyzed as per treatment assigned by randomization in the Efficacy population.

Unless otherwise indicated, all testing of statistical significance will be 2-sided, and a difference resulting in a P value of less than or equal to 0.05 will be considered statistically significant.

Summary statistics will be provided for the variables described in the following sections. For continuous variables, these statistics will typically include the number of patients, mean, standard deviation (SD), median, minimum, Q1, Q3 and maximum. For categorical variables, these statistics will typically include the number and percentage of patients in each category.

In general, parametric analyses are planned. However, according to the distribution of the efficacy variables, non-parametric tests could be used or a logarithmic transformation could be applied on the variables before proceeding to the planned parametric analyses.

The efficacy analyses will compare placebo-treated patients versus compound I-treated patients. Efficacy endpoint analyses will include summaries, both over time and as comparisons between placebo and compound I. Continuous efficacy data will be presented with n, minimum, maximum, median, mean, and standard deviation, whereas discrete efficacy data will be summarized with frequency counts and percentages.

The primary efficacy analysis will be performed on the Efficacy Population and will compare the maximum reduction in ventricular rate in placebo-treated patients versus compound I-treated patients. This comparison will be done using an analysis of covariance (ANCOVA) adjusting for the value of ventricular rate at baseline.

Sensitivity analysis for the primary efficacy endpoint will also be performed in the mITT population using an ANCOVA as described above.

The secondary efficacy analyses will be performed on the Efficacy Population and on the mITT Population, and will compare:

Elapsed time from drug administration to nadir. Group comparison will be done using an ANCOVA adjusting for baseline ventricular rate.

Percentage of patients achieving ventricular rate of <100 bpm, reaching 10% and 20% reduction from baseline ventricular rate. For each of these three endpoints, group comparison will be done using a chi-square test or a Fisher exact test if more than 20% of cells have expected frequencies<5.

Elapsed time from drug administration to ventricular rate<100 bpm, to 10% reduction from baseline ventricular rate, and to 20% reduction from baseline ventricular rate. For each of these three endpoints, group comparison will be done using the Kaplan-Meier method and a Wilcoxon test for censored data.

Duration of 10% and 20% ventricular rate reductions will be analyzed using an ANCOVA adjusting for baseline ventricular rate.

Mean heart rate over time will be plotted with 95% confidence interval error bars.

AUC of heart rate over 60 minutes. AUC will be calculated over the specific Holter recording period for each patient and indexed to a period of 60 minutes. Group comparison will be done using an ANCOVA adjusting for baseline ventricular rate.

Patient satisfaction with treatment, as measured by the TSQM. Domaine scores (ranging from 0 to 100) will be analyzed using a t-test or a Mann-Whitney-Wilcoxon test, according to the distribution of the variable.

Parameters analyzed in mITT Population only:

Percentage of patients cardioverting into sinus rhythm (for at least 30 seconds). Group comparison will be done using a chi-square test or a Fisher exact test if more than 20% of cells have expected frequencies<5.

Elapsed time from drug administration to cardioversion into sinus rhythm. Group comparison will be done using using the Kaplan-Meier method and a Wilcoxon test for censored data.

AUC of heart rate over 360 minutes. AUC will be calculated over the specific Holter recording period for each patient and indexed to a period of 360 minutes. Group comparison will be done using an ANCOVA adjusting for baseline ventricular rate.

Safety analyses will be conducted using data from the Safety Population.

Safety and tolerability will be assessed through AEs, vital signs measurements, and ECG recordings.

Safety data will be summarized with descriptive statistics. Continuous safety data will be presented with n, minimum, Q1, Q3, maximum, median, mean, and standard deviation, whereas discrete safety data will be summarized with frequency counts and percentages.

Adverse events will be coded by system organ class (SOC) and preferred term using the Medical Dictionary for Regulatory Activities reporting system.

The number and percentage of patients with AEs will be displayed for each treatment group by SOC and preferred term. Additionally, AEs will be tabulated for each treatment group by severity and by relationship to the study drug. A listing of and tabulation of SAEs will be provided.

Treatment Emergent Adverse Events (adverse events occur within 24 hours after study drug administration) will be coded by system organ class and analyzed for each treatment group.

Example 7: PK Analysis for Two 70 mg Dose Nasal Administration of Compound I Versus One 70 mg Dose Nasal Administration of Compound I The serum concentration of compound I over time from the first administration for the study arm with a single 70 mg dose administration of compound I was compared with the study arm with two 70 mg dose administrations of compound I. The second 70 mg dose of compound I was administered approximately 10 minutes after the first dose. As is shown in FIG. 17 and Tables 2 and 3, administration of the second 70 mg dose raised the serum concentration of compound I above that observed with a single 70 mg dose, and the serum concentration remained above that observed for the single 70 mg dose for 60 minutes from first administration.

TABLE 2

One 70 mg dose nasal administration of compound I

| Time | N | Mean | SD | Min | Median | Max |
|---|---|---|---|---|---|---|
| 0 | 12 | 0.00 | 0.00 | 0.00 | 0.00 | 0.00 |
| 0.5 | 12 | 0.00 | 0.00 | 0.00 | 0.00 | 0.00 |
| 1.5 | 11 | 11.79 | 16.76 | 0.00 | 5.20 | 56.12 |
| 3 | 12 | 62.82 | 61.22 | 11.45 | 32.60 | 205.27 |
| 5 | 12 | 90.64 | 67.37 | 21.18 | 67.70 | 191.63 |
| 7 | 12 | 83.04 | 45.40 | 28.61 | 74.22 | 152.59 |
| 9 | 12 | 73.39 | 37.77 | 25.94 | 69.68 | 130.50 |
| 10.5 | 12 | 67.95 | 32.39 | 30.24 | 59.91 | 121.45 |
| 11.5 | 12 | 66.91 | 30.49 | 31.61 | 59.09 | 119.67 |
| 13 | 12 | 62.34 | 27.41 | 29.29 | 59.07 | 103.40 |
| 15 | 12 | 57.44 | 25.52 | 26.98 | 52.11 | 111.44 |
| 17 | 12 | 50.32 | 19.60 | 26.92 | 41.80 | 90.05 |
| 20 | 12 | 49.43 | 17.82 | 22.74 | 46.51 | 80.55 |
| 25 | 12 | 41.86 | 15.12 | 19.26 | 42.30 | 66.12 |
| 35 | 12 | 33.35 | 11.93 | 15.09 | 36.90 | 51.52 |
| 60 | 12 | 20.41 | 6.85 | 8.89 | 22.06 | 31.10 |
| 100 | 12 | 13.91 | 5.56 | 6.20 | 12.75 | 23.24 |
| 240 | 12 | 5.90 | 2.89 | 1.48 | 5.91 | 11.01 |
| 370 | 12 | 2.49 | 1.64 | 0.00 | 2.51 | 6.08 |
| 730 | 12 | 0.76 | 1.05 | 0.00 | 0.00 | 3.17 |
| 1450 | 12 | 0.10 | 0.35 | 0.00 | 0.00 | 1.20 |

TABLE 3

Two 70 mg dose nasal administration of compound I

| Time | N | Mean | SD | Min | Median | Max |
|---|---|---|---|---|---|---|
| 0 | 12 | 0.00 | 0.00 | 0.00 | 0.00 | 0.00 |
| 0.5 | 11 | 0.00 | 0.00 | 0.00 | 0.00 | 0.00 |
| 1.5 | 12 | 22.21 | 24.58 | 0.00 | 10.25 | 70.33 |
| 3 | 12 | 81.03 | 70.83 | 6.83 | 77.71 | 232.19 |
| 5 | 12 | 91.84 | 62.07 | 11.42 | 90.41 | 216.99 |
| 7 | 12 | 85.77 | 51.57 | 17.16 | 91.42 | 180.76 |
| 9 | 12 | 73.20 | 39.22 | 15.37 | 77.41 | 144.91 |
| 10.5 | 12 | 65.97 | 33.86 | 14.49 | 65.18 | 143.87 |
| 11.5 | 11 | 96.77 | 55.76 | 15.52 | 102.11 | 215.35 |
| 13 | 11 | 115.15 | 84.61 | 22.46 | 93.56 | 320.44 |
| 15 | 11 | 110.39 | 85.38 | 25.17 | 76.88 | 316.92 |
| 17 | 12 | 94.71 | 59.83 | 27.74 | 79.45 | 246.61 |
| 20 | 12 | 79.87 | 42.81 | 26.31 | 79.13 | 188.83 |
| 25 | 12 | 66.89 | 26.45 | 32.13 | 65.09 | 128.22 |
| 35 | 12 | 51.73 | 17.54 | 30.32 | 49.28 | 84.54 |
| 60 | 12 | 30.45 | 9.67 | 14.92 | 31.01 | 46.30 |
| 100 | 12 | 18.57 | 7.20 | 7.50 | 18.22 | 29.24 |
| 240 | 12 | 7.74 | 3.87 | 3.04 | 7.83 | 14.35 |

TABLE 3-continued

Two 70 mg dose nasal administration of compound I

| Time | N | Mean | SD | Min | Median | Max |
|---|---|---|---|---|---|---|
| 370 | 12 | 3.06 | 1.61 | 1.25 | 2.47 | 6.08 |
| 730 | 12 | 1.05 | 1.23 | 0.00 | 0.58 | 3.15 |
| 1450 | 12 | 0.24 | 0.58 | 0.00 | 0.00 | 1.72 |

Numbered Embodiments

1. A method of treating a cardiac arrhythmia in a subject in need thereof with a therapeutically effective amount of compound I having a structure according to the formula:

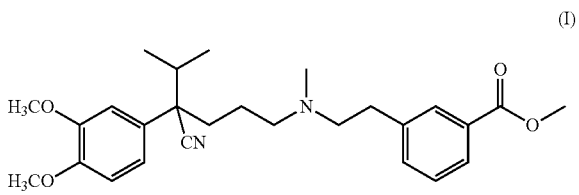 [SMILES: COC(=O)c1cccc(CCN(C)CCCC(C#N)(c2ccc(OC)c(OC)c2)C(C)C)c1]

(I)

the method comprising nasally administering to the subject (i) a first dose, and (ii) a second dose of an aqueous composition comprising a pharmaceutically acceptable acetate or methanesulfonate salt of compound I, or a racemate or enantiomer thereof, wherein the acetate or methanesulfonate salt of compound I, or the racemate or enantiomer thereof, is dissolved in the aqueous composition at a concentration of 350 mg/mL±50 mg/mL, and wherein the second dose of the compound is administered between 5 minutes and 25 minutes after the first dose.

2. A method of treating angina in a subject in need thereof with a therapeutically effective amount of compound I having a structure according to the formula:

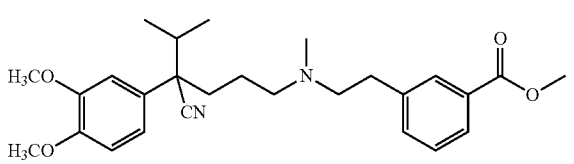

(I)

the method comprising nasally administering to the subject (i) a first dose, and (ii) a second dose of an aqueous composition comprising a pharmaceutically acceptable acetate or methanesulfonate salt of compound I, or a racemate or enantiomer thereof, wherein the acetate or methanesulfonate salt of compound I, or the racemate or enantiomer thereof, is dissolved in the aqueous composition at a concentration of 350 mg/mL±50 mg/mL, and wherein the second dose of the compound is administered between 5 minutes and 25 minutes after the first dose.

3. A method of treating a migraine in a subject in need thereof with a therapeutically effective amount of compound I having a structure according to the formula:

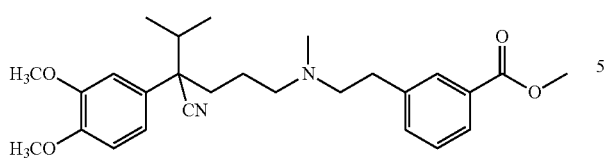

the method comprising nasally administering to the subject (i) a first dose, and (ii) a second dose of an aqueous composition comprising a pharmaceutically acceptable acetate or methanesulfonate salt of compound I, or a racemate or enantiomer thereof, wherein the acetate or methanesulfonate salt of compound I, or the racemate or enantiomer thereof, is dissolved in the aqueous composition at a concentration of 350 mg/mL±50 mg/mL, and wherein the second dose of the compound is administered between 5 minutes and 25 minutes after the first dose.

4. The method of any one of embodiments 1-3, wherein the aqueous composition comprises the acetate salt of compound I.

5. The method any one of embodiments 1-4, wherein the aqueous composition comprises the acetate salt of the S-enantiomer of compound I.

6. The method of embodiment 1, wherein the cardiac arrhythmia is paroxysmal supraventricular tachycardia (PSVT), atrial fibrillation, or ventricular tachycardia.

7. The method of embodiment 6, wherein the cardiac arrhythmia is PSVT.

8. The method of embodiment 6, wherein the cardiac arrhythmia is atrial fibrillation.

9. The method of embodiment 2, wherein the angina is stable angina or Prinzmetal's angina.

10. The method of any one of embodiments 1-9, wherein the first and the second dose each comprises between 150 microliters and 200 microliters of the aqueous composition.

11. The method of embodiment 10, wherein the first and the second dose each comprises no more than two single pump spray dosages.

12. The method of embodiment 11, wherein each single pump spray dosage comprises 35 mg±3.5 mg of the acetate salt of the S-enantiomer of compound I.

13. The method of embodiment 12, wherein each of the first and the second dose comprises administering no more than 100 microliters of the aqueous composition to each nostril of the subject.

14. The method of any one of embodiments 1-13 wherein the subject is a human.

15. The method of any one of embodiments 1-14, wherein the aqueous composition comprises from 40% to 85% (w/v) water.

16. The method of any one of embodiments 1-15, wherein the aqueous composition has a pH of 4.5±1.5.

17. The method of embodiment 16, wherein the aqueous composition has a pH of 4.5±0.1.

18. The method of any one of embodiments 1-17, wherein the aqueous composition further comprises a chelating agent.

19. The method of any one of embodiments 1-18, wherein the aqueous composition further comprises EDTA.

20. The method of any one of embodiments 1-19, wherein the aqueous composition further comprises a pharmaceutically acceptable excipient.

21. The method of any one of embodiments 1-20, wherein the aqueous composition is a homogeneous composition at room temperature.

22. An aqueous composition comprising a pharmaceutically acceptable acetate or methanesulfonate salt of a compound having a structure according to the formula:

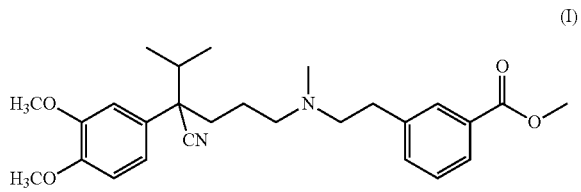 [SMILES: COC(=O)c1cccc(CCN(C)CCCC(C#N)(c2ccc(OC)c(OC)c2)C(C)C)c1]

or a racemate or enantiomer thereof, for use in treating a cardiac arrhythmia in a subject in need thereof, wherein the aqueous composition is formulated for nasal administration to the subject as (i) a first dose, and (ii) a second dose, wherein the acetate or methanesulfonate salt of compound I, or the racemate or enantiomer thereof, is dissolved in the aqueous composition at a concentration of 350 mg/mL±50 mg/mL, and wherein the second dose of the compound is to be administered between 5 minutes and 25 minutes after the first dose.

23. An aqueous composition comprising a pharmaceutically acceptable acetate or methanesulfonate salt of a compound having a structure according to the formula:

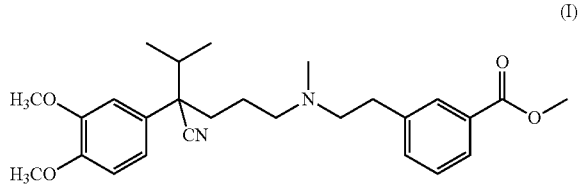 [SMILES: COC(=O)c1cccc(CCN(C)CCCC(C#N)(c2ccc(OC)c(OC)c2)C(C)C)c1]

or a racemate or enantiomer thereof, for use in treating angina in a subject in need thereof, wherein the aqueous composition is formulated for nasal administration to the subject as (i) a first dose, and (ii) a second dose, wherein the acetate or methanesulfonate salt of compound I, or the racemate or enantiomer thereof, is dissolved in the aqueous composition at a concentration of 350 mg/mL±50 mg/mL, and wherein the second dose of the compound is to be administered between 5 minutes and 25 minutes after the first dose.

24. An aqueous composition comprising a pharmaceutically acceptable acetate or methanesulfonate salt of a compound having a structure according to the formula:

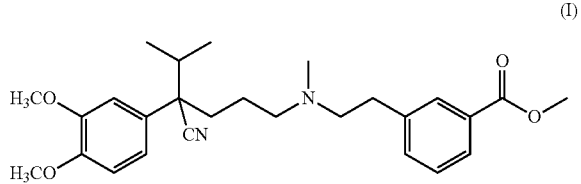

or a racemate or enantiomer thereof, for use in treating a migraine in a subject in need thereof, wherein the aqueous composition is formulated for nasal administration to the subject as (i) a first dose, and (ii) a second dose, wherein the acetate or methanesulfonate salt of compound I, or the racemate or enantiomer thereof, is dissolved in the aqueous composition at a concentration of 350 mg/mL±50 mg/mL, and wherein the second dose of the compound is to be administered between 5 minutes and 25 minutes after the first dose.

25. The aqueous composition for use of any one of embodiments 22-24, wherein the aqueous composition comprises the acetate salt of compound I.

26. The aqueous composition for use of any one of embodiments 22-25, wherein the aqueous composition comprises the acetate salt of the S-enantiomer of compound I.

27. The aqueous composition for use of embodiment 22, wherein the cardiac arrhythmia is paroxysmal supraventricular tachycardia (PSVT), atrial fibrillation, or ventricular tachycardia.

28. The aqueous composition for use of embodiment 27, wherein the cardiac arrhythmia is PSVT.

29. The aqueous composition for use of embodiment 27, wherein the cardiac arrhythmia is atrial fibrillation.

30. The aqueous composition for use of embodiment 23, wherein the angina is stable angina or Prinzmetal's angina.

31. The aqueous composition for use of any one of embodiments 1-30, wherein the first and the second dose each comprises between 150 microliters and 200 microliters of the aqueous composition.

32. The aqueous composition for use of embodiment 31, wherein the first and the second dose each comprises no more than two single pump spray dosages.

33. The aqueous composition for use of embodiment 32, wherein each single pump spray dosage comprises 35 mg±3.5 mg of the acetate salt of the S-enantiomer of compound I.

34. The aqueous composition for use of embodiment 33, wherein each of the first and the second dose is formulated for administration of no more than 100 microliters of the aqueous composition to each nostril of the subject.

35. The aqueous composition for use of any one of embodiments 22-34 wherein the subject is a human.

36. The aqueous composition for use of any one of embodiments 22-35, wherein the aqueous composition comprises from 40% to 85% (w/v) water.

37. The aqueous composition for use of any one of embodiments 22-36, wherein the aqueous composition has a pH of 4.5±1.5.

38. The aqueous composition for use of embodiment 37, wherein the aqueous composition has a pH of 4.5±0.1.

39. The aqueous composition for use of any one of embodiments 22-38, wherein the aqueous composition further comprises a chelating agent.

40. The aqueous composition for use of any one of embodiments 22-39, wherein the aqueous composition further comprises EDTA.

41. The aqueous composition for use of any one of embodiments 22-40, wherein the aqueous composition further comprises a pharmaceutically acceptable excipient.

42. The aqueous composition for use of any one of embodiments 22-41, wherein the aqueous composition is a homogeneous composition at room temperature.

43. The method of any one of embodiments 1-3 or the aqueous composition for use of any one of embodiments 22-24, wherein the second dose is administered or is to be administered between 10 and 15 minutes after the first dose.

44. The method of any one of embodiments 1-3 or the aqueous composition for use of any one of embodiments 22-24, wherein the second dose is administered or is to be administered between 30 and 60 minutes after the first dose.

45. The method of any one of embodiments 1-3 or the aqueous composition for use of any one of embodiments 22-24 wherein the subject is a human.

46. A method of treating atrial fibrillation in a subject in need thereof with a therapeutically effective amount of compound I, the method comprising nasally administering to the subject an aqueous composition comprising a pharmaceutically acceptable acetate salt of compound I, or a racemate or enantiomer thereof, wherein the acetate salt of compound I, or the racemate or enantiomer thereof, is dissolved in the aqueous composition at a concentration of 350 mg/mL±50 mg/mL, and wherein the second dose of the compound is administered between 5 minutes and 60 minutes after the first dose.

47. An aqueous composition comprising a pharmaceutically acceptable acetate salt of compound I or a racemate or enantiomer thereof, for use in treating atrial fibrillation in a subject in need thereof, wherein the aqueous composition is formulated for nasal administration to the subject, and wherein the acetate salt of compound I, or the racemate or enantiomer thereof, is dissolved in the aqueous composition at a concentration of 350 mg/mL±50 mg/mL, and wherein the second dose of the compound is to be administered between 5 minutes and 60 minutes after the first dose.

48. The method of embodiment 46 or the composition for use of embodiment 47, wherein the second dose is administered or is to be administered between 5 and 25 minutes, 10 and 35 minutes, 25 and 45 minutes, or 45 and 60 minutes after the first dose.

49. The method of embodiment 46 or the composition for use of embodiment 47, wherein the treatment comprises administering an aqueous composition comprising a pharmaceutically acceptable acetate or methanesulfonate salt of compound I, or a racemate or enantiomer thereof, as an adjunctive treatment where the subject is to be treated with at least one anti-arrhythmic medication.

50. The method or composition for use of claim 49, wherein the anti-arrhythmic medication is a beta blocker, a calcium channel blocker, a sodium channel blocker, a potassium channel blocker, digoxin, digitalis, adenosine, or an antiplatelet drug.

51. The method or composition for use of any one of embodiments 46-50, wherein the method or use reduces the heart rate of the subject.

52. A kit for treating a cardiac arrhythmia, such as PSVT or atrial fibrillation, in a subject in need thereof wherein the kit comprises a nasal delivery system comprising two doses of a therapeutically effective amount of compound I having a structure according to the formula:

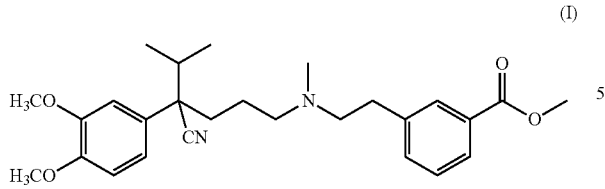

and instructions for nasally administering to the subject (i) a first dose, and, optionally, (ii) a second dose of an aqueous composition comprising a pharmaceutically acceptable acetate or methanesulfonate salt of compound I, or a racemate or enantiomer thereof, wherein the acetate or methanesulfonate salt of compound I, or the racemate or enantiomer thereof, is dissolved in the aqueous composition at a concentration of 350 mg/mL±50 mg/mL, and wherein the second dose of the compound is to be administered between 5 minutes and 60 minutes after the first dose.

53. A kit for treating angina in a subject in need thereof wherein the kit comprises a nasal delivery system comprising two doses of a therapeutically effective amount of compound I having a structure according to the formula:

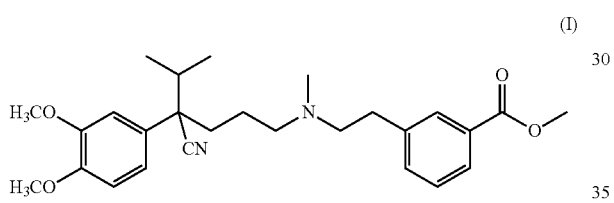

and instructions for nasally administering to the subject (i) a first dose, and, optionally, (ii) a second dose of an aqueous composition comprising a pharmaceutically acceptable acetate or methanesulfonate salt of compound I, or a racemate or enantiomer thereof, wherein the acetate or methanesulfonate salt of compound I, or the racemate or enantiomer thereof, is dissolved in the aqueous composition at a concentration of 350 mg/mL±50 mg/mL, and wherein the second dose of the compound is to be administered between 5 minutes and 60 minutes after the first dose.

54. A kit for treating a migraine in a subject in need thereof wherein the kit comprises a nasal delivery system comprising two doses of a therapeutically effective amount of compound I having a structure according to the formula:

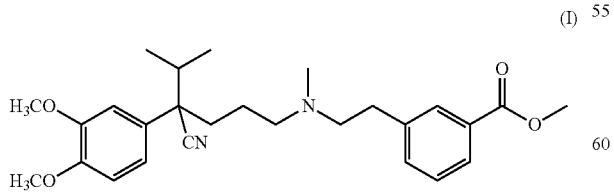

and instructions for nasally administering to the subject (i) a first dose, and, optionally, (ii) a second dose of an aqueous composition comprising a pharmaceutically acceptable acetate or methanesulfonate salt of compound I, or a racemate or enantiomer thereof, wherein the acetate or methanesulfonate salt of compound I, or the racemate or enantiomer thereof, is dissolved in the aqueous composition at a concentration of 350 mg/mL±50 mg/mL, and wherein the second dose of the compound is to be administered between 5 minutes and 60 minutes after the first dose.

55. The kit of embodiment 52, 53, or 54, wherein the second dose is administered between 5 and 25 minutes, 10 and 35 minutes, 25 and 45 minutes, or 45 and 60 minutes after the first dose.

56. The kit of any one of embodiments 52-55, wherein the aqueous composition comprises the acetate salt of compound I.

57. The kit of embodiment 56, wherein the aqueous composition comprises the acetate salt of the S-enantiomer of compound I.

58. The kit of any one of embodiments 52-57, wherein the first and the second dose each comprises between 150 microliters and 200 microliters of the aqueous composition.

59. The kit of any one of embodiments 52-58, wherein the first and the second dose each comprises no more than two single pump spray dosages.

60. The kit of embodiment 59, wherein each single pump spray dosage comprises 35 mg±3.5 mg of the acetate salt of the S-enantiomer of compound I.

61. The kit of embodiment 60, wherein each of the first and the second dose comprises administering no more than 100 microliters of the aqueous composition to each nostril of the subject.

62. The kit of any one of embodiments 52-61, wherein the subject is a human.

63. The method or aqueous composition for use of any one of embodiments 1-45, wherein the method or use reduces the heart rate of the subject.

64. A method of reducing the heart rate of a subject in need thereof with a therapeutically effective amount of compound I having a structure according to the formula:

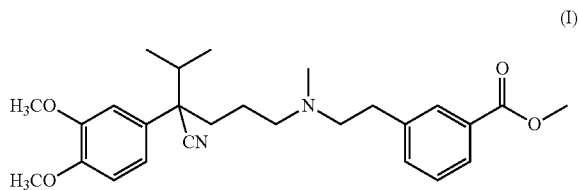 [SMILES: COC(=O)c1cccc(CCN(C)CCCC(C#N)(c2ccc(OC)c(OC)c2)C(C)C)c1]

the method comprising nasally administering to the subject (i) a first dose, and (ii) a second dose of an aqueous composition comprising a pharmaceutically acceptable acetate or methanesulfonate salt of compound I, or a racemate or enantiomer thereof, wherein the acetate or methanesulfonate salt of compound I, or the racemate or enantiomer thereof, is dissolved in the aqueous composition at a concentration of 350 mg/mL±50 mg/mL, and wherein the second dose of the compound is administered between 5 minutes and 60 minutes after the first dose.

65. An aqueous composition comprising a pharmaceutically acceptable acetate or methanesulfonate salt of compound I or a racemate or enantiomer thereof, for use in reducing the heart rate of a subject in need thereof, wherein the aqueous composition is formulated for nasal administration to the subject as (i) a first dose, and (ii) a second dose, and wherein the acetate or methanesulfonate salt of compound I, or the racemate or enantiomer thereof, is dissolved in the aqueous composition at a concentration of 350 mg/mL±50 mg/mL, and wherein the second dose of the compound is to be administered between 5 minutes and 60 minutes after the first dose.

66. The method of any one of embodiments 1-3, 46, or 64, or the composition for use of any one of embodiments 22-24, 47, or 65, wherein a serum concentration of compound I in the subject of at least 100 ng/ml is reached within 13 minutes of administration of the first dose of compound I.

67. The method of any one of embodiments 1-3, 46, or 64, or the composition for use of any one of embodiments 22-24, 47, or 65, wherein a serum concentration of compound I in the subject of at least 70 ng/ml is maintained from 5 minutes to at least 20 minutes after administration of the first dose of compound I.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All references, patents, patent application publications, and patent applications cited herein are hereby incorporated by reference to the same extent as if each of these references, patents, patent application publications, and patent applications were separately incorporated by reference herein.

What is claimed is:

1. A method of treating a cardiac arrhythmia in a subject in need thereof with a therapeutically effective amount of compound I having a structure according to the formula:

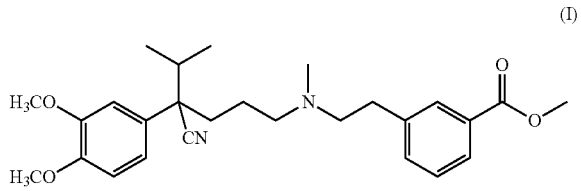 [SMILES: COC(=O)c1cccc(CCN(C)CCCC(C#N)(c2ccc(OC)c(OC)c2)C(C)C)c1]

the method comprising nasally administering to the subject (i) a first dose, and (ii) a second dose of an aqueous composition comprising a pharmaceutically acceptable acetate or methanesulfonate salt of compound I, or a racemate or enantiomer thereof, wherein the acetate or methanesulfonate salt of compound I, or the racemate or enantiomer thereof, is dissolved in the aqueous composition at a concentration of 350 mg/mL±50 mg/mL, wherein the second dose of the compound is administered between 8 minutes and 16 minutes after the first dose, wherein the first dose and the second dose are the same, and wherein the first and the second dose each comprises between 60 mg and 80 mg of compound I.

2. The method of claim 1, wherein the aqueous composition comprises the acetate salt of compound I.

3. The method of claim 1, wherein the aqueous composition comprises the acetate salt of an S-enantiomer of compound I.

4. The method of claim 1, wherein the cardiac arrhythmia is paroxysmal supraventricular tachycardia (PSVT), atrial fibrillation, or ventricular tachycardia.

5. The method of claim 4, wherein the cardiac arrhythmia is PSVT.

6. The method of claim 4, wherein the cardiac arrhythmia is atrial fibrillation.

7. The method of claim 1, wherein the first and the second dose each comprises no more than two single pump spray dosages.

8. The method of claim 7, wherein each single pump spray dosage comprises 35 mg±3.5 mg of the acetate salt of an S-enantiomer of compound I.

9. The method of claim 8, wherein each of the first and the second dose comprises administering no more than 100 microliters of the aqueous composition to each nostril of the subject.

10. The method of claim 1, wherein the subject is a human.

11. The method of claim 1, wherein the aqueous composition comprises from 40% to 85% (w/v) water.

12. The method of claim 1, wherein the aqueous composition has a pH of 4.5±1.5.

13. The method of claim 1, wherein the aqueous composition further comprises a chelating agent.

14. The method of claim 1, wherein the aqueous composition further comprises EDTA.

15. The method of claim 1, wherein the aqueous composition further comprises a pharmaceutically acceptable excipient.

16. The method of claim 1, wherein the aqueous composition is a homogeneous composition at room temperature.

17. The method of claim 1, wherein the method reduces the heart rate of the subject.

18. The method of claim 1, wherein the aqueous composition comprises the methanesulfonate salt of compound I.

19. The method of claim 7, wherein each single pump spray dosage comprises 35 mg±3.5 mg of the methanesulfonate salt of compound I.

20. The method of claim 1, wherein the second dose of the compound is administered 10±2 minutes after the first dose.

21. The method of claim 1, wherein the second dose of the compound is administered 10±1 minute after the first dose.

22. The method of claim 1, wherein the first and the second dose each comprises 70 mg±10% of compound I.

* * * * *